(12) United States Patent
Cai et al.

(10) Patent No.: US 8,324,240 B2
(45) Date of Patent: Dec. 4, 2012

(54) FUSED AMINO PYRIDINE AS HSP90 INHIBITORS

(75) Inventors: Xiong Cai, Belmont, MA (US); Changgeng Qian, Wayland, MA (US); Haixiao Zhai, Bedford, MA (US)

(73) Assignee: Curis, Inc., Lexington, MA (US)

( * ) Notice: Subject to any disclaimer, the term of this patent is extended or adjusted under 35 U.S.C. 154(b) by 612 days.

(21) Appl. No.: 12/045,509

(22) Filed: Mar. 10, 2008

(65) Prior Publication Data
US 2008/0234314 A1 Sep. 25, 2008

Related U.S. Application Data

(60) Provisional application No. 60/895,921, filed on Mar. 20, 2007, provisional application No. 61/015,288, filed on Dec. 20, 2007.

(51) Int. Cl.
*A61K 31/437* (2006.01)
*C07D 471/04* (2006.01)
*A61P 35/04* (2006.01)
*A61P 25/00* (2006.01)

(52) U.S. Cl. ...................... 514/303; 546/118
(58) Field of Classification Search .................. 514/303; 546/118
See application file for complete search history.

(56) References Cited

U.S. PATENT DOCUMENTS

| | | | |
|---|---|---|---|
| 5,644,063 A * | 7/1997 | Lindstrom et al. | 546/294 |
| 6,500,855 B1 * | 12/2002 | Lam et al. | 514/415 |
| 6,723,727 B1 | 4/2004 | Anuschirwan et al. | |
| 7,138,401 B2 | 11/2006 | Kasibhatla et al. | |
| 7,138,402 B2 | 11/2006 | Kasibhatla et al. | |
| 7,160,885 B2 | 1/2007 | Currie et al. | |
| 7,169,801 B2 | 1/2007 | Bressi et al. | |
| 7,241,890 B2 | 7/2007 | Kasibhatla et al. | |
| 2004/0102458 A1 | 5/2004 | Chiosis et al. | |
| 2004/0204428 A1 * | 10/2004 | Giorgio et al. | 514/263.2 |
| 2005/0049263 A1 | 3/2005 | Kasibhatla et al. | |
| 2006/0148805 A1 | 7/2006 | Chen et al. | |
| 2007/0105874 A1 | 5/2007 | Zhang et al. | |
| 2007/0253896 A1 | 11/2007 | Le Brazidec et al. | |
| 2007/0275984 A1 | 11/2007 | Imogai et al. | |
| 2008/0221132 A1 | 9/2008 | Cai et al. | |
| 2008/0234297 A1 | 9/2008 | Qian et al. | |

FOREIGN PATENT DOCUMENTS

| | | |
|---|---|---|
| EP | 1 221 444 A1 | 7/2002 |
| WO | 95/02597 A1 | 1/1995 |
| WO | 03/011864 A1 | 2/2003 |
| WO | 2005/028434 A2 | 3/2005 |
| WO | 2005/028438 A1 | 3/2005 |
| WO | 2006009832 * | 1/2006 |
| WO | 2006/029115 A2 | 3/2006 |
| WO | 2006/084030 A2 | 8/2006 |
| WO | 2006/114180 A1 | 11/2006 |
| WO | 2007075572 A2 | 7/2007 |
| WO | 2008/005937 A2 | 1/2008 |
| WO | 2008/055068 A2 | 5/2008 |

OTHER PUBLICATIONS

Wolf, Manfred E. "Burger's medicinal Chemistry, 5ed, Part I", John Wiley & Sons, 1995, pp. 975-977.*
Banker, G.S. et al., "Modern Pharmaceutics, 3ed.", Marcel Dekker, New York, 1996, pp. 451 and 596.*
Minetti et al., Journal of medicinal Chemistry (2005), 48(22), 6887-6896.*
Barraclough et al., Journal of Medicinal Chemistry 91990), 33(8), pp. 2231-2239.*
Young et al., Journal of Medicial Chemistry (1990), 33(8), pp. 2073-2080.*
Len et al., Trends in Molecular medicine, (2002), vol. 8(4), pp. 55-61.*
Kasibhatla, et. al., "Rationally Designed High-Affinity 2-Amino-6-halopurine Heat Shock Protein 90 Inhibitors That Exhibit Potent Antitumor Activity," J. Med. Chem., 50: 2767-2778 (2007).
Bydillon, et. al, "Multiple-Target Drugs: Inhibitors of Heat Shock Protein 90 and of Histone Deacetylase," Current Drug Targets, 6: 337-351 (2005).
Dymock, B. et. al., "Adenine derived inhibitors of the molecular chaperone HSP9O—SAR explained through multiple X-ray structures," Bioorganic & Medicinal Chemistry Letters, 14: 325-328 (2004).
Chiosis, G., et. al., "A small molecule designed to bind to the adenine nucleotide pocket of Hsp90 causes Her2 degradation and the growth arrest and differentiation of breast cancer cells," Chemistry & Biology, 8: 289-299 (2001).
Llaugher, L, et. al., "Evaluation of 8-Arylsulfanyl, 8-Arylsulfoxyl, and 8-Arylsulfonyl Adenine Derivatives as Inhibitors of the Heat Shock Protein 90," J. Med. Chem., 48: 2892-2905 (2005).
Stebbins, C.E., et. al., "Crystal Structure of an Hsp90—Geldanamycin Complex: Targeting of a Protein Chaperone by an Antitumor Agent," Cell, 89: 239-250 (1997).
Biamonte, Marco A., et al., "Orally Active Purine-Based Inhibitors of the Heat Shock Protein 90," J. Med. Chem., 49: 817-828 (2006).
Kotera, C., et. al., "Synthesis of 3-deaza-3-nitro-2'-deoxyadenosine," Bioorganic & Medicinal Chemistry, 14: 1935-1941 (2006).
Yun, Bo-Geon, et. al., "Novobiocin Induces a Distinct Conformation of Hsp90 and Alters Hsp90-Cochaperone-Client Interactions," Biochemistry, 43: 8217-8229 (2004).
Chiosis, G., et. al., "Development of a Purine-Scaffold Novel Class of Hsp90 Binders that Inhibit the Proliferation of Cancer Cells and Induce the Degradation of Her2 Tyrosine Kinase," Bioorganic & Medicinal Chemistry,10: 3555-3564 (2002).

(Continued)

*Primary Examiner* — Janet Andres
*Assistant Examiner* — Niloofar Rahmani
(74) *Attorney, Agent, or Firm* — Roy P. Issac; Carolyn S. Elmore; Elmore Patent Law Group, P.C.

(57) ABSTRACT

The present invention relates to HSP90 inhibitors containing fused amino pyridine core that are useful as inhibitors of HSP90 and their use in the treatment of HSP90 related diseases and disorders such as cancer, an autoimmune disease, or a neurodegenerative disease.

14 Claims, No Drawings

OTHER PUBLICATIONS

He, H., et. al., "Identification of Potent Water Soluble Purine-Scaffold Inhibitors of the Heat Shock Protein 90," J. Med. Chem., 49, 381-390 (2006).

Hu, H., et al., "Potent 4-amino-5-azaindole factor VIIa inhibitors," Bioorganic & Medicinal Chemistry Letters, 16(17): 4567-4570 (2006).

Temple, C., et al., "Synthesis of Potential Anticancer Agents: Imidazo[4,5-c]pyridines and Imidazo[4,5-b]pyridines," J. Med. Chem., 30(10): 1746-1751 (1987).

Sreedhar, A. S., et al., "Inhibition of Hsp90: a new strategy for inhibiting protein kinases," Biochimica et Biophysica Acta, 1697(1-2): 233-242 (2004).

* cited by examiner

FUSED AMINO PYRIDINE AS HSP90 INHIBITORS

RELATED APPLICATIONS

This application claims the benefit of U.S. Provisional Application No. 60/895,921, filed on Mar. 20, 2007 and U.S. Provisional Application No. 61/015,288, filed on Dec. 20, 2007. The entire teachings of the above applications are incorporated herein by reference.

BACKGROUND OF THE INVENTION

HSP90s are ubiquitous chaperone proteins that are involved in proper protein folding and stabilization of a wide range of proteins, including key proteins involved in signal transduction, cell cycle control and transcriptional regulation. Researchers have reported that HSP90 chaperone proteins are associated with important signaling proteins, such as steroid hormone receptors and protein kinases, including, e.g., Raf-1, EGFR, v-Src family kinases, Cdk4, and ErbB-2, many of which are overexpressed or mutated in various cancers (Buchner J. *TIBS*, 1999, 24, 136 141; Stepanova, L. et al. *Genes Dev.* 1996, 10, 1491 502; Dai, K. et al. *J. Biol. Chem.* 1996, 271, 22030-4). Studies further indicate that certain co-chaperones, e.g., HSP70, p60/Hop/Sti1, Hip, Bag1, HSP40/Hdj2/Hsj1, immunophilins, p23, and p50, may assist HSP90 in its function (Caplan, A. *Trends in Cell Biol.* 1999, 9, 262 68).

HSP90 has been shown by mutational analysis to be necessary for the survival of normal eukaryotic cells. However, HSP90 is over expressed in many tumor types indicating that it may play a significant role in the survival of cancer cells and that cancer cells may be more sensitive to inhibition of HSP90 than normal cells. For example, cancer cells typically have a large number of mutated and overexpressed oncoproteins that are dependent on HSP90 for folding. In addition, because the environment of a tumor is typically hostile due to hypoxia, nutrient deprivation, acidosis, etc., tumor cells may be especially dependent on HSP90 for survival. Moreover, inhibition of HSP90 causes simultaneous inhibition of a number of client oncoproteins, as well as hormone receptors and transcription factors making it an attractive target for an anti-cancer agent. In fact, benzoquinone ansamycins, a family of natural products that inhibit HSP90, has shown evidence of therapeutic activity in clinical trials. Several promising ansamycin related HSP90 inhibitors are currently in clinical trial namely, 17-allylamino 17-demethoxygeldanamycin (17-AAG), 17-dimethylaminoethylamino-17-demethoxygeldanamycin (17-DMAG) and IPI-504. Another class of the HSP90 inhibitor is the synthetic small molecule purine-scaffold. Currently, many of the purine-scaffold HSP90 inhibitors are showing positive preclinical results; with the front runner being CNF-2024, which is currently in phase 1 clinical trial.

Recent studies suggest that heat shock proteins (HSPs) play an important role in neurodegenerative disorders such as Parkinson's disease (PD), Alzheimer's disease (AD), amyotropic lateral sclerosis (ALS), Huntington disease (HD) (Luo, G-R. *Int. J. Biol. Sci.*, 2007, 3(1), 20-26; Dickey, C., *J. Clin. Invest.*, 2007, 117(3), p. 648-658). It has been shown that manipulation of HSPs, such as down regulation of HSP90 or up regulation of HSP70, affords beneficial effects in several neurodegenerative disorders either by reducing protein aggregation or facilitating proper folding of proteins to restore their function.

Drugs targeting the protein HSP90 are quite new in cancer and neurodegenerative disease therapies. Research relating to HSP90 is rapidly developing and therefore, the need for novel and active compounds exists. As such, this invention relates to fused amino pyridine compounds useful as HSP90 inhibitors.

SUMMARY OF THE INVENTION

The present invention relates to HSP90 inhibitors containing fused amino pyridine core that are useful as inhibitors of HSP90 and their use in the treatment of HSP90 related diseases and disorders such as cancer, an autoimmune disease, or a neurodegenerative disease.

Accordingly, the present invention provides a compound having the general formula I:

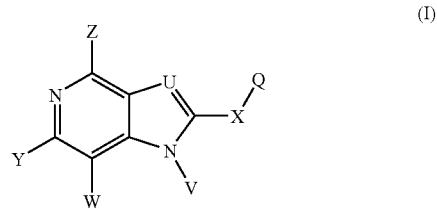

or its geometric isomers, enantiomers, diastereomers, racemates, pharmaceutically acceptable salts, prodrugs and solvates thereof, wherein U is N or CH;

W is hydrogen, halogen, amino, hydroxy, thiol, alkyl, substituted alkyl, substituted or unsubstituted alkoxy, substituted or unsubstituted alkylamino, substituted or unsubstituted dialkylamino, substituted or unsubstituted alkylthio, substituted or unsubstituted alkylsulfonyl, $CF_3$, $NO_2$, CN, $N_3$, sulfonyl, acyl, aryl, substituted aryl, heteroaryl, substituted heteroaryl, heterocyclic, substituted heterocyclic, cycloalkyl, or substituted cycloalkyl;

X is absent, O, S, S(O), $S(O)_2$, $N(R_8)$, C(O), $CF_2$, $C(R_8)$ or $C_2$-$C_6$ alkyl, $C_2$-$C_6$ alkenyl, $C_2$-$C_6$ alkynyl in which one or more methylene can be interrupted or terminated by O, S, SO, $SO_2$, $N(R_8)$, C(O), where $R_8$ is hydrogen, acyl, aliphatic or substituted aliphatic;

Y is independently hydrogen, halogen, $NO_2$, CN, or lower alkyl;

Z is amino, substituted or unsubstituted alkylamino, substituted or unsubstituted dialkylamino, substituted or unsubstituted alkylcarbonylamino;

Q is aryl, substituted aryl, heteroaryl, substituted heteroaryl, cycloalkyl, or heterocycloalkyl;

V is hydrogen, straight- or branched-, substituted or unsubstituted alkyl, substituted or unsubstituted alkenyl, substituted or unsubstituted alkynyl, which one or more methylenes can be interrupted or terminated by O, S, S(O), $SO_2$, $N(R_8)$, C(O), substituted or unsubstituted aryl, substituted or unsubstituted heteroaryl, substituted or unsubstituted heterocyclic; substituted or unsubstituted cycloalkyl; where $R_8$ is hydrogen, acyl, aliphatic or substituted aliphatic.

DETAILED DESCRIPTION OF THE INVENTION

In a first embodiment of the compounds of the present invention are compounds represented by formula (I) as illustrated above, or its geometric isomers, enantiomers, diastereomers, racemates, pharmaceutically acceptable salts, prodrugs and solvates thereof.

In a second embodiment of the compounds of the present invention are compounds represented by formula (II) as illustrated below, or its geometric isomers, enantiomers, diastereomers, racemates, pharmaceutically acceptable salts, prodrugs and solvates thereof:

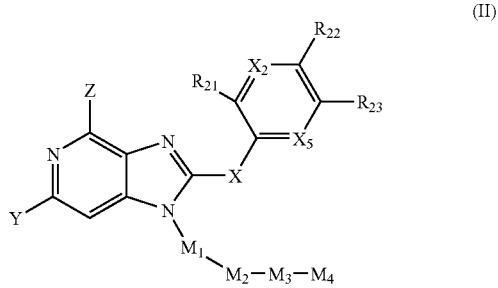

(II)

wherein $X_2$ and $X_5$ are independently $CR_{21}$ or N; $R_{21}$-$R_{23}$ are independently selected from the group consisting of hydrogen, halogen, amino, substituted amino, hydroxy, substituted hydroxy, thiol, substituted thiol, alkyl, substituted alkyl, alkenyl, substituted alkenyl, alkynyl, substituted alkynyl, substituted or unsubstituted alkoxy, substituted or unsubstituted alkylamino, substituted or unsubstituted dialkylamino, substituted or unsubstituted alkylthio, substituted or unsubstituted alkylsulfonyl, $CF_3$, $NO_2$, CN, $N_3$, substituted carbonyl, sulfonyl, acyl, aryl, substituted aryl, heteroaryl, substituted heteroaryl, heterocyclic, substituted heterocyclic, cycloalkyl, or substituted cycloalkyl; $R_{22}$ and $R_{23}$ can be taken together from the carbon to which they are attached to form a saturated or unsaturated fused 5-8 membered cyclic ring optionally substituted with 0-3 heteroatom; $M_1$ is absent, $C_1$-$C_6$ alkyl, $C_2$-$C_6$ alkenyl, $C_2$-$C_6$ alkynyl, aryl or heteroaryl; $M_2$ is absent, O, S, SO, $SO_2$, $N(R_8)$, or C=O; $M_3$ is absent, C=O, O, S, SO, $SO_2$ or $N(R_8)$; $M_4$ is hydrogen, halogen, CN, $N_3$, hydroxy, substituted hydroxy, amino, substituted amino, $CF_3$, $C_1$-$C_6$ alkyl, $C_2$-$C_6$ alkenyl, $C_2$-$C_6$ alkynyl, cycloalkyl, heterocyclic, aryl or heteroaryl; and X, Y and Z are as previously defined.

In one example, $X_2$ and $X_5$ are independently CH or N; $R_{21}$-$R_{23}$ are independently selected from the group consisting of hydrogen, halogen, amino, hydroxy, thiol, alkyl, substituted alkyl, substituted or unsubstituted alkoxy, substituted or unsubstituted alkylamino, substituted or unsubstituted dialkylamino, substituted or unsubstituted alkylthio, substituted or unsubstituted alkylsulfonyl, $CF_3$, $NO_2$, CN, $N_3$, sulfonyl, acyl, aryl, substituted aryl, heteroaryl, substituted heteroaryl, heterocyclic, substituted heterocyclic, cycloalkyl, or substituted cycloalkyl; $R_{22}$ and $R_{23}$ can be taken together from the carbon to which they are attached to form a saturated or unsaturated fused 5-8 membered cyclic ring optionally substituted with 0-3 heteroatom; $M_1$ is absent, $C_1$-$C_6$ alkyl, $C_2$-$C_6$ alkenyl, $C_2$-$C_6$ alkynyl, aryl or heteroaryl; $M_2$ is absent, O, S, SO, $SO_2$, $N(R_8)$, or C=O; $M_3$ is absent, C=O, O, S, SO, $SO_2$ or $N(R_8)$; $M_4$ is hydrogen, halogen, CN, $N_3$, hydroxy, amino, $CF_3$, $C_1$-$C_6$ alkyl, $C_2$-$C_6$ alkenyl, $C_2$-$C_6$ alkynyl, cycloalkyl, heterocyclic, aryl or heteroaryl; and X, Y and Z are as previously defined.

In a third embodiment of the compounds of the present invention are compounds represented by formula (III) as illustrated below, or its geometric isomers, enantiomers, diastereomers, racemates, pharmaceutically acceptable salts, prodrugs and solvates thereof:

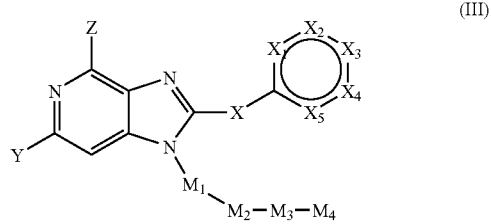

(III)

wherein $X_1$-$X_5$ are independently N or $CR_{21}$, where $R_{21}$ is independently selected from the group consisting of hydrogen, halogen, amino, substituted amino, hydroxy, substituted hydroxy, thiol, substituted thiol, alkyl, substituted alkyl, alkenyl, substituted alkenyl, alkynyl, substituted alkynyl, substituted or unsubstituted alkoxy, substituted or unsubstituted alkylamino, substituted or unsubstituted dialkylamino, substituted or unsubstituted alkylthio, substituted or unsubstituted alkylsulfonyl, $CF_3$, $NO_2$, CN, $N_3$, substituted carbonyl, sulfonyl, acyl, aryl, substituted aryl, heteroaryl, substituted heteroaryl, heterocyclic, substituted heterocyclic, cycloalkyl, or substituted cycloalkyl; $M_1$ is absent, $C_1$-$C_6$ alkyl, $C_2$-$C_6$ alkenyl, $C_2$-$C_6$ alkynyl, aryl or heteroaryl; $M_2$ is absent, O, S, SO, $SO_2$, $N(R_8)$, or C=O; $M_3$ is absent, C=O, O, S, SO, $SO_2$ or $N(R_8)$; $M_4$ is hydrogen, halogen, CN, $N_3$, hydroxy, substituted hydroxy, amino, substituted amino, $CF_3$, $C_1$-$C_6$ alkyl, $C_2$-$C_6$ alkenyl, $C_2$-$C_6$ alkynyl, cycloalkyl, heterocyclic, aryl or heteroaryl; and X, Y and Z are as previously defined. In one example, X is S; Y is hydrogen; Z is amino; $M_1$-$M_4$ and $X_1$-$X_5$ are as defined above.

In one example, $X_1$-$X_5$ are independently N or $CR_{21}$, where $R_{21}$ is independently selected from the group consisting of hydrogen, halogen, amino, hydroxy, thiol, alkyl, substituted alkyl, substituted or unsubstituted alkoxy, substituted or unsubstituted alkylamino, substituted or unsubstituted dialkylamino, substituted or unsubstituted alkylthio, substituted or unsubstituted alkylsulfonyl, $CF_3$, $NO_2$, CN, $N_3$, sulfonyl, acyl, aryl, substituted aryl, heteroaryl, substituted heteroaryl, heterocyclic, substituted heterocyclic, cycloalkyl, or substituted cycloalkyl; $M_1$ is absent, $C_1$-$C_6$ alkyl, $C_2$-$C_6$ alkenyl, $C_2$-$C_6$ alkynyl, aryl or heteroaryl; $M_2$ is absent, O, S, SO, $SO_2$, $N(R_8)$, or C=O; $M_3$ is absent, C=O, O, S, SO, $SO_2$ or $N(R_8)$; $M_4$ is hydrogen, halogen, CN, $N_3$, hydroxy, amino, $CF_3$, $C_1$-$C_6$ alkyl, $C_2$-$C_6$ alkenyl, $C_2$-$C_6$ alkynyl, cycloalkyl, heterocyclic, aryl or heteroaryl; and X, Y and Z are as previously defined. In one example, X is S; Y is hydrogen; Z is amino; $M_1$-$M_4$ and $X_1$-$X_5$ are as defined above.

In a fourth embodiment of the compounds of the present invention are compounds represented by formula (IV) as illustrated below, or its geometric isomers, enantiomers, diastereomers, racemates, pharmaceutically acceptable salts, prodrugs and solvates thereof:

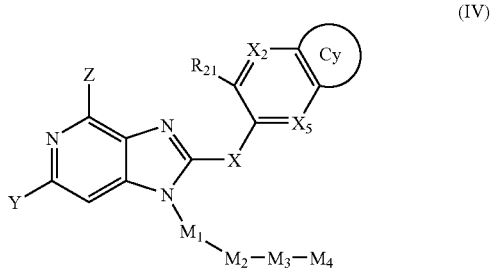

(IV)

wherein $X_2$ and $X_5$ are independently CH or N; $R_{21}$ is independently selected from the group consisting of hydrogen, halogen, amino, substituted amino, hydroxy, substituted hydroxy, thiol, substituted thiol, alkyl, substituted alkyl, alkenyl, substituted alkenyl, alkynyl, substituted alkynyl, substituted or unsubstituted alkoxy, substituted or unsubstituted alkylamino, substituted or unsubstituted dialkylamino, substituted or unsubstituted alkylthio, substituted or unsubstituted alkylsulfonyl, $CF_3$, $NO_2$, CN, $N_3$, substituted carbonyl, sulfonyl, acyl, aryl, substituted aryl, heteroaryl, substituted heteroaryl, heterocyclic, substituted heterocyclic, cycloalkyl, or substituted cycloalkyl; Cy is a saturated or unsaturated fused 5-8 membered cyclic ring optionally substituted with 0-3 heteroatom; $M_1$ is absent, $C_1$-$C_6$ alkyl, $C_2$-$C_6$ alkenyl, $C_2$-$C_6$ alkynyl, aryl or heteroaryl; $M_2$ is absent, O, S, SO, $SO_2$, $N(R_8)$, or C=O; $M_3$ is absent, C=O, O, S, SO, $SO_2$ or $N(R_8)$; $M_4$ is hydrogen, halogen, CN, $N_3$, hydroxy, substituted hydroxy, amino, substituted amino, $CF_3$, $C_1$-$C_6$ alkyl, $C_2$-$C_6$ alkenyl, $C_2$-$C_6$ alkynyl, cycloalkyl, heterocyclic, aryl or heteroaryl; and X, Y and Z are as previously defined. In one example, X is S; Y is hydrogen; Z is amino; $R_{21}$, $M_1$-$M_4$ and $X_2$, $X_5$ are as defined above.

In one example, $X_2$ and $X_5$ are independently CH or N; $R_{21}$ is independently selected from the group consisting of hydrogen, halogen, amino, hydroxy, thiol, alkyl, substituted alkyl, substituted or unsubstituted alkoxy, substituted or unsubstituted alkylamino, substituted or unsubstituted dialkylamino, substituted or unsubstituted alkylthio, substituted or unsubstituted alkylsulfonyl, $CF_3$, $NO_2$, CN, $N_3$, sulfonyl, acyl, aryl, substituted aryl, heteroaryl, substituted heteroaryl, heterocyclic, substituted heterocyclic, cycloalkyl, or substituted cycloalkyl; Cy is a saturated or unsaturated fused 5-8 membered cyclic ring optionally substituted with 0-3 heteroatom; $M_1$ is absent, $C_1$-$C_6$ alkyl, $C_2$-$C_6$ alkenyl, $C_2$-$C_6$ alkynyl, aryl or heteroaryl; $M_2$ is absent, O, S, SO, $SO_2$, $N(R_8)$, or C=O; $M_3$ is absent, C=O, O, S, SO, $SO_2$ or $N(R_8)$; $M_4$ is hydrogen, halogen, CN, $N_3$, hydroxy, amino, $CF_3$, $C_1$-$C_6$ alkyl, $C_2$-$C_6$ alkenyl, $C_2$-$C_6$ alkynyl, cycloalkyl, heterocyclic, aryl or heteroaryl; and X, Y and Z are as previously defined. In one example, X is S; Y is hydrogen; Z is amino; $R_{21}$, $M_1$-$M_4$ and $X_2$, $X_5$ are as defined above.

In a fifth embodiment of the compounds of the present invention are compounds represented by formula (V) as illustrated below, or its geometric isomers, enantiomers, diastereomers, racemates, pharmaceutically acceptable salts, prodrugs and solvates thereof:

(V)

wherein $X_2$ and $X_5$ are independently CH or N; $R_{21}$ is independently selected from the group consisting of hydrogen, halogen, amino, substituted amino, hydroxy, substituted hydroxy, thiol, substituted thiol, alkyl, substituted alkyl, alkenyl, substituted alkenyl, alkynyl, substituted alkynyl, substituted or unsubstituted alkoxy, substituted or unsubstituted alkylamino, substituted or unsubstituted dialkylamino, substituted or unsubstituted alkylthio, substituted or unsubstituted alkylsulfonyl, $CF_3$, $NO_2$, CN, $N_3$, substituted carbonyl, sulfonyl, acyl, aryl, substituted aryl, heteroaryl, substituted heteroaryl, heterocyclic, substituted heterocyclic, cycloalkyl, or substituted cycloalkyl; $Y_1$ and $Y_3$ are independently O, S, $N(R_8)$, $CH(R_{21})$; n is 1, 2, or 3; $M_1$ is absent, $C_1$-$C_6$ alkyl, $C_2$-$C_6$ alkenyl, $C_2$-$C_6$ alkynyl, aryl or heteroaryl; $M_2$ is absent, O, S, SO, $SO_2$, $N(R_8)$, or C=O; $M_3$ is absent, C=O, O, S, SO, $SO_2$ or $N(R_8)$; $M_4$ is hydrogen, halogen CN, $N_3$, hydroxy, substituted hydroxy, amino, substituted amino, $CF_3$, $C_1$-$C_6$ alkyl, $C_2$-$C_6$ alkenyl, $C_2$-$C_6$ alkynyl, cycloalkyl, heterocyclic, aryl or heteroaryl; $R_{10}$ and $R_{20}$ are independently hydrogen, alkyl, substituted alkyl, aryl or substituted aryl; and X, Y and Z are as previously defined. In one example, X is S; Y is hydrogen; Z is amino; n, $R_{21}$, $M_1$-$M_4$, $X_2$, $X_5$, $Y_1$ and $Y_3$ are as defined above.

In one example, $X_2$ and $X_5$ are independently CH or N; $R_{21}$ is independently selected from the group consisting of hydrogen, halogen, amino, hydroxy, thiol, alkyl, substituted alkyl, substituted or unsubstituted alkoxy, substituted or unsubstituted alkylamino, substituted or unsubstituted dialkylamino, substituted or unsubstituted alkylthio, substituted or unsubstituted alkylsulfonyl, $CF_3$, $NO_2$, CN, $N_3$, sulfonyl, acyl, aryl, substituted aryl, heteroaryl, substituted heteroaryl, heterocyclic, substituted heterocyclic, cycloalkyl, or substituted cycloalkyl; $Y_1$ and $Y_3$ are independently O, S, $N(R_8)$, $CH(R_{21})$; n is 1, 2, or 3; $M_1$ is absent, $C_1$-$C_6$ alkyl, $C_2$-$C_6$ alkenyl, $C_2$-$C_6$ alkynyl, aryl or heteroaryl; $M_2$ is absent, O, S, SO, $SO_2$, $N(R_8)$, or C=O; $M_3$ is absent, C=O, O, S, SO, $SO_2$ or $N(R_8)$; $M_4$ is hydrogen, halogen, CN, $N_3$, hydroxy, amino, $CF_3$, $C_1$-$C_6$ alkyl, $C_2$-$C_6$ alkenyl, $C_2$-$C_6$ alkynyl, cycloalkyl, heterocyclic, aryl or heteroaryl; $R_{10}$ and $R_{20}$ are independently hydrogen, alkyl, substituted alkyl, aryl or substituted aryl; and X, Y and Z are as previously defined. In one example, X is S; Y is hydrogen; Z is amino; n, $R_{21}$, $M_1$-$M_4$, $X_2$, $X_5$, $Y_1$ and $Y_3$ are as defined above.

Representative compounds according to the invention are those selected from the Table A below or its geometric isomers, enantiomers, diastereomers, racemates, pharmaceutically acceptable salts, prodrugs and solvates thereof:

TABLE A

| Compound # | Structure |
| --- | --- |
| 1 | 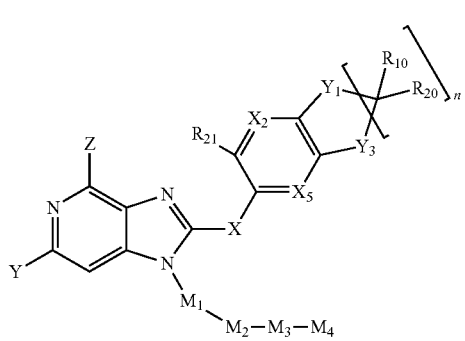 |

TABLE A-continued

| Compound # | Structure |
|---|---|
| 2 | (4-amino-imidazo[4,5-c]pyridine, 2-S-(6-chloro-1,3-benzodioxol-5-yl), 1-(pent-4-ynyl)) |
| 3 | (4-amino-imidazo[4,5-c]pyridine, 2-S-(6-iodo-1,3-benzodioxol-5-yl), 1-(pent-4-ynyl)) |
| 4 | (4-amino-imidazo[4,5-c]pyridine, 2-S-(6-iodo-1,3-benzodioxol-5-yl), 1-pentyl) |
| 5 | (4-amino-imidazo[4,5-c]pyridine, 2-S-(7-bromo-2,3-dihydro-1,4-benzodioxin-6-yl), 1-(pent-4-ynyl)) |
| 6 | (4-amino-imidazo[4,5-c]pyridine, 2-S-(7-chloro-2,3-dihydro-1,4-benzodioxin-6-yl), 1-(pent-4-ynyl)) |
| 7 | (4-amino-imidazo[4,5-c]pyridine, 2-S-(7-iodo-2,3-dihydro-1,4-benzodioxin-6-yl), 1-(pent-4-ynyl)) |
| 8 | (4-amino-imidazo[4,5-c]pyridine, 2-S-(7-iodo-2,3-dihydro-1,4-benzodioxin-6-yl), 1-pentyl) |
| 9 | (4-amino-imidazo[4,5-c]pyridine, 2-S-(2,3-dihydrobenzofuran-5-yl), 1-(pent-4-ynyl)) |

TABLE A-continued

| Compound # | Structure |
|---|---|
| 10 | 4-amino-2-(benzofuran-5-ylthio)-1-(pent-4-yn-1-yl)-1H-imidazo[4,5-c]pyridine |
| 11 | 4-amino-2-((3-methoxyphenyl)thio)-1-(pent-4-yn-1-yl)-1H-imidazo[4,5-c]pyridine |
| 12 | 4-amino-2-((2-iodo-5-methoxyphenyl)thio)-1-(pent-4-yn-1-yl)-1H-imidazo[4,5-c]pyridine |
| 13 | 4-amino-2-((2-bromo-5-methoxyphenyl)thio)-1-(pent-4-yn-1-yl)-1H-imidazo[4,5-c]pyridine |
| 14 | 4-amino-2-((2-chloro-5-methoxyphenyl)thio)-1-(pent-4-yn-1-yl)-1H-imidazo[4,5-c]pyridine |
| 15 | 4-amino-2-((2-iodo-4,5-dimethoxyphenyl)thio)-1-(pent-4-yn-1-yl)-1H-imidazo[4,5-c]pyridine |
| 16 | 4-amino-2-((2-iodo-4,5-dihydroxyphenyl)thio)-1-(pent-4-yn-1-yl)-1H-imidazo[4,5-c]pyridine |
| 17 | 4-amino-2-((5-methoxy-2-nitrophenyl)thio)-1-(pent-4-yn-1-yl)-1H-imidazo[4,5-c]pyridine |
| 18 | 4-amino-2-((2-cyano-5-methoxyphenyl)thio)-1-(pent-4-yn-1-yl)-1H-imidazo[4,5-c]pyridine |
| 19 | 4-amino-2-((2-acetyl-5-methoxyphenyl)thio)-1-(pent-4-yn-1-yl)-1H-imidazo[4,5-c]pyridine |

(Structures shown as chemical diagrams in original.)

TABLE A-continued
| Compound # | Structure |
|---|---|
| 20 | 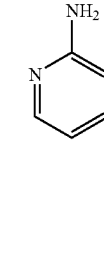 |
| 21 | 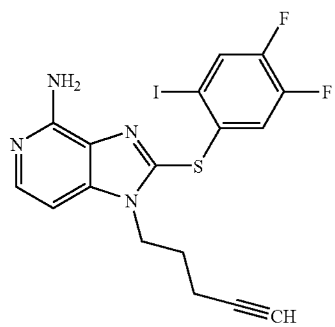 |
| 22 | 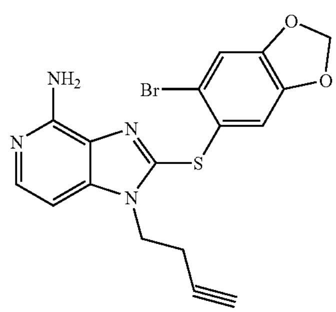 |
| 23 | 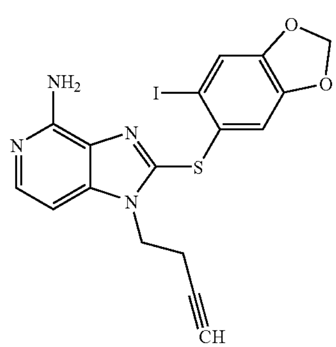 |
| 24 | 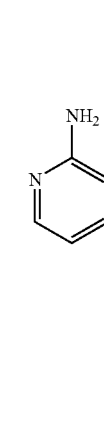 |
| 25 | |
| 26 | |
| 27 | |

TABLE A-continued

| Compound # | Structure |
|---|---|
| 28 | 4-amino-2-[(6-iodo-1,3-benzodioxol-5-yl)thio]-1-(2-cyanoethyl)-imidazo[4,5-c]pyridine |
| 29 | 4-amino-2-[(6-bromo-1,3-benzodioxol-5-yl)thio]-1-(4-cyanobutyl)-imidazo[4,5-c]pyridine |
| 30 | 4-amino-2-[(6-iodo-1,3-benzodioxol-5-yl)thio]-1-(5-cyanopentyl)-imidazo[4,5-c]pyridine |
| 31 | 4-amino-2-[(6-bromo-1,3-benzodioxol-5-yl)thio]-1-(2-aminoethyl)-imidazo[4,5-c]pyridine |
| 32 | 4-amino-2-[(6-iodo-1,3-benzodioxol-5-yl)thio]-1-(2-aminoethyl)-imidazo[4,5-c]pyridine |
| 33 | 4-amino-2-[(6-bromo-1,3-benzodioxol-5-yl)thio]-1-[2-(neopentylamino)ethyl]-imidazo[4,5-c]pyridine |
| 34 | 4-amino-2-[(6-iodo-1,3-benzodioxol-5-yl)thio]-1-[2-(neopentylamino)ethyl]-imidazo[4,5-c]pyridine |
| 35 | 4-amino-2-[(6-chloro-1,3-benzodioxol-5-yl)thio]-1-[2-(neopentylamino)ethyl]-imidazo[4,5-c]pyridine |

TABLE A-continued
| Compound # | Structure |
|---|---|
| 36 | 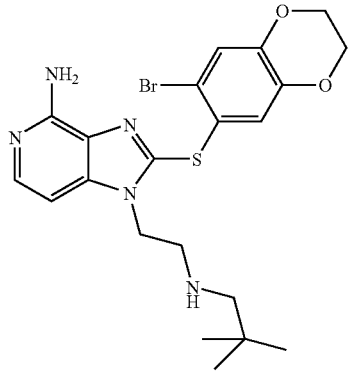 |
| 37 | 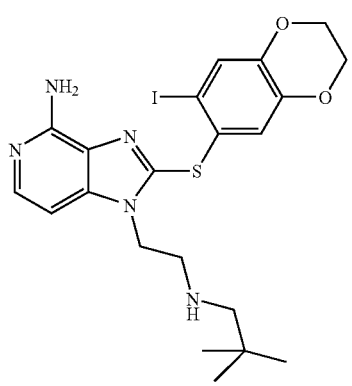 |
| 38 | 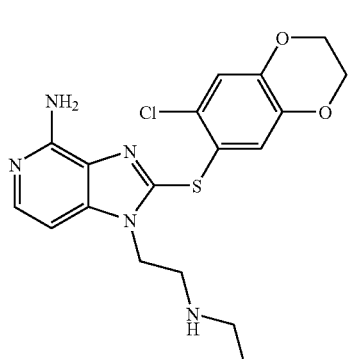 |
| 39 | 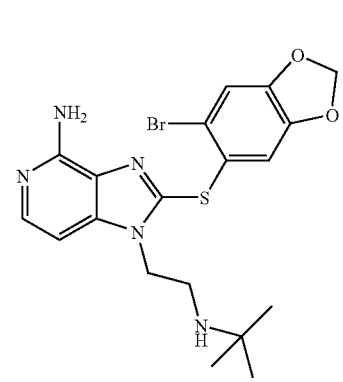 |
| 40 | 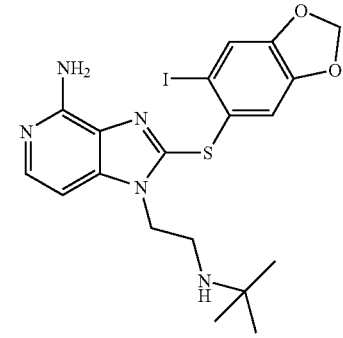 |
| 41 | 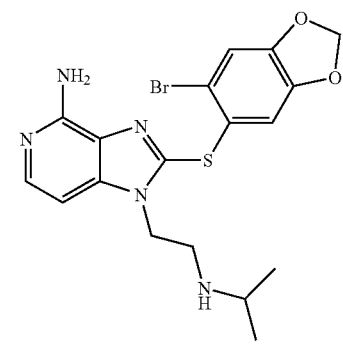 |
| 42 | 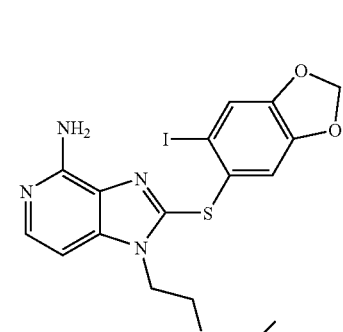 |
| 43 | 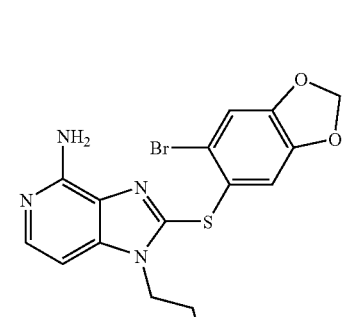 |

TABLE A-continued
| Compound # | Structure |
|---|---|
| 44 | 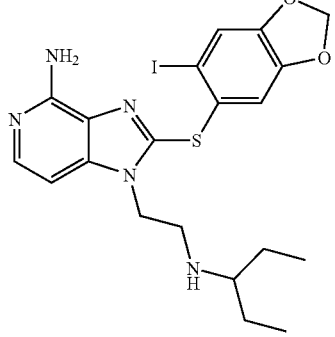 |
| 45 | 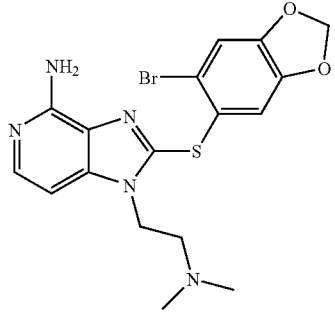 |
| 46 | 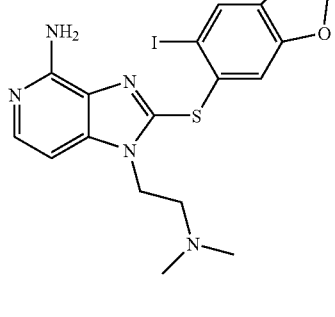 |
| 47 | 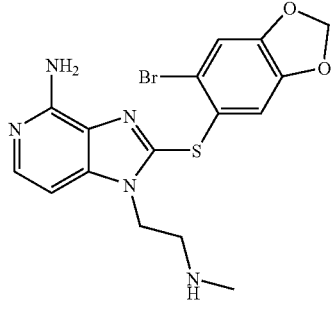 |
| 48 | 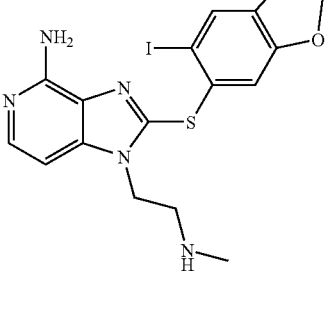 |
| 49 | 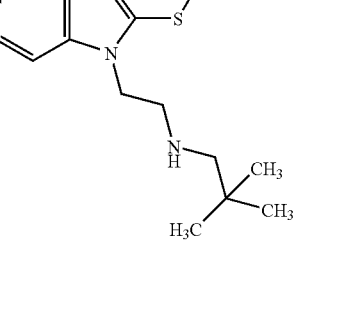 |
| 50 | 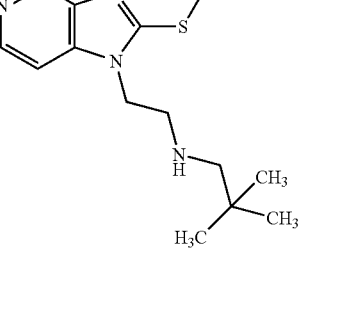 |
| 51 | 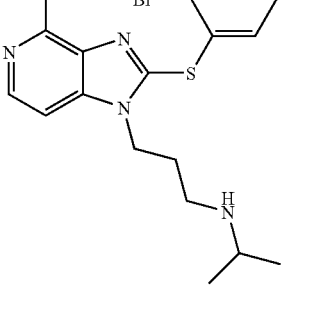 |

TABLE A-continued

| Compound # | Structure |
|---|---|
| 52 | 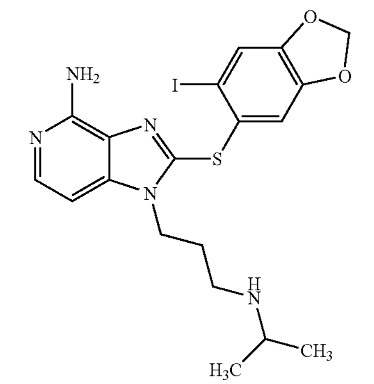 |
| 53 | 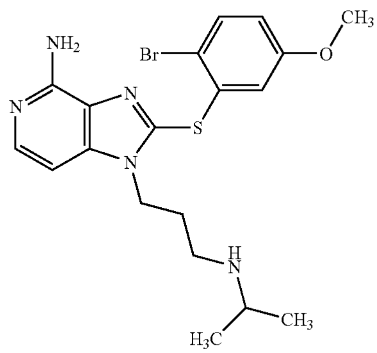 |
| 54 | 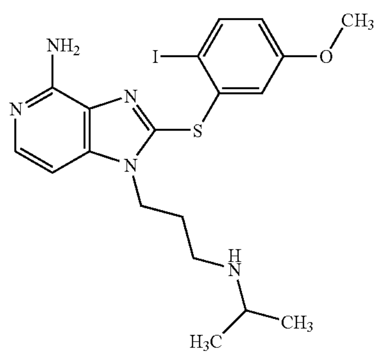 |
| 55 | 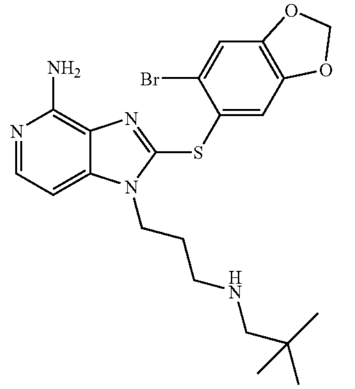 |
| 56 | |
| 57 | |
| 58 | |
| 59 | |

TABLE A-continued

| Compound # | Structure |
|---|---|
| 60 | 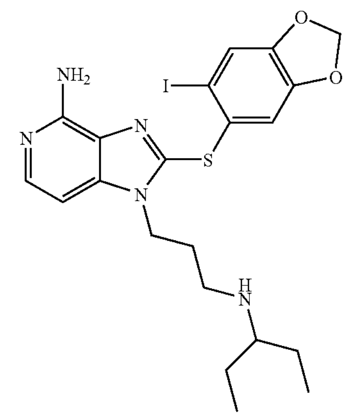 |
| 61 | 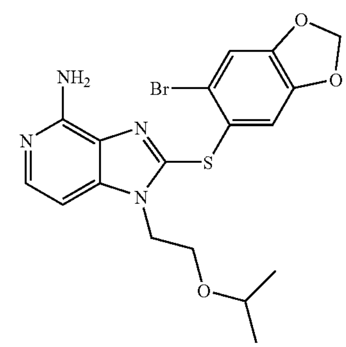 |
| 62 | 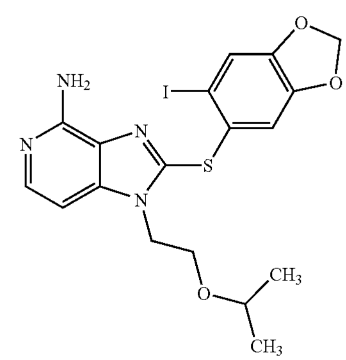 |
| 63 | 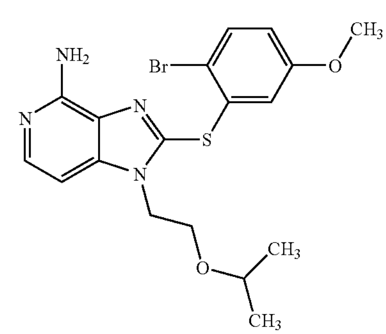 |
| 64 | |
| 65 | |
| 66 | |
| 67 | |

TABLE A-continued

| Compound # | Structure |
|---|---|
| 68 | 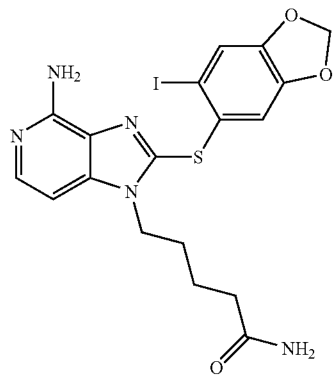 |
| 69 | 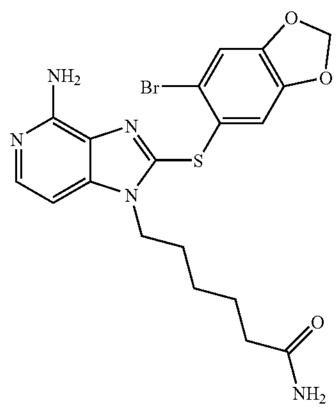 |
| 70 | 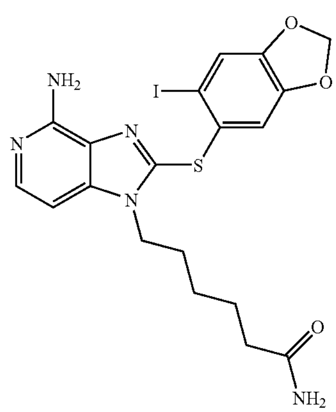 |
| 71 | 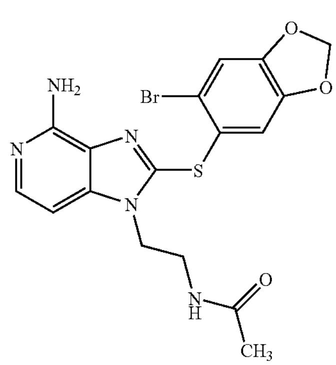 |
| 72 | 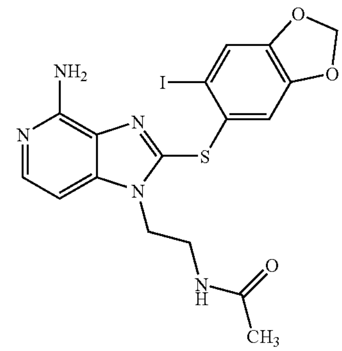 |
| 73 | 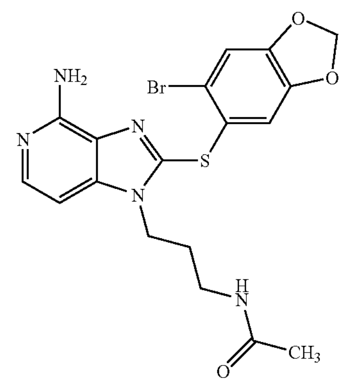 |
| 74 | 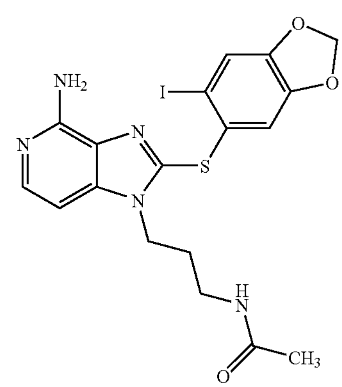 |
| 75 | 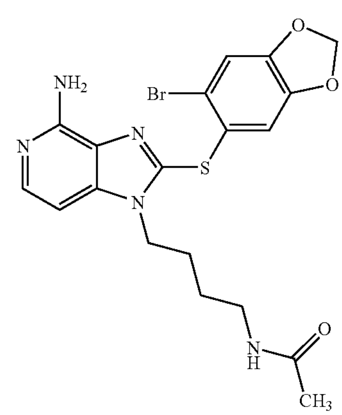 |

TABLE A-continued

| Compound # | Structure |
|---|---|
| 76 | 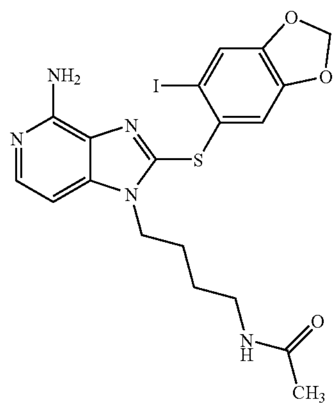 |
| 77 | 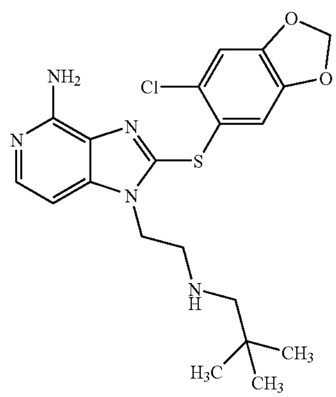 |
| 78 | 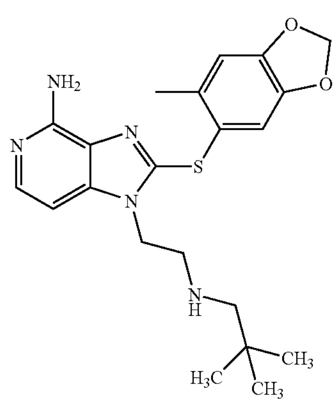 |
| 79 | 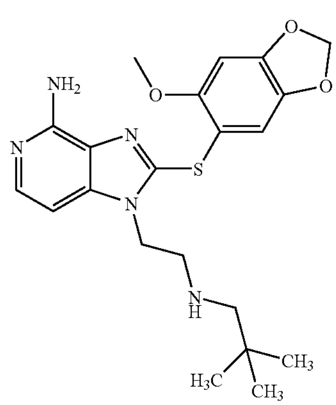 |
| 80 | |
| 81 | |
| 82 | |
| 83 | |

TABLE A-continued

| Compound # | Structure |
|---|---|
| 84 | (structure) |
| 85 | (structure) |
| 86 | (structure) |
| 87 | (structure) |
| 88 | (structure) |
| 89 | (structure) |
| 90 | (structure) |
| 91 | (structure) |

TABLE A-continued

| Compound # | Structure |
|---|---|
| 92 | 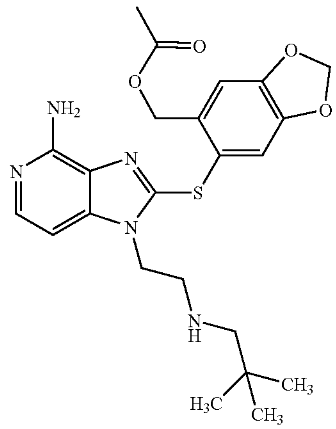 |
| 93 | 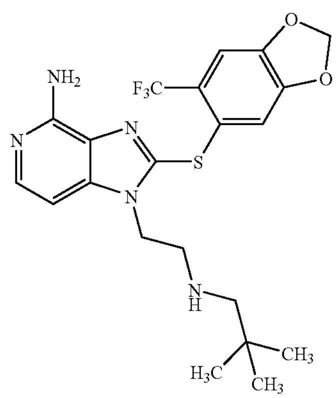 |
| 94 | 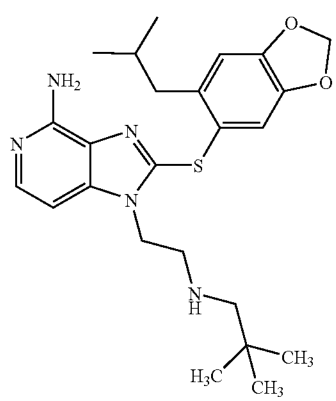 |
| 95 | 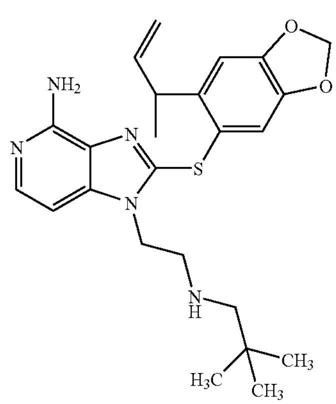 |
| 96 | 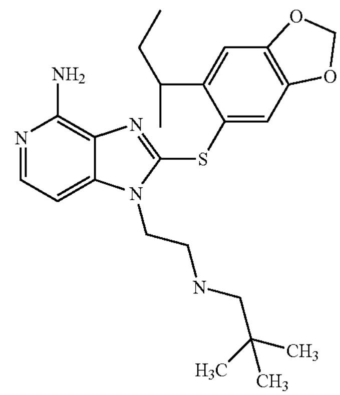 |
| 97 | 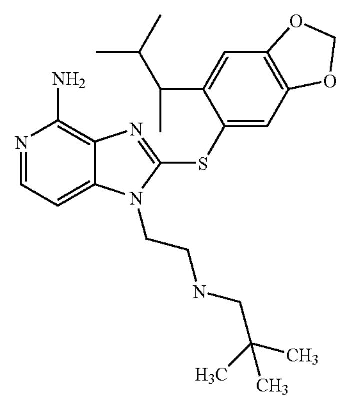 |
| 98 | 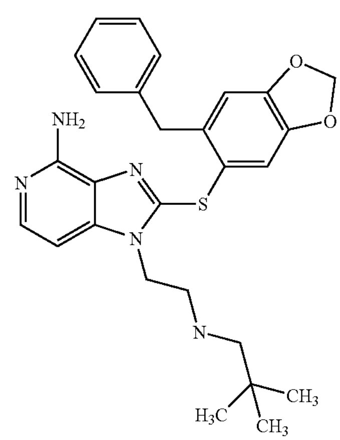 |

TABLE A-continued

| Compound # | Structure |
|---|---|
| 99 | (structure) |
| 100 | (structure) |
| 101 | (structure) |
| 102 | (structure) |
| 103 | (structure) |
| 104 | (structure) |
| 105 | (structure) |

TABLE A-continued

| Compound # | Structure |
|---|---|
| 106 | 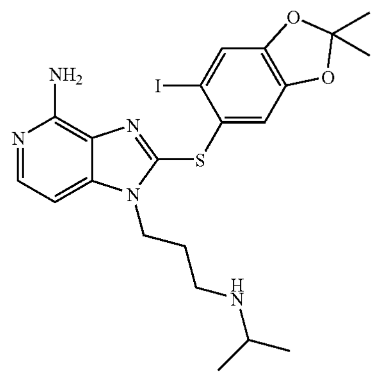 |
| 107 | 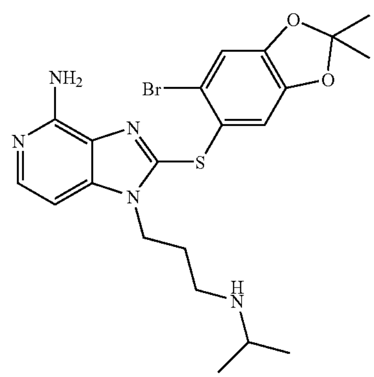 |
| 108 | 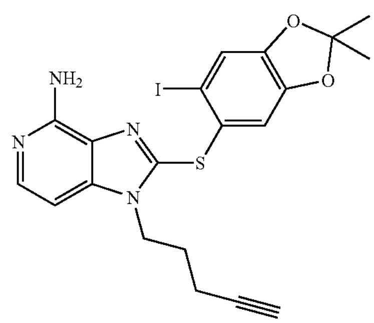 |
| 109 | 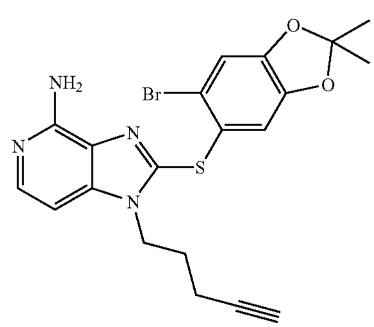 |
| 110 | 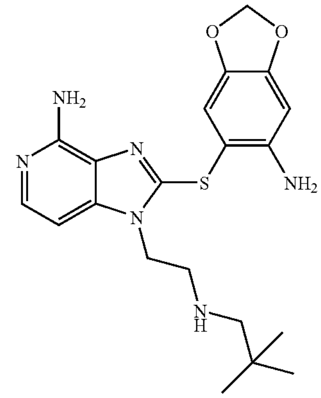 |
| 111 | 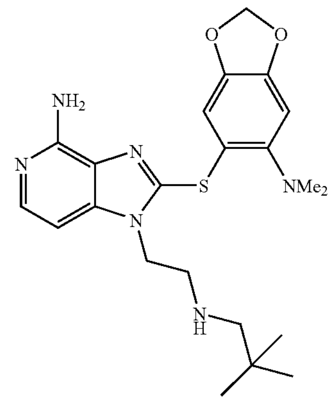 |
| 112 | 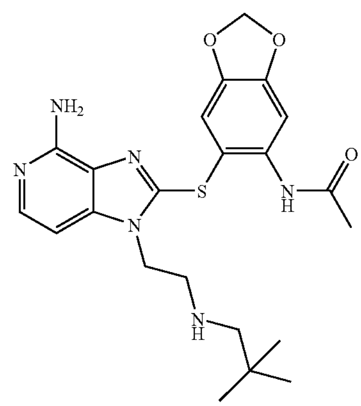 |
| 113 | 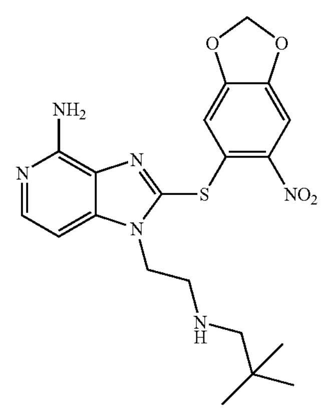 |

TABLE A-continued

| Compound # | Structure |
|---|---|
| 114 | |
| 115 | |
| 116 | |
| 117 | 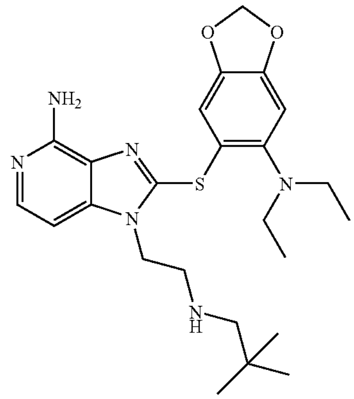 |
| 118 | 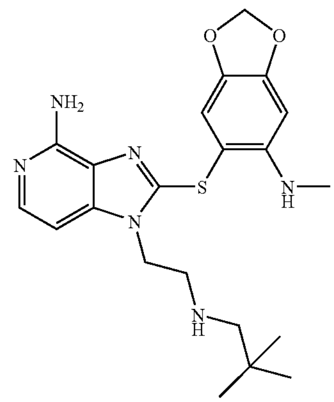 |
| 119 | 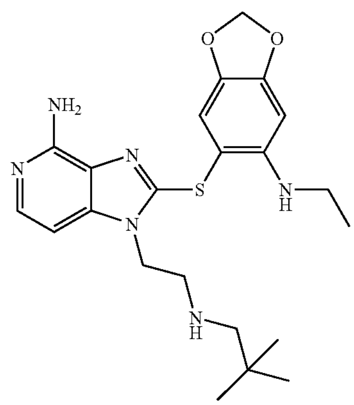 |
| 120 | 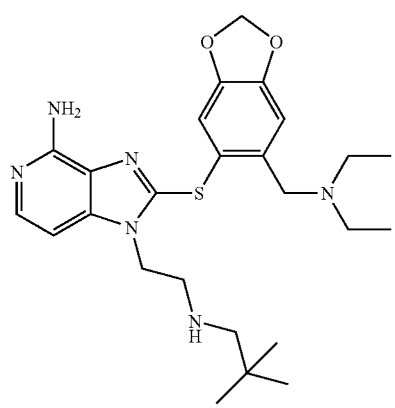 |

TABLE A-continued

| Compound # | Structure |
|---|---|
| 121 | |
| 122 | |
| 123 | |
| 124 | 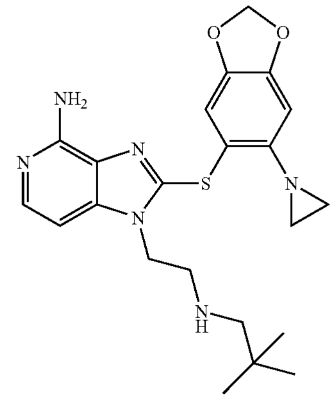 |
| 125 | 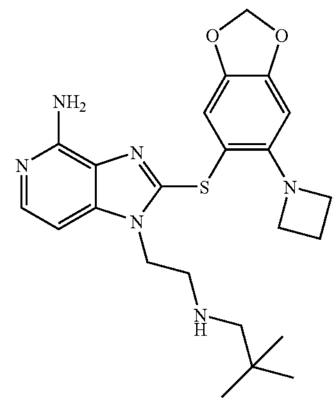 |
| 126 | 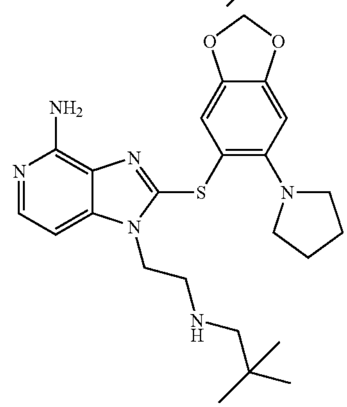 |
| 127 | 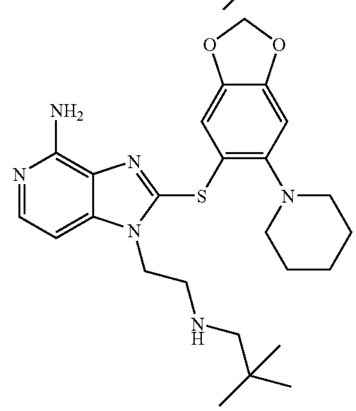 |

The invention further provides methods for the prevention or treatment of diseases or conditions involving aberrant proliferation, differentiation or survival of cells. In one embodiment, the invention further provides for the use of one or more compounds of the invention in the manufacture of a medicament for halting or decreasing diseases involving aberrant proliferation, differentiation, or survival of cells. In preferred embodiments, the disease is cancer or neurodegenerative. In one embodiment, the invention relates to a method of treating cancer in a subject in need of treatment comprising administering to said subject a therapeutically effective amount of a compound of the invention. In one embodiment, the invention relates to a method of treating a neurodegenerative disease in a subject in need of treating comprising administering to said subject a therapeutically effective amount of the compound of the invention.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute nonlymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genito urinary cancers (e.g., prostate, bladder, renal, uterine, ovarian, testicular), lung cancer (e.g., small-cell and non small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the invention, the present invention provides for the use of one or more compounds of the invention in the manufacture of a medicament for the treatment of cancer.

In one embodiment, the present invention includes the use of one or more compounds of the invention in the manufacture of a medicament that prevents further aberrant proliferation, differentiation, or survival of cells. For example, compounds of the invention may be useful in preventing tumors from increasing in size or from reaching a metastatic state. The subject compounds may be administered to halt the progression or advancement of cancer. In addition, the instant invention includes use of the subject compounds to prevent a recurrence of cancer.

This invention further embraces the treatment or prevention of cell proliferative disorders such as hyperplasias, dysplasias and pre-cancerous lesions. Dysplasia is the earliest form of pre-cancerous lesion recognizable in a biopsy by a pathologist. The subject compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intra-epithelial tissue.

"Combination therapy" includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

In one aspect of the invention, the subject compounds may be administered in combination with one or more separate agents that modulate protein kinases involved in various disease states. Examples of such kinases may include, but are not limited to: serine/threonine specific kinases, receptor tyrosine specific kinases and non-receptor tyrosine specific kinases. Serine/threonine kinases include mitogen activated protein kinases (MAPK), meiosis specific kinase (MEK), RAF and aurora kinase. Examples of receptor kinase families include epidermal growth factor receptor (EGFR) (e.g. HER2/neu, HER3, HER4, ErbB, ErbB2, ErbB3, ErbB4, Xmrk, DER, Let23); fibroblast growth factor (FGF) receptor (e.g. FGF-R1, GFF-R2/BEK/CEK3, FGF-R3/CEK2, FGF-R4/TKF, KGF-R); hepatocyte growth/scatter factor receptor (HGFR) (e.g, MET, RON, SEA, SEX); insulin receptor (e.g. IGFI-R); Eph (e.g. CEK5, CEK8, EBK, ECK, EEK, EHK-1, EHK-2, ELK, EPH, ERK, HEK, MDK2, MDK5, SEK); Axl (e.g. Mer/Nyk, Rse); RET; and platelet-derived growth factor receptor (PDGFR) (e.g. PDGFα-R, PDGFβ-R, CSF1-R/FMS, SCF-R/C-KIT, VEGF-R/FLT, NEK/FLK1, FLT3/FLK2/STK-1). Non-receptor tyrosine kinase families include, but are not limited to, BCR-ABL (e.g. p43$^{abl}$, ARG); BTK (e.g. ITK/EMT, TEC); CSK, FAK, FPS, JAK, SRC, BMX, FER, CDK and SYK.

In another aspect of the invention, the subject compounds may be administered in combination with one or more separate agents that modulate non-kinase biological targets or processes. Such targets include histone deacetylases (HDAC), DNA methyltransferase (DNMT), heat shock proteins (e.g. HSP90), and proteosomes.

In a preferred embodiment, subject compounds may be combined with antineoplastic agents (e.g. small molecules, monoclonal antibodies, antisense RNA, and fusion proteins) that inhibit one or more biological targets such as Zolinza, Tarceva, Iressa, Tykerb, Gleevec, Sutent, Sprycel, Nexavar, Sorafinib, CNF2024, RG108, BMS387032, Affinitak, Avastin, Herceptin, Erbitux, AG24322, PD325901, ZD6474, PD184322, Obatodax, ABT737 and AEE788. Such combinations may enhance therapeutic efficacy over efficacy achieved by any of the agents alone and may prevent or delay the appearance of resistant mutational variants.

In certain preferred embodiments, the compounds of the invention are administered in combination with a chemotherapeutic agent. Chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as mustard gas derivatives (Mechlorethamine, cylophosphamide, chlorambucil, melphalan, ifosfamide), ethylenimines (thiotepa, hexamethylmelanine), Alkylsulfonates (Busulfan), Hydrazines and Triazines (Altretamine, Procarbazine, Dacarbazine and Temozolomide), Nitrosoureas (Carmustine, Lomustine and Streptozocin), Ifosfamide and metal salts (Carboplatin, Cisplatin, and Oxaliplatin); plant alkaloids such as Podophyllotoxins (Etoposide and Tenisopide), Taxanes (Paclitaxel and Docetaxel), Vinca alkaloids (Vincristine, Vinblastine, Vindesine and Vinorelbine), and Camptothecan analogs (Irinotecan and Topotecan); anti-tumor antibiotics such as Chromomycins (Dactinomycin and Plicamycin), Anthracyclines (Doxorubicin, Daunorubicin, Epirubicin, Mitoxantrone, Valrubicin and Idarubicin), and miscellaneous antibiotics such as Mitomycin, Actinomycin and Bleomycin; anti-metabolites such as folic acid antagonists (Methotrexate, Pemetrexed, Raltitrexed, Aminopterin), pyrimidine antagonists (5-Fluorouracil, Floxuridine, Cytarabine, Capecitabine, and Gemcitabine), purine antagonists (6-Mercaptopurine and 6-Thioguanine) and adenosine deaminase inhibitors (Cladribine, Fludarabine, Mercaptopurine, Clofarabine, Thioguanine, Nelarabine and Pentostatin); topoisomerase inhibitors such as topoisomerase I inhibitors (Ironotecan, topotecan) and topoisomerase II inhibitors (Amsacrine, etoposide, etoposide phosphate, teniposide); monoclonal antibodies (Alemtuzumab, Gemtuzumab ozogamicin, Rituximab, Trastuzumab, Ibritumomab Tioxetan, Cetuximab, Panitumumab, Tositumomab, Bevacizumab); and miscellaneous anti-neoplastics such as ribonucleotide reductase inhibitors (Hydroxyurea); adrenocortical steroid inhibitor (Mitotane); enzymes (Asparaginase and Pegaspargase); anti-microtubule agents (Estramustine); and retinoids (Bexarotene, Isotretinoin, Tretinoin (ATRA).

In certain preferred embodiments, the compounds of the invention are administered in combination with a chemoprotective agent. Chemoprotective agents act to protect the body or minimize the side effects of chemotherapy. Examples of such agents include, but are not limited to, amfostine, mesna, and dexrazoxane.

In one aspect of the invention, the subject compounds are administered in combination with radiation therapy. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

It will be appreciated that compound of the inventions can be useful in treating disorders such as, but not limited to: Anti-proliferative disorders (e.g. cancers); Neurodegenerative diseases including Huntington's disease, Polyglutamine disease, Parkinson's disease, Alzheimer's disease, Seizures, Striatonigral degeneration, Progressive supranuclear palsy, Torsion dystonia, Spasmodic torticollis and dyskinesis, Familial tremor, Gilles de la Tourette syndrome, Diffuse Lewy body disease, Progressive supranuclear palsy, Pick's disease, intracerebral hemorrhage, Primary lateral sclerosis, Spinal muscular atrophy, Amyotrophic lateral sclerosis, Hypertrophic interstitial polyneuropathy, Retinitis pigmentosa, Hereditary optic atrophy, Hereditary spastic paraplegia, Progressive ataxia and Shy-Drager syndrome; Metabolic diseases including Type 2 diabetes; Degenerative diseases of the Eye including Glaucoma, Age-related macular degeneration, Rubeotic glaucoma; Inflammatory diseases and/or Immune system disorders including Rheumatoid Arthritis (RA), Osteoarthritis, Juvenile chronic arthritis, Graft versus Host disease, Psoriasis, Asthma, Spondyloarthropathy, psoriasis, Crohn's Disease, inflammatory bowel disease Colitis Ulcerosa, Alcoholic hepatitis, Diabetes, Sjoegrens's syndrome, Multiple Sclerosis, Ankylosing spondylitis, Membranous glomerulopathy, Discogenic pain, Systemic Lupus Erythematosus; Disease involving angiogenesis including cancer, psoriasis, rheumatoid arthritis; Psychological disorders including bipolar disease, schizophrenia, mania, depression and dementia; Cardiovascular Diseases including the prevention and treatment of ischemia-related or reperfusion-related vascular and myocardial tissue damage, heart failure, restenosis and arteriosclerosis; Fibrotic diseases including liver fibrosis, cystic fibrosis and angiofibroma; Infectious diseases including Fungal infections, such as candidiasis or Candida Albicans, Bacterial infections, Viral infections, such as Herpes Simplex, poliovirus, rhinovirus and coxsackievirus, Protozoal infections, such as Malaria, Leishmania infection, Trypanosoma brucei infection, Toxoplasmosis and coccidlosis and Haematopoietic disorders including thalassemia, anemia and sickle cell anemia.

In one embodiment, compounds of the invention can be used to induce or inhibit apoptosis, a physiological cell death process critical for normal development and homeostasis. Alterations of apoptotic pathways contribute to the pathogenesis of a variety of human diseases. Compounds of the invention, as modulators of apoptosis, will be useful in the treatment of a variety of human diseases with aberrations in apoptosis including cancer (particularly, but not limited to, follicular lymphomas, carcinomas with p53 mutations, hormone dependent tumors of the breast, prostate and ovary, and precancerous lesions such as familial adenomatous polyposis), viral infections (including, but not limited to, herpesvirus, poxvirus, Epstein-Barr virus, Sindbis virus and adenovirus), autoimmune diseases (including, but not limited to, systemic lupus, erythematosus, immune mediated glomerulonephritis, rheumatoid arthritis, psoriasis, inflammatory bowel diseases, and autoimmune diabetes mellitus), neurodegenerative disorders (including, but not limited to, Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including, but not limited to, chronic anemia and aplastic anemia), degenerative diseases of the musculoskeletal system (including, but not limited to, osteoporosis and arthritis), aspirin-sensitive rhinosinusitis, cystic fibrosis, multiple sclerosis, kidney diseases, and cancer pain.

In addition to anti-cancer and antitumorigenic activity, HSP90 inhibitors have also been implicated in a wide variety of other utilities, including use as anti-inflammation agents, anti-infectious disease agents, agents for treating autoimmunity, agents for treating stroke, ischemia, multiple sclerosis, cardiac disorders, central nervous system related disorders and agents useful in promoting nerve regeneration (See, e.g., Rosen et al. WO 02/09696 (PCT/US01/23640); Degranco et al. WO 99/51223 (PCT/US99/07242); Gold, U.S. Pat. No. 6,210,974 B1; DeFranco et al., U.S. Pat. No. 6,174,875). There are reports in the literature that fibrogenetic disorders including but not limited to scleroderma, polymyositis, systemic lupus, rheumatoid arthritis, liver cirrhosis, keloid formation, interstitial nephritis, and pulmonary fibrosis also may be treatable with HSP90 inhibitors.

In one aspect, the invention provides the use of compounds of the invention for the treatment and/or prevention of immune response or immune-mediated responses and diseases, such as the prevention or treatment of rejection following transplantation of synthetic or organic grafting materials, cells, organs or tissue to replace all or part of the function of tissues, such as heart, kidney, liver, bone marrow, skin, cornea, vessels, lung, pancreas, intestine, limb, muscle, nerve tissue, duodenum, small-bowel, pancreatic-islet-cell, including xeno-transplants, etc.; to treat or prevent graft-versus-host disease, autoimmune diseases, such as rheumatoid arthritis, systemic lupus erythematosus, thyroiditis, Hashimoto's thyroiditis, multiple sclerosis, myasthenia gravis, type I diabetes uveitis, juvenile-onset or recent-onset diabetes mellitus, uveitis, Graves disease, psoriasis, atopic dermatitis, Crohn's disease, ulcerative colitis, vasculitis, auto-antibody mediated diseases, aplastic anemia, Evan's syndrome, autoimmune hemolytic anemia, and the like; and further to treat infectious diseases causing aberrant immune response and/or activation, such as traumatic or pathogen induced immune disregulation, including for example, that which are caused by hepatitis B and C infections, HIV, staphylococcus aureus infection, viral encephalitis, sepsis, parasitic diseases wherein damage is induced by an inflammatory response (e.g., leprosy); and to prevent or treat circulatory diseases, such as arteriosclerosis, atherosclerosis, vasculitis, polyarteritis nodosa and myocarditis. In addition, the present invention may be used to prevent/suppress an immune response associated with a gene therapy treatment, such as the introduction of foreign genes into autologous cells and expression of the encoded product. Thus in one embodiment, the invention relates to a method of treating an immune response disease or disorder or an immune-mediated response or disorder in a subject in need of treatment comprising administering to said subject a therapeutically effective amount of a compound of the invention.

In one aspect, the invention provides the use of compounds of the invention in the treatment of a variety of neurodegenerative diseases, a non-exhaustive list of which is: I. Disorders characterized by progressive dementia in the absence of other prominent neurologic signs, such as Alzheimer's disease; Senile dementia of the Alzheimer type; and Pick's disease (lobar atrophy); II. Syndromes combining progressive dementia with other prominent neurologic abnormalities such as A) syndromes appearing mainly in adults (e.g., Huntington's disease, Multiple system atrophy combining dementia with ataxia and/or manifestations of Parkinson's disease, Progressive supranuclear palsy (Steel-Richardson-Olszewski), diffuse Lewy body disease, and corticodentatonigral degeneration); and B) syndromes appearing mainly in children or young adults (e.g., Hallervorden-Spatz disease and progressive familial myoclonic epilepsy); III. Syndromes of gradually developing abnormalities of posture and movement such as paralysis agitans (Parkinson's disease), striatonigral degeneration, progressive supranuclear palsy, torsion dystonia (torsion spasm; dystonia musculorum deformans), spasmodic torticollis and other dyskinesis, familial tremor, and Gilles de la Tourette syndrome; IV. Syndromes of progressive ataxia such as cerebellar degenerations (e.g., cerebellar cortical degeneration and olivopontocerebellar atrophy (OPCA)); and spinocerebellar degeneration (Friedreich's atazia and related disorders); V. Syndrome of central autonomic nervous system failure (Shy-Drager syndrome); VI. Syndromes of muscular weakness and wasting without sensory changes (motoneuron disease such as amyotrophic lateral sclerosis, spinal muscular atrophy (e.g., infantile spinal muscular atrophy (Werdnig-Hoffman), juvenile spinal muscular atrophy (Wohlfart-Kugelberg-Welander) and other forms of familial spinal muscular atrophy), primary lateral sclerosis, and hereditary spastic paraplegia; VII. Syndromes combining muscular weakness and wasting with sensory changes (progressive neural muscular atrophy; chronic familial polyneuropathies) such as peroneal muscular atrophy (Charcot-Marie-Tooth), hypertrophic interstitial polyneuropathy (Dejerine-Sottas), and miscellaneous forms of chronic progressive neuropathy; VIII Syndromes of progressive visual loss such as pigmentary degeneration of the retina (retinitis pigmentosa), and hereditary optic atrophy (Leber's disease). Furthermore, compounds of the invention can be implicated in chromatin remodeling.

The invention encompasses pharmaceutical compositions comprising pharmaceutically acceptable salts of the compounds of the invention as described above. The invention also encompasses pharmaceutical compositions comprising hydrates of the compounds of the invention. The term "hydrate" includes but is not limited to hemihydrate, monohydrate, dihydrate, trihydrate and the like. The invention further encompasses pharmaceutical compositions comprising any solid or liquid physical form of the compound of the invention. For example, the compounds can be in a crystalline form, in amorphous form, and have any particle size. The particles may be micronized, or may be agglomerated, particulate granules, powders, oils, oily suspensions or any other form of solid or liquid physical form.

The compounds of the invention, and derivatives, fragments, analogs, homologs, pharmaceutically acceptable salts or hydrate thereof can be incorporated into pharmaceutical compositions suitable for administration, together with a pharmaceutically acceptable carrier or excipient. Such compositions typically comprise a therapeutically effective amount of any of the compounds above, and a pharmaceutically acceptable carrier. Preferably, the effective amount when treating cancer is an amount effective to selectively induce terminal differentiation of suitable neoplastic cells and less than an amount which causes toxicity in a patient.

It will be appreciated that compounds of the invention can be used in combination with an immunotherapeutic agent. One form of immunotherapy is the generation of an active systemic tumor-specific immune response of host origin by administering a vaccine composition at a site distant from the tumor. Various types of vaccines have been proposed, including isolated tumor-antigen vaccines and anti-idiotype vaccines. Another approach is to use tumor cells from the subject to be treated, or a derivative of such cells (reviewed by Schirrmacher et al. (1995) J. Cancer Res. Clin. Oncol. 121:487). In U.S. Pat. No. 5,484,596, Hanna Jr. et al. claim a method for treating a resectable carcinoma to prevent recurrence or metastases, comprising surgically removing the tumor, dispersing the cells with collagenase, irradiating the cells, and vaccinating the patient with at least three consecutive doses of about $10^7$ cells.

It will be appreciated that the compounds of the invention may advantageously be used in conjunction with one or more other therapeutic agents. Examples of suitable agents for adjunctive therapy include a $5HT_1$ agonist, such as a triptan (e.g. sumatriptan or naratriptan); an adenosine A1 agonist; an EP ligand; an NMDA modulator, such as a glycine antagonist; a sodium channel blocker (e.g. lamotrigine); a substance P antagonist (e.g. an $NK_1$ antagonist); a cannabinoid; acetaminophen or phenacetin; a 5-lipoxygenase inhibitor; a leukotriene receptor antagonist; a DMARD (e.g. methotrexate); gabapentin and related compounds; a tricyclic antidepressant (e.g. amitryptilline); a neurone stabilising antiepileptic drug; a mono-aminergic uptake inhibitor (e.g. venlafaxine); a matrix metalloproteinase inhibitor; a nitric oxide synthase (NOS) inhibitor, such as an iNOS or an nNOS inhibitor; an inhibitor of the release, or action, of tumour necrosis factor .alpha.; an antibody therapy, such as a monoclonal antibody therapy; an antiviral agent, such as a nucleoside inhibitor (e.g. lamivudine) or an immune system modulator (e.g. interferon); an opioid analgesic; a local anaesthetic; a stimulant, including caffeine; an $H_2$-antagonist (e.g. ranitidine); a proton pump inhibitor (e.g. omeprazole); an antacid (e.g. aluminum or magnesium hydroxide); an antiflatulent (e.g. simethicone); a decongestant (e.g. phenylephrine, phenylpropanolamine, pseudoephedrine, oxymetazoline, epinephrine, naphazoline, xylometazoline, propylhexedrine, or levo-desoxyephedrine); an antitussive (e.g. codeine, hydrocodone, carmiphen, carbetapentane, or dextramethorphan); a diuretic; or a sedating or non-sedating antihistamine.

Compounds of the invention may be administered by any suitable means, including, without limitation, parenteral, intravenous, intramuscular, subcutaneous, implantation, oral, sublingual, buccal, nasal, pulmonary, transdermal, topical, vaginal, rectal, and transmucosal administrations or the like. Topical administration can also involve the use of transdermal administration such as transdermal patches or iontophoresis devices. Pharmaceutical preparations include a solid, semi-solid or liquid preparation (tablet, pellet, troche, capsule, suppository, cream, ointment, aerosol, powder, liquid, emulsion, suspension, syrup, injection etc.) containing a compound of the invention as an active ingredient, which is suitable for selected mode of administration. In one embodiment, the pharmaceutical compositions are administered orally, and are thus formulated in a form suitable for oral administration, i.e., as a solid or a liquid preparation. Suitable solid oral formulations include tablets, capsules, pills, granules, pellets, sachets and effervescent, powders, and the like. Suitable liquid oral formulations include solutions, suspensions, dispersions, emulsions, oils and the like. In one embodiment of the present invention, the composition is formulated in a capsule. In accordance with this embodiment, the compositions of the present invention comprise in addition to the active compound and the inert carrier or diluent, a hard gelatin capsule.

Any inert excipient that is commonly used as a carrier or diluent may be used in the formulations of the present invention, such as for example, a gum, a starch, a sugar, a cellulosic material, an acrylate, or mixtures thereof. A preferred diluent is microcrystalline cellulose. The compositions may further comprise a disintegrating agent (e.g., croscarmellose sodium) and a lubricant (e.g., magnesium stearate), and in addition may comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Daily administration may be repeated continuously for a period of several days to several years. Oral treatment may continue for between one week and the life of the patient. Preferably the administration may take place for five consecutive days after which time the patient can be evaluated to determine if further administration is required. The administration can be continuous or intermittent, e.g., treatment for a number of consecutive days followed by a rest period. The compounds of the present invention may be administered intravenously on the first day of treatment, with oral administration on the second day and all consecutive days thereafter.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the compound administered to the patient is less than an amount that would cause toxicity in the patient. In certain embodiments, the amount of the compound that is administered to the patient is less than the amount that causes a concentration of the compound in the patient's plasma to equal or exceed the toxic level of the compound. Preferably, the concentration of the compound in the patient's plasma is maintained at about 10 nM. In one embodiment, the concentration of the compound in the patient's plasma is maintained at about 25 nM. In one embodiment, the concentration of the compound in the patient's plasma is maintained at about 50 nM. In one embodiment, the concentration of the compound in the patient's plasma is maintained at about 100 nM. In one embodiment, the concentration of the compound in the patient's plasma is maintained at about 500 nM. In one embodiment, the concentration of the compound in the patient's plasma is maintained at about 1000 nM. In one embodiment, the concentration of the compound in the patient's plasma is maintained at about 2500 nM. In one embodiment, the concentration of the compound in the patient's plasma is maintained at about 5000 nM. The optimal amount of the compound that should be administered to the patient in the practice of the present invention will depend on the particular compound used and the type of cancer being treated.

DEFINITIONS

Listed below are definitions of various terms used to describe this invention. These definitions apply to the terms as they are used throughout this specification and claims, unless otherwise limited in specific instances, either individually or as part of a larger group.

An "aliphatic group" or "aliphatic" is non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. An aliphatic group, when used as a linker, preferably contains between about 1 and about 24 atoms, more preferably between about 4 to about 24 atoms, more preferably between about 4-12 atoms, more typically between about 4 and about 8 atoms. An aliphatic group, when used as a substituent, preferably contains between about 1 and about 24 atoms, more preferably between about 1 to about 10 atoms, more preferably between about 1-8 atoms, more typically between about 1 and about 6 atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups include alkyl, substituted alkyl, alkenyl, substituted alkenyl, alkynyl, substituted alkynyl groups described herein.

The term "substituted carbonyl" includes compounds and moieties which contain a carbon connected with a double bond to an oxygen atom, and tautomeric forms thereof. Examples of moieties that contain a substituted carbonyl include aldehydes, ketones, carboxylic acids, amides, esters, anhydrides, etc. The term "carbonyl moiety" refers to groups such as "alkylcarbonyl" groups wherein an alkyl group is covalently bound to a carbonyl group, "alkenylcarbonyl" groups wherein an alkenyl group is covalently bound to a carbonyl group, "alkynylcarbonyl" groups wherein an alkynyl group is covalently bound to a carbonyl group, "arylcarbonyl" groups wherein an aryl group is covalently attached to the carbonyl group. Furthermore, the term also refers to groups wherein one or more heteroatoms are covalently bonded to the carbonyl moiety. For example, the term includes moieties such as, for example, aminocarbonyl moieties, (wherein a nitrogen atom is bound to the carbon of the carbonyl group, e.g., an amide).

The term "acyl" refers to hydrogen, alkyl, partially saturated or fully saturated cycloalkyl, partially saturated or fully saturated heterocycle, aryl, and heteroaryl substituted carbonyl groups. For example, acyl includes groups such as ($C_1$-$C_6$)alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about eight carbon atoms. Examples of such radicals include methyl, ethyl, n-propyl, isopropyl, n-butyl, isobutyl, sec-butyl, tert-butyl, pentyl, iso-amyl, hexyl and the like.

The term "alkenyl" embraces linear or branched radicals having at least one carbon-carbon double bond of two to about twenty carbon atoms or, preferably, two to about twelve carbon atoms. More preferred alkenyl radicals are "lower alkenyl" radicals having two to about ten carbon atoms and more preferably about two to about eight carbon atoms. Examples of alkenyl radicals include ethenyl, allyl, propenyl, butenyl and 4-methylbutenyl. The terms "alkenyl", and "lower alkenyl", embrace radicals having "cis" and "trans" orientations, or alternatively, "E" and "Z" orientations.

The term "alkynyl" embraces linear or branched radicals having at least one carbon-carbon triple bond of two to about twenty carbon atoms or, preferably, two to about twelve carbon atoms. More preferred alkynyl radicals are "lower alkynyl" radicals having two to about ten carbon atoms and more preferably about two to about eight carbon atoms. Examples of alkynyl radicals include propargyl, 1-propynyl, 2-propynyl, 1-butyne, 2-butynyl and 1-pentynyl.

The term "cycloalkyl" embraces saturated carbocyclic radicals having three to about twelve carbon atoms. The term "cycloalkyl" embraces saturated carbocyclic radicals having three to about twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl.

The term "cycloalkenyl" embraces partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkoxy" embraces linear or branched oxy-containing radicals each having alkyl portions of one to about one to about twenty carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" embraces alkyl radicals having one or more alkoxy radicals attached to the alkyl radical, that is, to form monoalkoxyalkyl and dialkoxyalkyl radicals.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

The terms "heterocyclyl", "heterocycle" "heterocyclic" or "heterocyclo" embrace saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" embraces unsaturated heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" embraces heterocyclo-substituted alkyl radicals. More preferred heterocycloalkyl radicals are "lower heterocycloalkyl" radicals having one to six carbon atoms in the heterocycloalkyl radicals.

The term "alkylthio" embraces radicals containing a linear or branched alkyl radical, of one to about ten carbon atoms attached to a divalent sulfur atom. Preferred alkylthio radicals have alkyl radicals of one to about twenty carbon atoms or, preferably, one to about twelve carbon atoms. More preferred alkylthio radicals have alkyl radicals are "lower alkylthio" radicals having one to about ten carbon atoms. Most preferred are alkylthio radicals having lower alkyl radicals of one to about eight carbon atoms. Examples of such lower alkylthio radicals are methylthio, ethylthio, propylthio, butylthio and hexylthio.

The terms "aralkyl" or "arylalkyl" embrace aryl-substituted alkyl radicals such as benzyl, diphenylmethyl, triphenylmethyl, phenylethyl, and diphenylethyl.

The term "aryloxy" embraces aryl radicals attached through an oxygen atom to other radicals.

The terms "aralkoxy" or "arylalkoxy" embrace aralkyl radicals attached through an oxygen atom to other radicals.

The term "aminoalkyl" embraces alkyl radicals substituted with amino radicals. Preferred aminoalkyl radicals have alkyl radicals having about one to about twenty carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, oxo, thioxy, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

As used herein, the term "aberrant proliferation" refers to abnormal cell growth.

The phrase "adjunctive therapy" encompasses treatment of a subject with agents that reduce or avoid side effects associated with the combination therapy of the present invention, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The term "angiogenesis," as used herein, refers to the formation of blood vessels. Specifically, angiogenesis is a multi-step process in which endothelial cells focally degrade and invade through their own basement membrane, migrate through interstitial stroma toward an angiogenic stimulus, proliferate proximal to the migrating tip, organize into blood vessels, and reattach to newly synthesized basement membrane (see Folkman et al., Adv. Cancer Res., Vol. 43, pp. 175-203 (1985)). Anti-angiogenic agents interfere with this process. Examples of agents that interfere with several of these steps include thrombospondin-1, angiostatin, endostatin, interferon alpha and compounds such as matrix metalloproteinase (MMP) inhibitors that block the actions of enzymes that clear and create paths for newly forming blood vessels to follow; compounds, such as .alpha.v.beta.3 inhibitors, that interfere with molecules that blood vessel cells use to bridge between a parent blood vessel and a tumor; agents, such as specific COX-2 inhibitors, that prevent the growth of cells that form new blood vessels; and protein-based compounds that simultaneously interfere with several of these targets.

The term "apoptosis" as used herein refers to programmed cell death as signaled by the nuclei in normally functioning human and animal cells when age or state of cell health and condition dictates. An "apoptosis inducing agent" triggers the process of programmed cell death.

The term "cancer" as used herein denotes a class of diseases or disorders characterized by uncontrolled division of cells and the ability of these cells to invade other tissues, either by direct growth into adjacent tissue through invasion or by implantation into distant sites by metastasis.

The term "compound" is defined herein to include pharmaceutically acceptable salts, solvates, hydrates, polymorphs, enantiomers, diastereoisomers, racemates and the like of the compounds having a formula as set forth herein.

The term "devices" refers to any appliance, usually mechanical or electrical, designed to perform a particular function.

As used herein, the term "dysplasia" refers to abnormal cell growth.

The term "hyperplasia," as used herein, refers to excessive cell division or growth.

The phrase an "immunotherapeutic agent" refers to agents used to transfer the immunity of an immune donor, e.g., another person or an animal, to a host by inoculation. The term embraces the use of serum or gamma globulin containing performed antibodies produced by another individual or an animal; nonspecific systemic stimulation; adjuvants; active specific immunotherapy; and adoptive immunotherapy. Adoptive immunotherapy refers to the treatment of a disease by therapy or agents that include host inoculation of sensitized lymphocytes, transfer factor, immune RNA, or antibodies in serum or gamma globulin.

The term "inhibition," in the context of neoplasia, tumor growth or tumor cell growth, may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention or chemoprevention.

The term "metastasis," as used herein, refers to the migration of cancer cells from the original tumor site through the blood and lymph vessels to produce cancers in other tissues. Metastasis also is the term used for a secondary cancer growing at a distant site.

The term "neoplasm," as used herein, refers to an abnormal mass of tissue that results from excessive cell division. Neoplasms may be benign (not cancerous), or malignant (cancerous) and may also be called a tumor. The term "neoplasia" is the pathological process that results in tumor formation.

As used herein, the term "pre-cancerous" refers to a condition that is not malignant, but is likely to become malignant if left untreated.

The term "proliferation" refers to cells undergoing mitosis.

The phrase "HSP90 related disease or disorder" refers to a disease or disorder characterized by inappropriate HSP90 activity or over-activity of the HSP90. Inappropriate activity refers to either; (i) HSP90 expression in cells which normally do not express HSP90; (ii) increased HSP90 expression leading to unwanted cell proliferation, differentiation and/or growth; or, (iii) decreased HSP90 expression leading to unwanted reductions in cell proliferation, differentiation and/or growth. Over-activity of HSP90 refers to either amplification of the gene encoding a particular HSP90 or production of a level of HSP90 activity which can correlate with a cell proliferation, differentiation and/or growth disorder (that is, as the level of the HSP90 increases, the severity of one or more of the symptoms of the cellular disorder increases).

The phrase a "radio therapeutic agent" refers to the use of electromagnetic or particulate radiation in the treatment of neoplasia.

The term "recurrence" as used herein refers to the return of cancer after a period of remission. This may be due to incomplete removal of cells from the initial cancer and may occur locally (the same site of initial cancer), regionally (in vicinity of initial cancer, possibly in the lymph nodes or tissue), and/or distally as a result of metastasis.

The term "treatment" refers to any process, action, application, therapy, or the like, wherein a mammal, including a human being, is subject to medical aid with the object of improving the mammal's condition, directly or indirectly.

The term "vaccine" includes agents that induce the patient's immune system to mount an immune response against the tumor by attacking cells that express tumor associated antigens (Teas).

As used herein, the term "effective amount of the subject compounds," with respect to the subject method of treatment, refers to an amount of the subject compound which, when delivered as part of desired dose regimen, brings about, e.g. a change in the rate of cell proliferation and/or state of differentiation and/or rate of survival of a cell to clinically acceptable standards. This amount may further relieve to some extent one or more of the symptoms of a neoplasia disorder, including, but is not limited to: 1) reduction in the number of cancer cells; 2) reduction in tumor size; 3) inhibition (i.e., slowing to some extent, preferably stopping) of cancer cell infiltration into peripheral organs; 4) inhibition (i.e., slowing to some extent, preferably stopping) of tumor metastasis; 5) inhibition, to some extent, of tumor growth; 6) relieving or reducing to some extent one or more of the symptoms associated with the disorder; and/or 7) relieving or reducing the side effects associated with the administration of anticancer agents.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical *Sciences,* 66: 1-19 (1977). The salts can be prepared in situ during the final isolation and purification of the compounds of the invention, or separately by reacting the free base function with a suitable organic acid or inorganic acid. Examples of pharmaceutically acceptable nontoxic acid addition salts include, but are not limited to, salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid lactobionic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As used herein, the term "pre-cancerous" refers to a condition that is not malignant, but is likely to become malignant if left untreated.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers and/or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; cyclodextrins such as alpha-($\alpha$), beta-(B) and gamma-($\gamma$) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al, and WO 98/43,650 by Montgomery, all of which are incorporated herein by reference). A discussion of pulmonary delivery of antibiotics is also found in U.S. Pat. No. 6,014,969, incorporated herein by reference.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Synthetic Methods

The compounds of the invention, or a pharmaceutically-acceptable salt thereof, may be prepared by any process known to be applicable to the preparation of chemically-related compounds. Suitable processes for making certain intermediates include, for example, those illustrated in PCT publication numbers WO02/36075, WO03/037860 and WO2006084030. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of a chemist.

The compounds and processes of the present invention will be better understood in connection with the following representative synthetic schemes that illustrate the methods by which the compounds of the invention may be prepared, which are intended as an illustration only and not limiting of the scope of the invention.

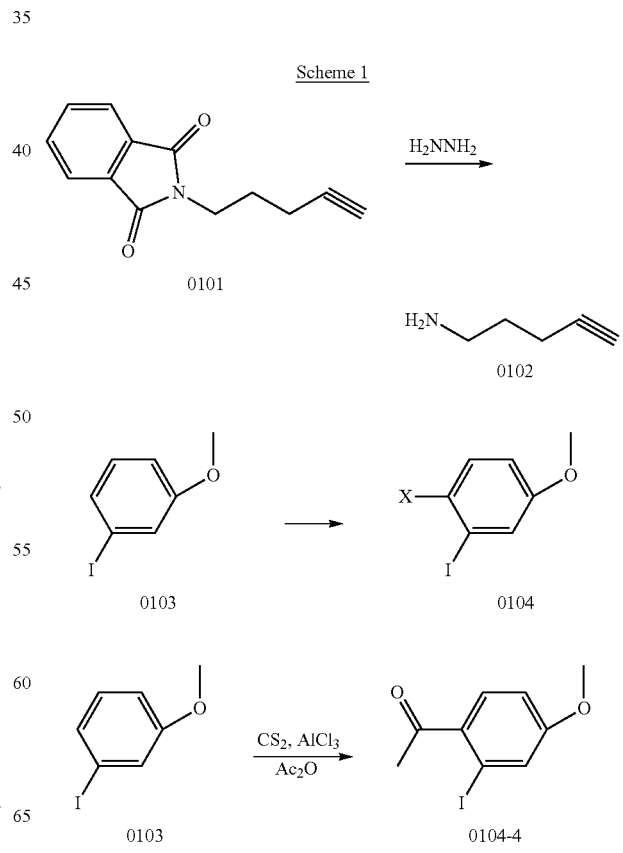

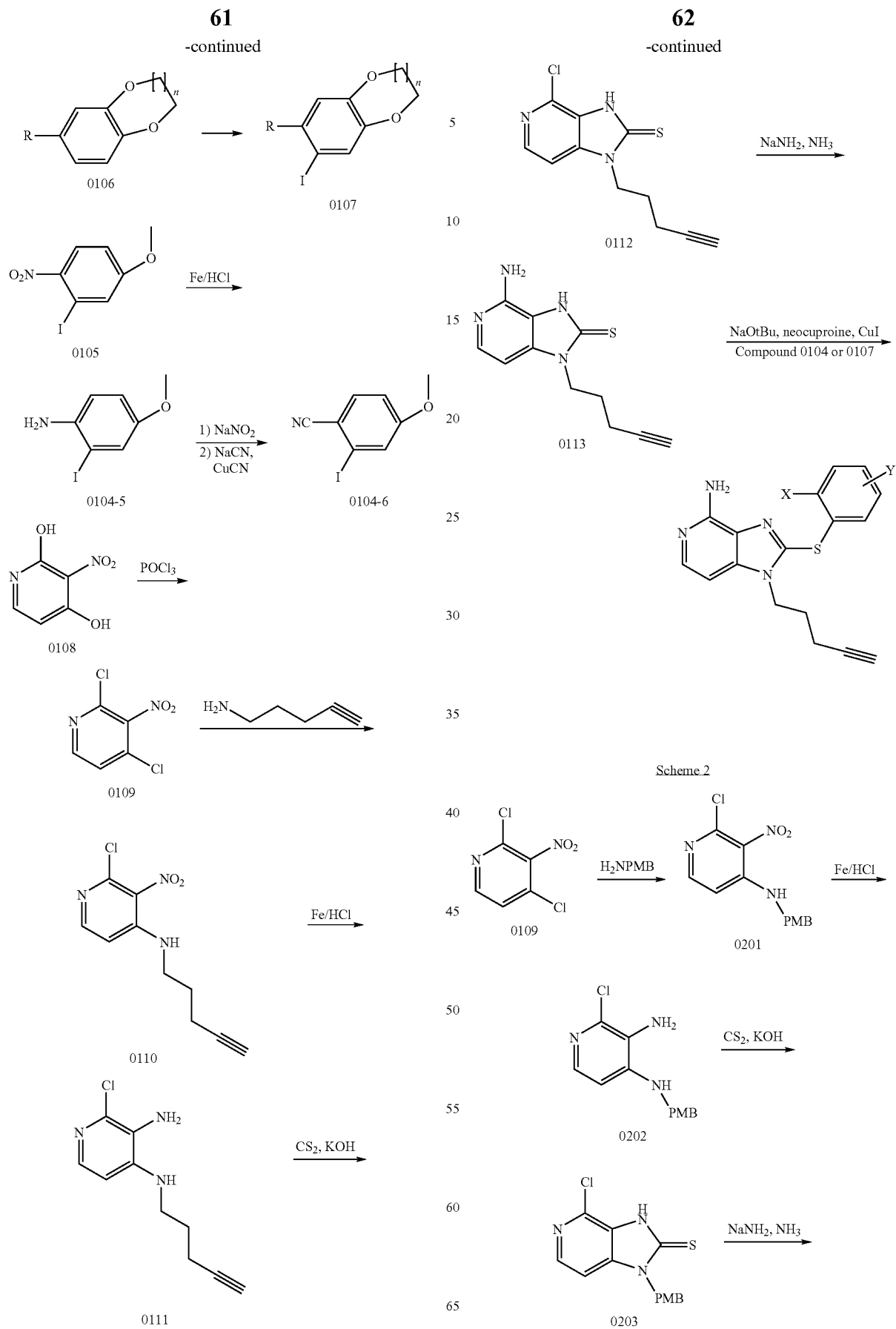

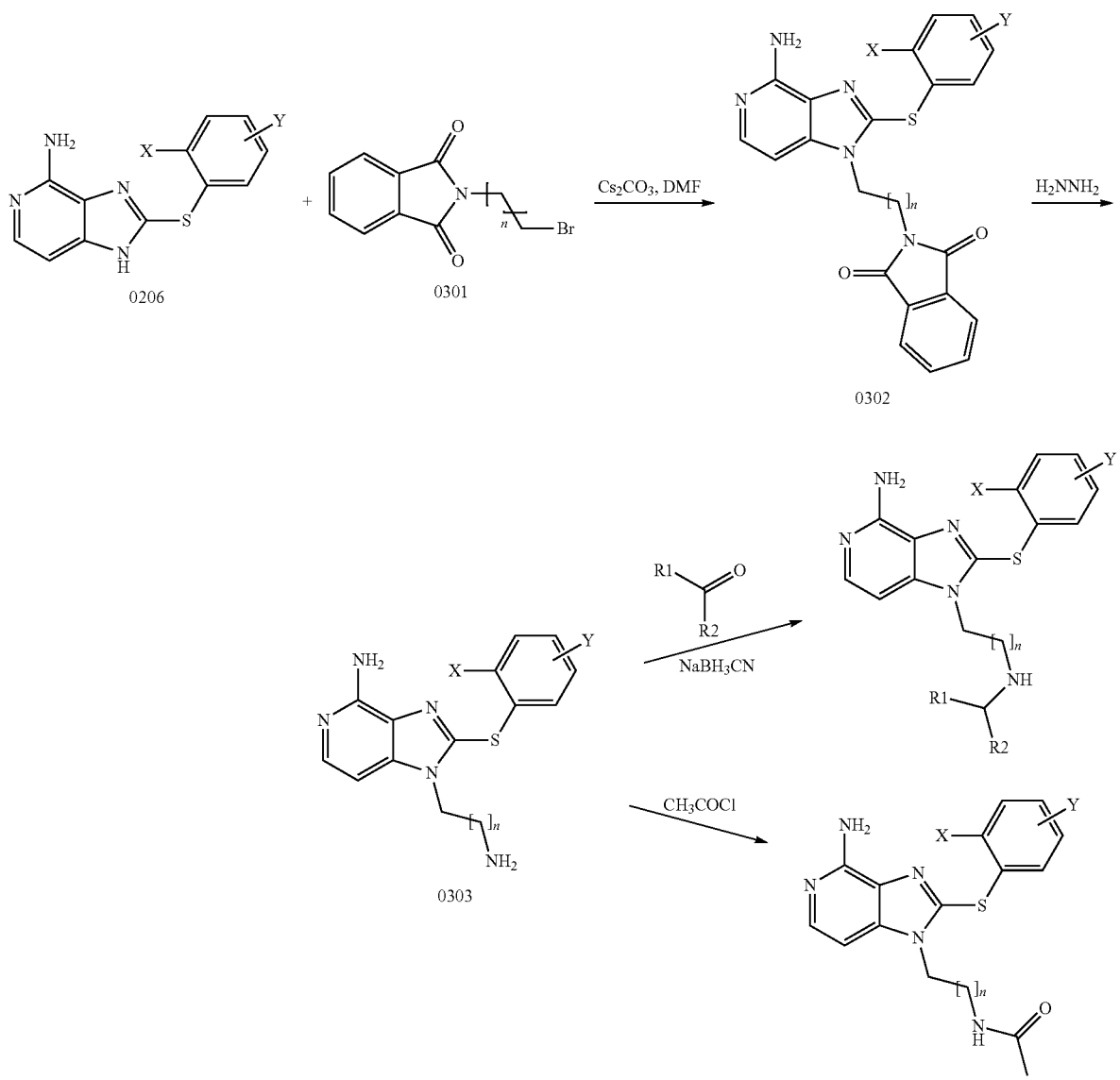
Scheme 3

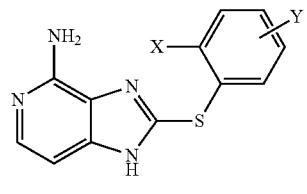 + 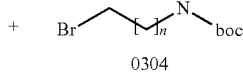 $\xrightarrow{Cs_2CO_3, DMF}$ 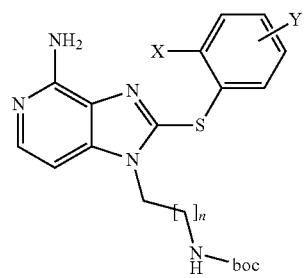 $\xrightarrow{TFA}$
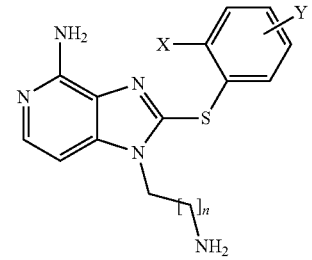
Scheme 4
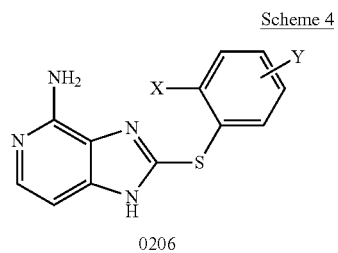 +
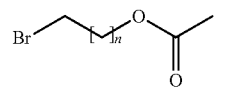 $\xrightarrow{Cs_2CO_3, DMF}$
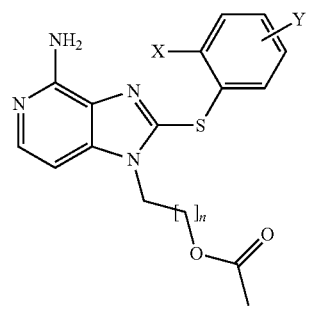 $\xrightarrow{KOH, MeOH}$
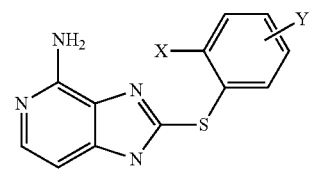 $\xrightarrow{MsCl, Et_3N}$
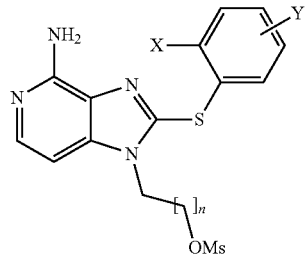 $\xrightarrow{R3\text{-}R4\text{-}NH_2}$
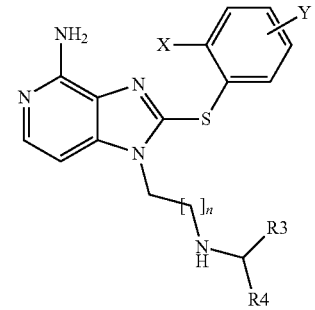
Scheme 5
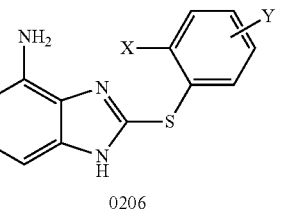 +
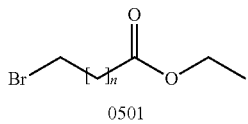 $\xrightarrow{Cs_2CO_3, DMF}$

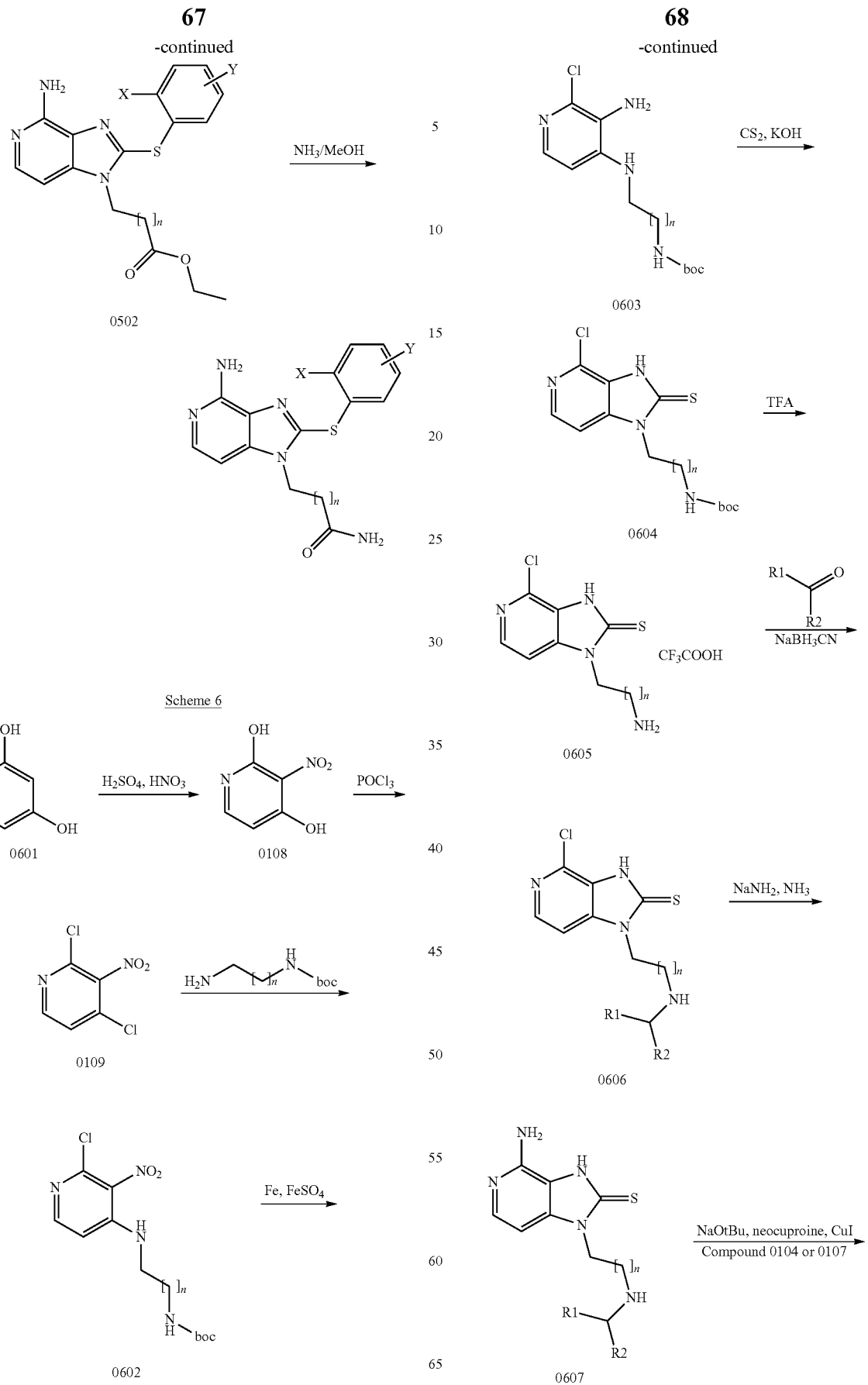

-continued

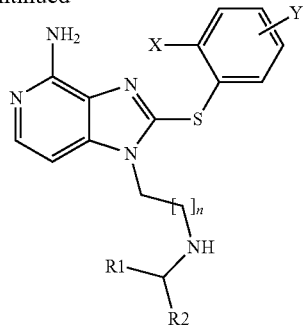

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Preparation of 2-(6-bromobenzo[d][1,3]dioxol-5-ylthio)-1-(pent-4-ynyl)-1H-imidazo[4,5-c]pyridin-4-amine (Compound 1)

Step 1a. Pent-4-yn-1-amine (Compound 0102)

To a solution of compound 0101 (6.0 g, 28.14 mmol) in a mixture solvents of methylene chloride and ethanol (10:1, 220 mL) was added hydrazine monohydrate (14.1 g, 281.4 mmol). The reaction mixture was refluxed for 5 hours and was then cooled and filtered. Water (200 mL) was added and the pH was adjusted to 2 with 6N HCl. The mixture was stirred adequately and methylene chloride layer was separated. The aqueous layer was adjusted to pH13 and was extracted with two portions of methylene chloride. The organic phase was collected and evaporated under atmosphere pressure to give the title product 0102 as a brown oil (4.4 g) which was used directly to the next step without further purification. LCMS: 84 [M+1]$^+$.

Step 1b. 2,4-Dichloro-3-nitropyridine (Compound 0109)

Compound 0108 (10.0 g, 64.0 mmol) was dissolved in POCl$_3$ (70 mL) and heated overnight at 85° C. The excess POCl$_3$ was evaporated at atmosphere pressure. The residuum was neutralized (pH7) with saturated NaHCO$_3$. The precipitate was filtered and dried to give the title compound 0109 as a yellow solid (9.95 g, 80.5%): $^1$H NMR (CDCl$_3$) δ 7.47 (d, J=5.7 Hz, 1H), 8.44 (d, J=5.1 Hz, 1H).

Step 1c. 2-Chloro-3-nitro-N-(pent-4-ynyl)pyridin-4-amine (Compound 0110)

To a solution of compound 0109 (8.9 g, 46.12 mmol) in DMF (177 mL) was added compound 0102 (5.8 g) and triethylamine (5.6 g, 55.34 mmol). The reaction mixture was stirred at room temperature for 4 hours. The mixture was evaporated to remove DMF and purified by column chromatography on silica gel (EtOAc/petroleum=10:1) to obtain the title compound 0110 as a yellow solid (8.6 g, 77.8%): LCMS: 240 [M+1]$^+$; $^1$H NMR (CDCl$_3$) δ 1.89 (m, 2H), 2.06 (t, J=2.7 Hz, 1H), 2.35 (m, 2H), 3.45 (m, 2H), 6.63 (s, 1H), 6.69 (d, J=6.3 Hz, 1H), 8.04 (d, J=6.3 Hz, 1H).

Step 1d. 2-Chloro-N$^4$-(pent-4-ynyl)pyridine-3,4-diamine (Compound 0111)

To a solution of compound 0110 (8.6 g, 35.88 mmol) in methanol (430 mL) was added water (43 mL), iron powder (20.04 g) and concentrated HCl solution (3 mL) The reaction mixture was stirred at room temperature for 30 minutes and then heated to refluxed overnight. The mixture was adjusted to pH11 with 6N NaOH and filtered and washed with methanol (50 mL). The filtrate was concentrated and purified by column chromatography on silica gel (EtOAc/petroleum=2:1) to obtain the title compound 0111 as a light yellow solid (5.5 g, 73.1%). LCMS: 210 [M+1]$^+$; $^1$H NMR (DMSO-d$_6$) δ 1.75 (m, 2H), 2.29 (m, 2H), 2.83 (t, J=2.7 Hz, 1H), 3.19 (m, 2H), 4.78 (s, 2H) 5.73 (t, J=5.1 Hz, 1H) 6.41 (d, J=5.4 Hz, 1H), 7.41 (d, J=5.1 Hz, 1H).

Step 1e. 4-Chloro-1-(pent-4-ynyl)-1H-imidazo[4,5-c]pyridine-2(3H)-thione (Compound 0112)

A mixture of compound 0111 (3.64 g, 17.36 mmol), carbon disulfide (6.6 g, 86.8 mmol), potassium hydroxide (4.87 g 86.8 mmol) in ethanol (22 mL) and water (3.3 mL) was heated to refluxed overnight. The mixture was cooled to room temperature and water (60 mL) was added. The mixture was adjusted to pH7 with acetic acid and then extracted with methylene chloride (100 mL×2). The organic phase was concentrated at reduced pressure and purified by column chromatography on silica gel (EtOAc/petroleum at 5:1) to obtain the title compound 0112 as a light yellow solid (3.9 g, 89%): LCMS: 252 [M+1]$^+$; $^1$H NMR (DMSO-d$_6$) δ 1.91 (m, 2H), 2.26 (m, 1H), 2.83 (t, J=2.7 Hz, 2H), 4.28 (t, J=7.5 Hz, 2H), 7.53 (d, J=5.1 Hz, 1H), 8.15 (d, J=5.4 Hz, 1H), 13.64 (s, 1H).

Step 1f. 4-Amino-1-(pent-4-ynyl)-1H-imidazo[4,5-c]pyridine-2(3H)-thione (Compound 0113)

A mixture of compound 0112 (1.0 g, 4.0 mmol) and sodium amide (3.0 g, 77.0 mmol) in 25 mL liquid ammonia was charged in an air free sealed tube and stirred at 0° C. for 30 hours. The tube was opened after cooled to −40° C. and ethanol was added carefully to terminate the reaction until no gas generated. 200 mL of water was added and adjusted the mixture to pH 7 with acetic acid and then extracted with two portions of methylene chloride. The combined organic phase was concentrated at reduced pressure and purified by column chromatography on silica gel (methylene chloride/methanol=50:1) to obtain the title compound 0113 as a grey solid (497 mg, 54%). LCMS: 233 [M+1]$^+$; $^1$H NMR (DMSO-d$_6$) δ 1.89 (m, 2H), 2.23 (m, 2H), 2.86 (s, 1H), 4.19 (t, J=7.5 Hz, 2H), 6.12 (s, 2H), 6.75 (d, J=5.4 Hz, 1H), 7.74 (d, J=5.4 Hz, 1H), 12.50 (s, 1H).

Step 1g. 5-Bromo-6-iodobenzo[d][1,3]dioxole (Compound 0107-1)

A solution of compound 0106 (10.0 g, 50.0 mmol), anhydrous acetonitrile (150 mL), TFA (11.4 g, 100.0 mmol) and NIS (33.7 g, 150.0 mmol) was stirred at room temperature for 24 h. The solvent was removed under reduce pressure and the crude purified by column chromatography on silica gel (petroleum) to yield the title compound 0107-1 as a white solid (18.5 g, 91%): $^1$H NMR (DMSO-d$_6$) δ 5.99 (s, 2H), 7.10 (s, 1H), 7.26 (s, 1H).

Step 1h. 2-(6-Bromobenzo[d][1,3]dioxol-5-ylthio)-1-(pent-4-ynyl)-1H-imidazo[4,5-c]pyridin-4-amine (Compound 1)

A mixture of compound 0113 (150.0 mg, 0.65 mmol), 5-Bromo-6-iodobenzo[d][1,3]dioxole (Compound 0107) (633.0 mg, 1.94 mmol), neocuproine hydrate (13.0 mg, 0.065 mmol), CuI (12.0 mg, 0.065 mmol) and NaOt-Bu (124.0 mg, 1.29 mmol) in anhydrous DMF (6 mL) was stirred for 24 h at 110° C. (oil bath) under nitrogen atmosphere. The solvent was removed under high vacuum and the crude purified by column chromatography on silica gel (CH$_2$Cl$_2$/MeOH=100/1) to obtain the title compound 1 as an orange solid (117 mg, 42%): m.p. 52.9~60.5° C., LCMS: 432 [M+1]$^+$; $^1$H NMR (DMSO-d$_6$) δ 1.81 (m, 2H), 2.19 (m, 2H), 2.83 (t, J=2.4 Hz, 1H), 4.25 (t, J=7.2 Hz, 2H), 6.07 (s, 2H), 6.38 (s, 2H), 6.71 (s 1H), 6.83 (d, J=6.0 Hz, 1H,), 7.35 (s, 1H), 7.72 (d, J=5.4 Hz, 1H).

Example 2

Preparation of 2-(6-chlorobenzo[d][1,3]dioxol-5-ylthio)-1-(pent-4-ynyl)-1H-imidazo[4,5-c]pyridin-4-amine (Compound 2)

Step 2a. 5-Chloro-6-iodobenzo[d][1,3]dioxole (Compound 0107)

A solution of compound 0106 (2.0 g, 12.77 mmol), acetonitrile (80 mL), TFA (2.9 g) and NIS (8.6 g, 38.3 mmol) was stirred at room temperature for 24 h. The solvent was removed under high vacuum and the crude product was purified by column chromatography on silica gel (petroleum) to yield the title compound 0107 as a white solid (3.27 g, 90.6%): $^1$H NMR (DMSO-d$_6$) δ 6.10 (s, 2H), 7.25 (s, 1H), 7.45 (s, 1H).

Step 2b. 2-(6-Chlorobenzo[d][1,3]dioxol-5-ylthio)-1-(pent-4-ynyl)-1H-imidazo[4,5-c]pyridin-4-amine (Compound 2)

A mixture of compound 0113 (100 mg, 0.43 mmol), 5-Chloro-6-iodobenzo[d][1,3]dioxole (Compound 0107) (364 mg, 1.29 mmol), neocuproine hydrate (9 mg, 0.043 mmol), CuI (8 mg, 0.043 mmol) and NaO-t-Bu (83 mg, 0.86 mmol) in anhydrous DMF (4.6 mL) was stirred for 24 h at 110° C. (oil bath) under nitrogen atmosphere. The solvent was removed under high vacuum and the crude purified by column chromatography on silica gel (CH$_2$Cl$_2$/MeOH at 100/1) to obtain the title compound 1 as a light yellow solid (52 mg, 31%): LCMS: 387 [M+1]$^+$; $^1$H NMR (DMSO-d$_6$) δ 1.81 (m, 2H), 2.19 (m, 2H), 2.85 (t, 1H, J=2.4 Hz), 4.25 (t, 2H, J=7.2 Hz), 6.09 (s, 2H), 6.37 (s, 2H), 6.76 (s 1H), 6.82 (d, 1H, J=5.7 Hz), 7.25 (s, 1H), 7.71 (d, 1H, J=5.7 Hz).

Example 3

Preparation of 2-(6-iodobenzo[d][1,3]dioxol-5-ylthio)-1-(pent-4-ynyl)-1H-imidazo[4,5-c]pyridin-4-amine (Compound 3)

Step 3a. 5,6-Diiodobenzo[d][1,3]dioxole (Compound 0107)

A solution of compound 0106 (1.0 g, 8.19 mmol), acetonitrile (51 mL), TFA (1.867 g) and NIS (4.05 g, 18.02 mmol) was stirred at room temperature for 24 h. The solvent was removed under high vacuum and the crude product purified by column chromatography on silica gel (petroleum) to yield the title compound 0107 as a white solid (1.48 g, 48%): $^1$H NMR (DMSO-d$_6$) δ 6.05 (s, 2H), 7.46 (s, 2H).

Step 3b. 2-(6-Iodobenzo[d][1,3]dioxol-5-ylthio)-1-(pent-4-ynyl)-1H-imidazo[4,5-c]pyridin-4-amine (Compound 3)

A mixture of compound 0113 (200 mg, 0.86 mmol), 5,6-Diiodobenzo[d][1,3]dioxole (Compound 0107) (483 mg, 1.29 mmol), neocuproine hydrate (18 mg, 0.086 mmol), CuI (16 mg, 0.086 mmol) and NaO-t-Bu (83 mg, 0.86 mmol) in anhydrous DMF (8 mL) was stirred for 24 h at 110° C. (oil bath) under nitrogen atmosphere. The solvent was removed under high vacuum and the crude purified by column chromatography on silica gel (CH$_2$Cl$_2$/MeOH at 100/1) to obtain the title compound 3 as a white solid (82 mg, 20%): LCMS: 479 [M+1]$^+$; $^1$H NMR (DMSO-d$_6$) δ 1.81 (m, 2H), 2.20 (m, 2H), 2.84 (t, 1H, J=2.4 Hz), 4.23 (t, 2H, J=7.2 Hz), 6.05 (s, 2H), 6.37 (s, 2H), 6.69 (s 1H), 6.82 (d, 1H, J=6.0 Hz), 7.48 (s, 1H), 7.72 (d, 1H, J=5.7 Hz).

Example 3

(Method 2): Preparation of 2-(6-iodobenzo[d][1,3]dioxol-5-ylthio)-1-(pent-4-ynyl)-1H-imidazo[4,5-c]pyridin-4-amine (Compound 3)

Step 3a'. 2-Chloro-N-(4-methoxybenzyl)-3-nitropyridin-4-amine (Compound 0201)

To a solution of compound 0109 (1 g, 5.18 mmol) in was in DMF (8.6 mL) was added (4-methoxyphenyl)methanamine (0.71 g, 5.18 mmol) and triethylamine (0.644 mL). The solution was stirred at room temperature for 2 h. The mixture was evaporated to remove DMF. The resulting mixture was purified by column chromatography on silica gel (EtOAc/petroleum at 10:1) to obtain the title compound 0201 as a yellow solid (1.32 g, 87%): LCMS: 294 [M+1]$^+$; $^1$H NMR (DMSO-d$_6$) δ 3.72 (s, 3H), 4.40 (d, 2H, J=6.3 Hz), 6.81 (d, 1H, J=5.7 Hz), 6.91 (d, 2H, J=9.0 Hz), 7.25 (d, 2H, J=8.4 Hz), 7.95 (d, 1H, J=5.4 Hz), 8.02 (t, 1H, J=5.7 Hz).

Step 3b'. 2-Chloro-N$^4$-(4-methoxybenzyl)pyridine-3,4-diamine (Compound 0202)

To a mixture of compound 0201 (1.32 g, 4.49 mmol) in methanol (66 mL) and water (6.6 mL) was added iron powder (2.51 g, 44.9 mmol) and concentrated HCl solution (1 mL). The mixture was stirred at room temperature for 30 min, and then at reflux overnight. The mixture was adjusted to pH 11 with 6N NaOH and filtered. The precipitate was washed with methanol (10 mL). The combined filtrate and wash solution was concentrated and purified by column chromatography on silica gel (EtOAc/petroleum at 2:1) to obtain the title compound 0202 as a light green solid (712 mg, 60%): LCMS: 264 [M+1]$^+$; $^1$H NMR (DMSO-d$_6$) δ 3.73 (s, 3H), 4.31 (d, 2H, J=5.7 Hz), 4.81 (s, 2H), 6.33 (m, 2H), 6.90 (d, 2H, J=8.7 Hz), 7.26 (d, 2H, J=9.90 Hz), 7.34 (d, 1H, J=5.1 Hz).

Step 3c'. 4-Chloro-1-(4-methoxybenzyl)-1H-imidazo[4,5-c]pyridine-2(3H)-thione (Compound 0203)

A mixture of 0202 (2 g, 7.6 mmol), carbon disulfide (2.88 g, 37.9 mmol), potassium hydroxide (2.12 g, 37.9 mmol) in ethanol (11.5 mL) and water (1.5 mL) was heated at reflux overnight. Water (100 mL) was added after the mixture was allowed to cool down to room temperature. The mixture was adjusted to pH 7 with acetic acid and then extracted with two portions of methylene chloride. The organic layer was collected and concentrated at reduced pressure to leave an residue which was purified by column chromatography on silica gel (EtOAc/petroleum at 5:1) to obtain the title compound 0203 as a white solid (2 g, 86%): LCMS: 306 [M]$^+$; $^1$H NMR (DMSO-d$_6$) δ 3.68 (s, 3H), 6.41 (s, 2H), 6.86 (d, 2H, J=8.7 Hz), 7.36 (m, 3H), 8.07 (d, 1H, J=5.4 Hz), 13.74 (s, 1H).

Step 3d'. 4-Amino-1-(4-methoxybenzyl)-1H-imidazo[4,5-c]pyridine-2(3H)-thione (Compound 0204)

A mixture of 0203 (1 g, 3.25 mmol) and sodium amide (3 g, 77 mmol) in 25 mL liquid ammonia was charged in an air free sealed tube. The mixture was then stirred at room temperature for 30 h. The mixture was cooled to −40° C. and then tube was opened. Ethanol was added carefully to terminate the reaction until no gas generated. Water (200 mL) was added and the mixture was adjusted to pH 7 with acetic acid. The resulting solid was filtered to obtain crude product which was purified by column chromatography on silica gel (methylene chloride/methanol at 50:1) to obtain the title compound 0204 as a white solid (718 mg, 77%): LCMS: 287 [M]$^+$; $^1$H NMR (DMSO-d$_6$) δ 3.68 (s, 3H), 5.31 (s, 2H), 6.06 (s, 2H), 6.59 (d, 1H, J=6.3 Hz), 6.85 (d, 2H, J=9.0 Hz), 7.33 (d, 2H, J=8.4 Hz), 7.64 (d, 1H, J=5.7 Hz), 12.53 (s, 1H).

Step 3e' 2-(6-iodobenzo[d][1,3]dioxol-5-ylthio)-1-(4-methoxybenzyl)-1H-imidazo[4,5-c]pyridin-4-amine (Compound 0205-3)

A mixture of 0204 (725 mg, 2.53 mmol), 5,6-Diiodobenzo[d][1,3]dioxole (0107) (1.89 g, 5.06 mmol), neocuproine hydrate (53 mg, 0.253 mmol), CuI (48 mg, 0.253 mmol) and NaOt-Bu (365 mg, 3.80 mmol) in anhydrous DMF (32 mL) was stirred for 24 h at 110° C. (oil bath) under nitrogen atmosphere. The solvent was removed under high vacuum and the crude purified by column chromatography on silica gel (CH$_2$Cl$_2$/MeOH at 100/1) to obtain the title compound 0205-3 as a brown solid (734 mg, 55%): LCMS: 533 [M+1]$^+$; $^1$H NMR (DMSO-d$_6$) δ 3.69 (s, 3H), 5.35 (s, 2H), 6.01 (s, 2H), 6.47 (s, 1H), 6.80 (d, 2H, J=9.0 Hz), 7.06 (d, 2H, J=8.7 Hz), 7.41 (s, 1H).

Step 3f'. 2-(6-Iodobenzo[d][1,3]dioxol-5-ylthio)-1H-imidazo[4,5-c]pyridin-4-amine (Compound 0206-3)

A solution of 0205-3 (730 mg, 1.37 mmol) in TFA (4.8 mL) was stirred for 2 h at 80° C. The TFA was then evaporated and the resulting oil was adjusted to pH 7 with saturated NaHCO$_3$. The resulting precipitate was collected by filtration and further purified by column chromatography on silica gel (CH$_2$Cl$_2$/MeOH at 30/1) to give the title compound 0206-3 as a yellow solid (526 mg, 93%): LCMS: 413 [M+1]$^+$; $^1$H NMR (DMSO-d$_6$) δ 6.09 (s, 2H), 6.73 (m, 3H), 7.03 (s, 1H), 7.52 (m, 2H), 12.45 (s, 1H).

Step 3g'. 2-(6-Iodobenzo[d][1,3]dioxol-5-ylthio)-1-(pent-4-ynyl)-1H-imidazo[4,5-c]pyridin-4-amine (Compound 3)

A mixture of 0206-3 (1 g, 2.426 mmol), 5-chloropent-1-yne (373 mg, 3.639 mmol) and Cs$_2$CO$_3$ (1.34 g, 4.124 mmol) in DMF (35 mL) was stirred at 85° C. for 4 h. DMF was evaporated under vacuum, and the residue was purified by column chromatography on silica gel (methylene chloride/methanol at 100:1) to yield the title compound 3 as a white solid (564 mg, 49%): m. p. 142~145° C. 479 [M+1]$^+$; $^1$H NMR (DMSO-d$_6$) δ 1.81 (m, 2H), 2.20 (m, 2H), 2.85 (t, 1H, J=2.7 Hz), 4.23 (t, 2H, J=7.2 Hz), 6.05 (s, 2H), 6.36 (s, 2H), 6.68 (s 1H), 6.81 (d, 1H, J=6.0 Hz), 7.48 (s, 1H), 7.72 (d, 1H, J=5.7 Hz).

Example 4

Preparation of 2-(6-iodobenzo[d][1,3]dioxol-5-ylthio)-1-pentyl-1H-imidazo[4,5-c]pyridin-4-amine (Compound 4)

A mixture of compound 0206 (200 mg, 0.485 mmol), 1-bromopentane (110 mg, 0.728 mmol) and Cs$_2$CO$_3$ (268 mg, 0.825 mmol) in DMF (7 mL) was stirred at 85° C. for 2 h. DMF was evaporated under vacuum and the residue was purified by column chromatography on silica gel (methylene chloride/methanol at 100:1) to yield the title compound 4 as a white solid (40 mg, 17%): m. p. 155~160° C. LCMS: 483 [M+1]$^+$; $^1$H NMR (DMSO-d$_6$) δ 0.783 (t, 3H, J=6.6 Hz), 1.22 (m, 4H), 1.58 (m, 2H), 4.15 (t, 2H, J=7.2 Hz), 6.04 (s, 2H), 6.39 (s, 2H), 6.66 (s, 1H), 6.79 (d, 1H, J=5.7 Hz), 7.49 (s, 1H), 7.71 (d, 1H, J=6.0 Hz).

Example 5

Preparation of 2-(7-iodo-2,3-dihydrobenzo[b][1,4]dioxin-6-ylthio)-1-(pent-4-ynyl)-1H-imidazo[4,5-c]pyridin-4-amine (Compound 7)

Step 5a. 6,7-Diiodo-2,3-dihydrobenzo[b][1,4]dioxine (Compound 0107-7)

To a solution of compound 0106 (R=H, n=1) (2 g, 14.7 mmol) in acetonitrile (60 ml) was added NIS (9.92 g, 44.1 mmol) followed by CF$_3$COOH (3.35 g, 29.4 mmol). The mixture was stirred at room temperature overnight. The reaction mixture was concentrated and purified by column chromatography on silica gel (Petroleum ether) to provide the title compound 0107-7 as a white solid (0.7 g, 12%): $^1$H NMR (DMSO-d$_6$) δ 4.21 (s, 4H), 7.34 (s, 2H).

Step 5b. 2-(7-Iodo-2,3-dihydrobenzo[b][1,4]dioxin-6-ylthio)-1-(pent-4-ynyl)-1H-imidazo[4,5-c]pyridin-4-amine (Compound 7)

A mixture of compound 0113 (150 mg, 0.65 mmol), 6,7-Diiodo-2,3-dihydrobenzo[b][1,4]dioxine (0107-7) (Compound 0107) (500 mg, 1.29 mmol), NaOt-Bu (93 mg, 0.97 mmol), neocuproine hydrate (13 mg, 0.065 mmol) and CuI (12 mg, 0.065 mmol) in dry DMF (6 ml) was stirred at 110° C. overnight. The mixture was concentrated and purified first by column chromatography on silica gel (CH2Cl$_2$/MeOH=100/1) and followed by prep-HPLC to give the title compound 7 as a white solid (45 mg, 14%): m.p. 110-118° C. $^1$H NMR (DMSO-d$_6$) δ 1.88 (m, 2H), 2.25 (m, 2H), 2.85 (t, J=2.9 Hz, 1H), 4.24 (m, 4H), 4.36 (t, J=6.9 Hz, 2H), 6.92 (s, 1H), 7.29 (d, J=7.5 Hz, 1H), 7.44 (s, 1H), 7.76 (d, J=6.6 Hz, 1H), 8.47 (s, 2H), 13.01 (s, 1H).

Example 6

Preparation of 2-(2,3-dihydrobenzofuran-5-ylthio)-1-(pent-4-ynyl)-1H-imidazo[4,5-c]pyridin-4-amine (Compound 9)

Step 6a. 4-Amino-1-(4-methoxybenzyl)-1H-imidazo[4,5-c]pyridine-2(3H)-thione (Compound 0205-9)

A mixture of compound 0204 (1.0 g, 3.5 mmol), 5-iodo-2,3-dihydrobenzofuran (0.86 g, 3.5 mmol), neocuproine hydrate (73 mg, 0.35 mmol), CuI (67 mg, 0.35 mmol) and NaOt-Bu (403 mg, 4.2 mmol) in anhydrous DMF (20 mL) was stirred for 24 h at 110° C. (oil bath) under nitrogen atmosphere. The solvent was removed under high vacuum and the crude was purified by column chromatography on silica gel ($CH_2Cl_2$/MeOH=50/1) to give the title compound 0205-9 as a yellow solid (0.38 g, 27%): LCMS: 405 [M+1]$^+$.

Step 6b. 2-(2,3-Dihydrobenzofuran-5-ylthio)-1H-imidazo[4,5-c]pyridin-4-amine (Compound 0206-9)

A mixture of compound 0205-9 (370 mg, 0.915 mmol) and trifluoroacetic acid (10 mL) was stirred at refluxing for 5 h. The solvent was removed and the residue was suspended in saturated aqueous $NaHCO_3$ solution. The resulting solid was collected and dried to give the title compound 0206-9 as a yellow solid (210 mg, 81%): LCMS: 285 [M+1]$^+$.

Step 6c. 2-(2,3-Dihydrobenzofuran-5-ylthio)-1-(pent-4-ynyl)-1H-imidazo[4,5-c]pyridin-4-amine (Compound 9)

A mixture of compound 0206-9 (204 mg, 0.72 mmol), $Cs_2CO_3$ (469 mg, 1.44 mmol), 5-chloropent-1-yne (111 mg, 1.08 mol) and anhydrous DMF (5 mL) was stirred for 2 h at 80° C. The solvent was removed under high vacuum and the crude purified by column chromatography on silica gel ($CH_2Cl_2$/MeOH=100/1) to give the title compound 9 as a pale yellow solid (41 mg, 16%): m.p. 150~157° C., LCMS: 351 [M+1]$^+$. $^1$H NMR (DMSO-$d_6$ δ 1.70) (m, 2H), 2.17 (m, 2H), 2.87 (t, J=2.7 Hz, 1H), 3.14 (t, J=8.7 Hz, 2H), 4.22 (t, J=7.5 Hz, 2H), 4.52 (t, J=8.7 Hz, 2H), 6.31 (s, 2H), 6.77 (m, 2H), 7.20 (dd, $J_1$=1.8 Hz, $J_2$=8.1 Hz, 1H), 7.33 (s, 1H), 7.65 (d, J=4.2 Hz, 1H).

Example 7

Preparation of 2-(benzofuran-5-ylthio)-1-(pent-4-ynyl)-1H-imidazo[4,5-c]pyridin-4-amine (Compound 10)

Step 7a. 2-(Benzofuran-5-ylthio)-1-(4-methoxybenzyl)-1H-imidazo[4,5-c]pyridin-4-amine (Compound 0205-10)

A mixture of compound 0204 (1.0 g, 3.5 mmol), 5-iodobenzofuran (1.2 g, 4.92 mmol), neocuproine hydrate (73 mg, 0.35 mmol), CuI (67 mg, 0.35 mmol) and NaO-t-Bu (403 mg, 4.2 mmol) in anhydrous DMF (20 mL) was stirred for 24 h at 110° C. (oil bath) under nitrogen atmosphere. The solvent was removed under high vacuum and the crude purified by column chromatography on silica gel ($CH_2Cl_2$/MeOH=50/1) to give the title compound 0205-10 as a yellow solid (0.44 g, 31%): LCMS: 403 [M+1]$^+$.

Step 7b. 2-(Benzofuran-5-ylthio)-1H-imidazo[4,5-c]pyridin-4-amine (Compound 0206-10)

A mixture of compound 0205-10 (430 mg, 1.07 mmol) and trifluoroacetic acid (10 mL) was stirred under reflux for 5 h. The solvent was removed and the residue was suspended in saturated aqueous $NaHCO_3$ solution. The resulting solid was collected and dried to give the title compound 0206-10 as a yellow solid (270 mg, 89%): LCMS: 283 [M+1]$^+$.

Step 7c. 2-(Benzofuran-5-ylthio)-1-(pent-4-ynyl)-1H-imidazo[4,5-c]pyridin-4-amine (Compound 10)

A mixture of compound 0206-10 (270 mg, 0.96 mmol), $Cs_2CO_3$ (623 mg, 1.91 mmol), 5-chloropent-1-yne (147 mg, 1.44 mol) and anhydrous DMF (10 mL) was stirred for 2 h at 80° C. The solvent was removed under high vacuum and the crude purified by column chromatography on silica gel ($CH_2Cl_2$/MeOH=100/1) to give the title compound 10 as a pale yellow solid (21 mg, 6%). LCMS: 349 [M+1]$^+$. $^1$H NMR (DMSO-$d_6$ δ 1.73 (m, 2H), 2.17 (m, 2H), 2.87 (t, J=2.4 Hz, 1H), 4.25 (t, J=7.5 Hz, 2H), 6.32 (s, 2H), 6.78 (d, J=5.7 Hz, 1H), 6.96 (d, J=1.5 Hz, 1H), 7.35 (dd, $J_1$=1.8 Hz, $J_2$=8.7 Hz, 1H), 7.61 (d, J=8.7 Hz, 1H), 7.69 (d, J=5.4 Hz, 1H), 7.74 (d, J=1.8 Hz, 1H), 8.04 (d, J=1.8 Hz, 1H).

Example 8

Preparation of 2-(3-methoxyphenylthio)-1-(pent-4-ynyl)-1H-imidazo[4,5-c]pyridin-4-amine (Compound 11)

A mixture of compound 0113 (300 mg, 1.29 mmol), 1-iodo-3-methoxybenzene (0103) (907 mg, 3.87 mmol), neocuproine hydrate (27 mg, 0.129 mmol), CuI (25 mg, 0.129 mmol) and NaOt-Bu (248 mg, 2.58 mmol) in anhydrous DMF (12 mL) was stirred for 24 h at 110° C. (oil bath) under nitrogen atmosphere. The solvent was removed under high vacuum and the crude purified by column chromatography on silica gel ($CH_2Cl_2$/MeOH=100/1) to obtain crude compound which was purified by preparative HPLC to give the title product 11 as a white solid (190 mg, 43.5%): m.p. 139.2~140.6° C., LCMS: 339 [M+1]$^+$; $^1$H NMR (DMSO-$d_6$) δ 1.74 (m, 2H), 2.16 (m, 2H), 2.85 (t, J=2.7 Hz, 1H), 3.72 (s, 3H), 4.24 (t, J=7.5 Hz, 2H), 6.39 (s, 2H), 6.85 (m, 4H), 7.27 (t, J=7.8 Hz, 1H), 7.72 (d, J=6.0 Hz, 1H).

Example 9

Preparation of 2-(2-iodo-5-methoxyphenylthio)-1-(pent-4-ynyl)-1H-imidazo[4,5-c]pyridin-4-amine (Compound 12)

Step 9a. 1,2-Diiodo-4-methoxybenzene (Compound 0104-12)

A mixture of compound 103 (2.0 g, 8.5 mmol), TFA (1.94 g) and NIS (5.74 g, 25.5 mmol) in acetonitrile (60 mL) was stirred at room temperature for 24 h. The solvent was removed under high vacuum and the crude purified by column chromatography on silica gel (petroleum ether) to yield the title compound 104-12 as a colorless liquid (1.2 g, 38%). $^1$H NMR (DMSO-$d_6$) δ 3.75 (s, 3H), 6.77 (m, 1H), 7.49 (d, J=2.7 Hz, 1H), 7.760 (d, J=8.7 Hz, 1H).

Step 9b. 2-(2-Iodo-5-methoxyphenylthio)-1-(pent-4-ynyl)-1H-imidazo[4,5-c]pyridin-4-amine (Compound 12)

A mixture of compound 0113 (230.0 mg, 0.99 mmol), compound 104-12 (535.0 mg, 1.49 mmol), neocuproine hydrate (21.0 mg, 0.10 mmol), CuI (19.0 mg, 0.10 mmol) and NaOt-Bu (95.0 mg, 1.0 mmol) in anhydrous DMF (9.2 mL) was stirred for 24 h at 110° C. (oil bath) under nitrogen atmosphere. The solvent was removed under high vacuum and the crude purified by column chromatography on silica gel ($CH_2Cl_2$/MeOH=100/1) to obtain the title compound 12 as a white solid (75 mg, 16.3%): m.p. 114.5~115.2° C., LCMS: 465 [M+1]$^+$; $^1$H NMR (DMSO-$d_6$) δ 1.80 (m, 2H), 2.17 (m, 2H), 2.81 (t, J=2.1 Hz, 1H), 3.59 (s, 3H), 4.24 (t, J=7.2 Hz, 2H), 6.26 (d, J=2.4 Hz, 1H) 6.45 (s, 2H), 6.68 (m 1H), 6.84 (d, J=5.7 Hz, 1H), 7.75 (d, J=7.2 Hz, 1H), 7.77 (d, J=8.7 Hz, 1H).

Example 10

Preparation of 2-(2-bromo-5-methoxyphenylthio)-1-(pent-4-ynyl)-1H-imidazo[4,5-c]pyridin-4-amine (Compound 13)

Step 10a. 1-Bromo-2-iodo-4-methoxybenzene (Compound 0104-13)

Bromine (0.206 mL, 4.0 mmol) was added dropwise into a solution of compound 0103 (1.0 g, 3.20 mmol) in acetic acid (4.5 mL) with constant stirring overnight. Water (15 mL) was then added to the reaction mixture, and the product was extracted into hexane (3×7.5 mL). The combined organic layers were washed with 5% sodium sulfite (7.5 mL) and brine (7.5 mL), dried over magnesium sulfite, filtered and concentrated to leave an oily solid which was purified by chromatography on silica gel (petroleum) to yield the title product 0104-13 as a colorless oil (0.5 g, 37%): $^1$H NMR (CDCl$_3$) δ 3.769 (s, 3H), 6.77 (dd, 1H, $J_1$=3.0 Hz, $J_2$=8.7 Hz), 7.39 (d, 1H, J=3.0 Hz), 7.47 (d, 1H, J=9.0 Hz).

Step 10b. 2-(2-Bromo-5-methoxyphenylthio)-1-(pent-4-ynyl)-1H-imidazo[4,5-c]pyridin-4-amine (Compound 13)

A mixture of compound 0113 (174 mg, 0.75 mmol), compound 0104-13 (469 mg, 1.5 mmol), neocuproine hydrate (16 mg, 0.075 mmol), CuI (14 mg, 0.075 mmol) and NaOt-Bu (96 mg, 1.0 mmol) in anhydrous DMF (8 mL) was stirred for 24 h at 110° C. (oil bath) under nitrogen atmosphere. The solvent was removed under high vacuum and the crude purified by column chromatography on silica gel ($CH_2Cl_2$/MeOH at 100/1) to obtain the title compound 13 as a yellow solid (60 mg, 19%): LCMS: 417 [M+1]$^+$; $^1$H NMR (DMSO-$d_6$) δ 1.88 (m, 2H), 2.23 (m, 2H), 2.81 (t, 1H, J=2.4 Hz), 3.68 (s, 3H), 4.39 (t, 2H, J=7.2 Hz), 6.71 (d, 1H, J=2.7 Hz), 6.91 (dd, 1H, $J_1$=2.7 Hz, $J_2$=9.3 Hz), 7.31 (d 1H, J=6.9 Hz), 7.65 (d, 1H, J=9.0 Hz), 7.78 (d, 1H, J=7.2 Hz), 8.63 (s, 2H), 13.248 (s, 1H).

Example 11

Preparation of 2-(2-chloro-5-methoxyphenylthio)-1-(pent-4-ynyl)-1H-imidazo[4,5-c]pyridin-4-amine (Compound 14)

Step 11a. 1-Chloro-2-iodo-4-methoxybenzene (Compound 0104-14)

A solution of 0103 (1 g, 4.27 mmol) and NCS (2.25 g, 17.09 mmol) in anhydrous DMF (24 mL) was stirred at room temperature for 2.5 h. After reaction, the solvent was removed and the crude was purified by silica gel column purification (petroleum) to give the title product 0104-14 as a colorless oil (440 mg, 38%): $^1$H NMR (DMSO-$d_6$) δ 3.76 (s, 3H), 7.00 (dd, 1H, $J_1$=2.7 Hz, $J_2$=8.4 Hz), 7.47 (m, 2H).

Step 11b. 2-(2-Chloro-5-methoxyphenylthio)-1-(pent-4-ynyl)-1H-imidazo[4,5-c]pyridin-4-amine (Compound 14)

A mixture of compound 0113 (150 mg, 0.646 mmol), compound 0104-14 (260 mg, 0.969 mmol), neocuproine hydrate (13 mg, 0.065 mmol), CuI (12 mg, 0.065 mmol) and NaOt-Bu (62 mg, 0.646 mmol) in anhydrous DMF (6 mL) was stirred for 24 h at 110° C. (oil bath) under nitrogen atmosphere. The solvent was removed under high vacuum and the crude purified by column chromatography on silica gel ($CH_2Cl_2$/MeOH at 100/1) to obtain the title compound 14 as a white solid (25 mg, 10%). LCMS: 373 [M+1]$^+$; $^1$H NMR (DMSO-$d_6$) δ 1.80 (m, 2H), 2.16 (m, 2H), 2.83 (s, 1H), 3.62 (s, 3H), 4.26 (t, 2H, J=7.2 Hz), 6.38 (d, 1H, J=2.1 Hz), 6.48 (s, 2H), 6.85 (d 1H, J=6.6 Hz), 6.91 (dd, 1H, $J_1$=1.8 Hz, $J_2$=7.8 Hz), 7.48 (d, 1H, J=9.9 Hz), 7.74 (d, 1H, J=5.7 Hz).

Example 12

Preparation of 2-(2-iodo-4,5-dimethoxyphenylthio)-1-(pent-4-ynyl)-1H-imidazo[4,5-c]pyridin-4-amine (Compound 15)

Step 12a. 1,2-Diiodo-4,5-dimethoxybenzene (Compound 0104-15)

To a solution of 1,2-dimethoxybenzene (2 g, 14.5 mmol) in anhydrous DMF (60 mL) was added NCS (9.67 g, 43.4 mmol) followed by trifluoroacetic acid (3.3 g, 28.9 mmol). The reaction was stirred at room temperature overnight. The solution was concentrated and purified by column chromatography on silica gel (petroleum ether) to provide the title compound 0104-15 as a white solid (1.9 g, 34%): $^1$H NMR (DMSO-$d_6$) δ 3.71 (s, 6H), 7.31 (s, 2H).

Step 12b. 2-(2-Iodo-4,5-dimethoxyphenylthio)-1-(pent-4-ynyl)-1H-imidazo[4,5-c]pyridin-4-amine (Compound 15)

A mixture of 0113 (150 mg, 0.65 mmol), compound 0104-15 (503 mg, 1.29 mmol), NaOt-Bu (93 mg, 0.97 mmol), neocuproine hydrate (13 mg, 0.065 mmol), and CuI (12 mg, 0.065 mmol) in dry DMF (6 ml) was stirred at 110° C. overnight. The mixture was concentrated and first purified by column chromatography on silica gel ($CH_2Cl_2$/MeOH=100/1) and then by prep-HPLC to give the title product 15 as a white solid (40 mg, 13%): m.p. 134-140° C. $^1$H NMR (DMSO-$d_6$) δ 1.88 (m, 2H), 2.26 (m, 2H), 2.86 (t, J=2.4 Hz, 1H), 3.67 (s, 3H), 3.80 (s, 3H), 4.37 (t, J=7.4 Hz, 2H), 7.13 (s, 1H), 7.29 (d, J=6.9 Hz, 1H), 7.44 (s, 1H), 7.75 (d, J=6.3 Hz, 1H), 8.42 (s, 2H), 13.13 (s, 1H).

Example 13

Preparation of 4-(4-amino-1-(pent-4-ynyl)-1H-imidazo[4,5-c]pyridin-2-ylthio)-5-iodobenzene-1,2-diol (Compound 16)

To a solution of compound 3 (120 mg, 0.251 mmol) in dichloromethane (24 mL) was added dropwise the solution of BCl₃ in dichloromethane (0.755 mL, 1M) at room temperature under nitrogen. The mixture was stirred for 30 min. and methanol (50 mL) was added. The mixture was heated to reflux temperature for 1 h. The reaction was evaporated and the resulting residue was purified by pre-HPLC to obtain the title compound 16 as a white solid (35 mg, 30%): m.p. 107~115° C. LCMS: 467 [M+1]$^+$; $^1$H NMR (DMSO-d$_6$) δ 1.88 (m, 2H), 2.25 (m, 2H), 2.84 (t, 1H, J=2.1 Hz), 4.33 (t, 2H, J=6.6 Hz), 6.81 (s, 1H), 7.27 (m, 2H), 7.75 (d, 1H, J=7.2 Hz), 8.48 (s, 2H), 9.56 (s, 1H), 9.82 (s, 1H), 13.16 (s, 1H).

Example 14

Preparation of 2-(5-methoxy-2-nitrophenylthio)-1-(pent-4-ynyl)-1H-imidazo[4,5-c]pyridin-4-amine (Compound 17)

A mixture of compound 0113 (150 mg, 0.646 mmol), 1-iodo-5-methoxy-2-nitrobenzene (199 mg, 0.713 mmol), neocuproine hydrate (13 mg, 0.065 mmol), CuI (12 mg, 0.065 mmol) and NaOt-Bu (62 mg, 0.646 mmol) in anhydrous DMF (6 mL) was stirred for 24 h at 110° C. (oil bath) under nitrogen atmosphere. The solvent was removed under high vacuum and the crude purified by column chromatography on silica gel (CH$_2$Cl$_2$/MeOH at 100/1) to obtain target compound 17 as a light yellow solid (60 mg, 24%): LCMS: 384 [M+1]$^+$; $^1$H NMR (DMSO-d$_6$) δ 1.77 (m, 2H), 2.14 (m, 2H), 2.73 (t, 1H, J=2.4 Hz), 3.69 (s, 3H), 4.24 (t, 2H, J=6.9 Hz), 6.04 (d, 1H, J=2.4 Hz), 6.63 (s, 2H), 6.88 (d 1H, J=6.0 Hz), 7.07 (dd, 1H, J$_1$=2.4 Hz, J$_2$=9.3 Hz), 7.78 (d, 1H, J=6.0 Hz), 8.37 (d, 1H, J=9.3 Hz).

Example 15

Preparation of 2-(4-amino-1-(pent-4-ynyl)-1H-imidazo[4,5-c]pyridin-2-ylthio)-4-methoxybenzonitrile (Compound 18)

The title compound 18 was prepared as a white solid (25 mg, 11%) from compound 0113 (150 mg, 0.646 mmol), 2-iodo-4-methoxybenzonitrile (251 mg, 0.969 mmol), neocuproine hydrate (13 mg, 0.0646 mmol), CuI (12 mg, 0.0646 mmol) and NaOt-Bu (62 mg, 0.646 mmol) in anhydrous DMF (6 mL) using a procedure similar to that described for compound 17 (Example 14): LCMS: 364 [M+1]$^+$; $^1$H NMR (DMSO-d$_6$) δ 1.84 (m, 2H), 2.20 (m, 2H), 2.83 (t, 1H, J=2.7 Hz), 3.76 (s 3H), 4.29 (t, 2H, J=7.5 Hz), 6.41 (s, 2H), 6.77 (s, 2H J=2.4 Hz), 6.86 (m, 1H), 7.08 (dd, 1H, J$_1$=2.4 Hz, J$_2$=9.0 Hz), 7.75 (m, 1H), 7.90 (d, 1H, J=8.1 Hz).

Example 16

Preparation of 1-(2-(4-amino-1-(pent-4-ynyl)-1H-imidazo[4,5-c]pyridin-2-ylthio)-4-methoxyphenyl)ethanone (Compound 19)

Step 16a. 1-(2-Iodo-4-methoxyphenyl)ethanone (Compound 0104-19)

Anhydrous AlCl$_3$ (1.284 g, 9.6 mmol) was added to the mixture of 0103 (1.0 g, 4.28 mmol) and CS$_2$ (4 ml). The resulting mixture was heated at reflux (56° C.) and then Ac$_2$O (0.35 g, 3.42 mmol) was added slowly into the mixture. The mixture was kept refluxing for 1.5 h. and then CS$_2$ was removed under reduce pressure. The black residue was poured to ice-concentrated HCl, and extracted with ether three times. The extract was washed with H$_2$O (100 ml×2), 10% NaOH (100 ml×2), and washed again with water until the water layer was colorless. The organic layer was then washed with brine, dried over anhydrous NaSO$_4$ and evaporated. The crude product was purified by column chromatography on silica gel (AcOEt/petroleum=1:5) to give the title compound 0104-19 as a pale red oil (160 mg, 14%): $^1$H NMR (CDCl$_3$) δ 2.60 (s, 3H), 3.83 (s, 3H), 6.92 (dd, 1H, J$_1$=2.4 Hz, J$_2$=8.7 Hz), 7.51 (d, 1H, J=2.4 Hz), 7.58 (d, 1H, J=8.7 Hz).

Step 16b. 1-(2-(4-Amino-1-(pent-4-ynyl)-1H-imidazo[4,5-c]pyridin-2-ylthio)-4-methoxyphenyl)ethanone (Compound 19)

The title compound 19 was prepared as a yellow solid (78 mg, 31.7%) from compound 0113 (150 mg, 0.646 mmol), compound 0104-19 (160 mg, 0.579 mmol), neocuproine hydrate (15 mg, 0.0715 mmol), CuI (14 mg, 0.0715 mmol) and NaOt-Bu (69 mg, 0.715 mmol) in anhydrous DMF (6 mL) using a procedure similar to that described for compound 17 (Example 14): LCMS: 381 [M+1]$^+$; $^1$H NMR (DMSO-d$_6$) δ 1.75 (m, 2H), 2.12 (m, 2H), 2.619 (s 3H), 2.77 (t, 1H, J=2.4 Hz), 3.63 (s, 3H), 4.18 (t, 2H, J=7.2 Hz), 5.92 (d, 1H, J=2.1 Hz), 6.49 (s, 2H), 6.85 (d 1H, J=6.0 Hz), 6.93 (dd, 1H, J$_1$=2.4 Hz, J$_2$=8.4 Hz), 7.75 (d, 1H, J=6.0 Hz), 8.13 (d, 1H, J=8.4 Hz).

Example 17

Preparation of 2-(5-fluoro-2-iodophenylthio)-1-(pent-4-ynyl)-1H-imidazo[4,5-c]pyridin-4-amine (Compound 20)

Step 17a. 2-(5-Fluoro-2-iodophenylthio)-1-(4-methoxybenzyl)-1H-imidazo[4,5-c]pyridin-4-amine (Compound 0205-20)

A mixture of compound 0204 (286 mg, 1.01 mmol), 4-fluoro-1,2-diiodobenzene (447 mg, 1.2 mmol), NaOt-Bu (96 mg, 1 mmol), neocuproine hydrate (21 mg, 0.1 mmol), and CuI (19 mg, 0.1 mmol) in dry DMF (9 mL) was stirred at 110° C. overnight. The mixture was concentrated and purified by column chromatography on silica gel (CH$_2$Cl$_2$/MeOH=100/1) to give the title compound 0205-20 as a white solid (260 mg, 51%): LCMS: 507 [M+1]$^+$; $^1$H NMR (DMSO-d$_6$): δ 3.68 (s, 3H), 5.40 (s, 2H), 6.32 (dd, 1H, J$_1$=2.7 Hz, J$_2$=9.9 Hz), 6.56 (s, 2H), 6.75 (d, 2H, J=8.7 Hz), 6.85 (m, 1H), 6.90 (d, 1H, J=5.7 Hz), 7.07 (d, 2H, J=8.7 Hz), 7.76 (d, 1H, J=5.7 Hz), 7.85 (m, 2H).

Step 17b. 2-(5-Fluoro-2-iodophenylthio)-1H-imidazo[4,5-c]pyridin-4-amine (Compound 0206-20)

A mixture of compound 0205-20 (330 mg, 0.65 mmol), trifluoroacetic acid (3 mL) was stirred at reflux for 2 h. The solvent was removed and the residue was suspended in saturated aqueous NaHCO$_3$ solution. The resulting solid was collected and dried to give the title compound 0206-20 as a white solid (250 mg, 98%): LCMS: 387 [M+1]$^+$; $^1$H NMR (DMSO-d$_6$): δ 6.91 (d, 2H, J=6.3 Hz), 6.96 (m, 1H), 7.09 (dd, 1H, J$_1$=3 Hz, J$_2$=8.4 Hz), 7.56 (d, 1H, J=6.9 Hz), 7.85 (s, 2H), 7.92 (m, 1H).

Step 17c. 2-(5-Fluoro-2-iodophenylthio)-1-(pent-4-ynyl)-1H-imidazo[4,5-c]pyridin-4-amine (Compound 20)

A mixture of compound 0206-20 (100 mg, 0.26 mmol), Cs$_2$CO$_3$ (169 mg, 0.52 mmol), 5-chloropent-1-yne (40 mg, 0.39 mmol) and anhydrous DMF (5 mL) was stirred for 24 h at 80° C. The solvent was removed under high vacuum and the crude product was purified by column chromatography on silica gel (CH$_2$Cl$_2$/MeOH=20/1) to give the crude product as a pale white solid which was further purified by prep-HPLC to give the title compound 20 as a white solid (15 mg, 13%): LCMS: 453 [M+1]$^+$; $^1$H NMR (DMSO-d$_6$): δ 2.04 (m, 2H), 2.18 (t, 2H, J=7.2 Hz), 2.80 (s, 1H), 4.26 (t, 2H, J=7.5 Hz), 6.48 (s, 2H), 6.61 (dd, 1H, J$_1$=3 Hz, J$_2$=9.6 Hz,), 6.86 (d, 1H, J=6 Hz), 6.94 (m, 1H), 7.76 (d, 1H, J=6 Hz), 7.93 (s, 2H).

Example 18

Preparation of 2-(4,5-difluoro-2-iodophenylthio)-1-(pent-4-ynyl)-1H-imidazo[4,5-c]pyridin-4-amine (Compound 21)

Step 18a. 2-(4,5-Difluoro-2-iodophenylthio)-1-(4-methoxybenzyl)-1H-imidazo[4,5-c]pyridin-4-amine (Compound 0205-21)

The title compound 0205-21 was prepared (130 mg 14%) from compound 0204 (500 mg, 1.75 mmol), 1,2-difluoro-4,5-diiodobenzene (1277 mg, 3.49 mmol), NaOt-Bu (251 mg, 2.62 mmol), neocuproine hydrate (36 mg, 0.175 mmol), and CuI (33 mg, 0.175 mmol) in dry DMF (12 mL) using a procedure similar to that described for compound 0205-20 (Example 17): LCMS: 525 [M+1]$^+$.

Step 18b. 2-(4,5-Difluoro-2-iodophenylthio)-1H-imidazo[4,5-c]pyridin-4-amine (Compound 0206-21)

The title compound 0206-21 was prepared (140 mg, 76%) from compound 0205-21 (240 mg, 0.46 mmol) and CF$_3$COOH (4 mL) using a procedure similar to that described for compound 0206-20 (Example 17): LCMS: 405 [M+1]$^+$.

Step 18c. 2-(4,5-Difluoro-2-iodophenylthio)-1-(pent-4-ynyl)-1H-imidazo[4,5-c]pyridin-4-amine (Compound 21)

The title compound 21 was prepared (25 mg, 18%) from compound 0206-21 (120 mg, 0.30 mmol), 5-chloropent-1-yne (46 mg, 0.45 mmol), Cs$_2$CO$_3$ (164 mg, 0.50 mmol) and KI (5 mg) in DMF (5 mL) using a procedure similar to that described for compound 20 (Example 17): m.p: 105-110° C. LCMS: 471 [M+1]$^+$. 1H NMR: (DMSO-d$_6$) δ 1.83 (m, 2H), 2.19 (m, 2H), 2.83 (t, J=2.7 Hz, 1H), 4.25 (t, J=7.2 Hz, 2H), 6.43 (s, 2H), 6.84 (d, J=5.7 Hz, 1H), 7.05 (m, 1H), 7.73 (d, J=6.0 Hz, 1H), 8.06 (m, 1H).

Example 19

Preparation of 2-(6-bromobenzo[d][1,3]dioxol-5-ylthio)-1-(but-3-ynyl)-1H-imidazo[4,5-c]pyridin-4-amine (Compound 22)

Step 19a. 2-(6-Bromobenzo[d][1,3]dioxol-5-ylthio)-1-(4-methoxybenzyl)-1H-imidazo[4,5-c]pyridin-4-amine (Compound 0205-22)

The title compound 0205-22 was prepared as a brown solid (584 mg, 49%) from compound 0204 (700 mg, 2.44 mmol), 5-bromo-6-iodobenzo[d][1,3]dioxole (1.20 g, 3.66 mmol), neocuproine hydrate (51 mg, 0.244 mmol), CuI (46 mg, 0.244 mmol) and NaOt-Bu (234 mg, 2.44 mmol) in anhydrous DMF (31 mL) using a procedure similar to that described for compound 0205-20 (Example 17): LCMS: 485 [M+1]$^+$; $^1$H NMR (DMSO-d$_6$) δ 3.69 (s, 3H), 5.35 (s, 2H), 6.04 (s, 2H), 6.54 (s, 1H), 6.81 (m, 4H), 7.06 (d, 2H, J=8.7 Hz), 7.29 (s, 1H).

Step 19b. 2-(6-Bromobenzo[d][1,3]dioxol-5-ylthio)-1H-imidazo[4,5-c]pyridin-4-amine (Compound 0206-22)

The title compound 0206-22 was prepared as a yellow solid (308 mg, 74%) from compound 0205-22 (557 mg, 1.15 mmol) and TFA (4 mL) using a procedure similar to that described for compound 0206-20 (Example 17): LCMS: 365 [M+1]$^+$; $^1$H NMR (DMSO-d$_6$) δ 6.07 (s, 2H), 6.58 (s, 2H), 6.69 (d, 1H, J=6.0 Hz), 6.98 (s, 1H), 7.34 (s, 1H), 7.47 (d, 1H, J=6.0 Hz).

Step 19c. 2-(6-Bromobenzo[d][1,3]dioxol-5-ylthio)-1-(but-3-ynyl)-1H-imidazo[4,5-c]pyridin-4-amine (Compound 22)

A solution of 0206-22 (200 mg, 0.548 mmol), PPh$_3$ (287 mg, 1.10 mmol), but-3-yn-1-ol (50 mg, 0.712 mmol), DIAD (332 mg, 1.644 mmol) in toluene (4 mL) and CH$_2$Cl$_2$ (1 mL) was stirred at room temperature for 20 min. The solvent was removed under vacuum and the crude purified by column chromatography on silica gel (CH$_2$Cl$_2$/MeOH at 30/1) and followed by pre-HPLC to give the title product 22 as a white solid (82 mg, 36%): m. p. 154~158° C. LCMS: 417 [M+1]$^+$; $^1$H NMR (DMSO-d$_6$) δ 2.64 (m, 2H), 2.86 (m, 1H), 4.38 (t, 2H, J=6.3 Hz), 6.07 (s, 2H), 6.40 (s, 2H), 6.66 (s, 1H), 6.87 (d, 1H, J=5.7 Hz), 7.35 (s, 1H), 7.71 (d, 1H, J=5.4 Hz).

Example 20

Preparation of 1-(but-3-ynyl)-2-(6-iodobenzo[d][1,3]dioxol-5-ylthio)-1H-imidazo[4,5-c]pyridin-4-amine (Compound 23)

The title compound 23 was prepared as a white solid (134 mg, 39.6%) from compound 0206-3 (300 mg, 0.727 mmol), PPh$_3$ (381 mg, 1.46 mmol), but-3-yn-1-ol (66 mg, 0.946 mmol), DIAD (441 mg, 2.18 mmol) in toluene (6 mL) and CH$_2$Cl$_2$ (1.5 mL) using a procedure similar to that described for compound 22 (Example 19): m. p. 201~204° C. LCMS: 465 [M+1]$^+$; $^1$H NMR (DMSO-d$_6$) δ 2.73 (m, 2H), 2.92 (t, 1H, J=2.7 Hz), 4.50 (t, 2H, J=6.6 Hz), 6.10 (s, 2H), 6.97 (s, 1H), 7.37 (d, 1H, J=6.6 Hz), 7.52 (s, 1H), 7.76 (d, 1H, J=9.0 Hz), 8.58 (d, 2H, J=8.7 Hz), 13.29 (s, 1H).

Example 21

Preparation of 2-(6-bromobenzo[d][1,3]dioxol-5-ylthio)-1-(hex-5-ynyl)-1H-imidazo[4,5-c]pyridin-4-amine (Compound 24)

The title compound 24 was prepared as a white solid (67 mg, 27%) from compound 0206-22 (200 mg, 0.548 mmol), PPh$_3$ (287 mg, 1.10 mmol), hex-5-yn-1-ol (70 mg, 0.712 mmol), DIAD (332 mg, 1.643 mmol) in toluene (5 mL) and CH$_2$Cl$_2$ (1.5 mL) using a procedure similar to that described for compound 22 (Example 19): LCMS: 445 [M+1]$^+$; $^1$H NMR (DMSO-d$_6$) δ 1.44 (m, 2H), 1.78 (m, 2H), 2.17 (m, 2H), 2.77 (t, 1H, J=2.7 Hz), 4.32 (t, 2H, J=6.9 Hz), 6.13 (s, 2H), 7.02 (s, 1H), 7.30 (d, 1H, J=6.6 Hz), 7.42 (s, 1H), 7.75 (d, 1H, J=6.6 Hz), 8.54 (s, 2H), 13.26 (s, 1H).

Example 22

Preparation of 1-(hex-5-ynyl)-2-(6-iodobenzo[d][1,3]dioxol-5-ylthio)-1H-imidazo[4,5-c]pyridin-4-amine (Compound 25)

The title compound 25 was prepared as a white solid (90 mg, 25%) from compound 0206-3 (300 mg, 0.727 mmol), PPh$_3$ (381 mg, 1.46 mmol), hex-5-yn-1-ol (93 mg, 0.946 mmol), DIAD (441 mg, 2.18 mmol) in toluene (6 mL) and CH$_2$Cl$_2$ (1.5 mL) using a procedure similar to that described for compound 22 (Example 19): m. p. 158~162° C. LCMS: 493 [M+1]$^+$; $^1$H NMR (DMSO-d$_6$) δ 1.45 (m, 2H), 1.77 (m, 2H), 2.18 (m, 2H), 2.77 (t, 1H, J=2.7 Hz), 4.31 (t, 2H, J=7.2 Hz), 6.10 (s, 2H), 7.00 (s, 1H), 7.31 (d, 1H, J=7.5 Hz), 7.54 (s, 1H), 7.75 (d, 1H, J=7.2 Hz), 8.56 (d, 2H, J=8.7 Hz), 13.25 (s, 1H).

Example 23

Preparation of 4-(4-amino-2-(2-iodo-5-methoxyphenylthio)-1H-imidazo[4,5-c]pyridin-1-yl)butanenitrile (Compound 26)

Step 23a. 2-(2-Iodo-5-methoxyphenylthio)-1-(4-methoxybenzyl)-1H-imidazo[4,5-c]pyridin-4-amine (Compound 0205-26)

The title compound 0205-26 was prepared as a brown solid (734 mg, 55%) from compound 0204 (1 g, 3.5 mmol), 1,2-diiodo-3-methoxybenzene (1.5 g, 4.2 mmol), neocuproine hydrate (73 mg, 0.35 mmol), CuI (66 mg, 0.35 mmol) and NaOt-Bu (335 mg, 3.5 mmol) in anhydrous DMF (33 mL) using a procedure similar to that described for compound 0205-20 (Example 17): LCMS: 519[M+1]$^+$.

Step 23b. 2-(2-Iodo-5-methoxyphenylthio)-1H-imidazo[4,5-c]pyridin-4-amine (Compound 0206-26)

The title compound 0206-26 was prepared as a yellow solid (181 mg, 53%) from compound 0205-26 (443 mg, 0.85 mmol) and TFA (4 mL) using a procedure similar to that described for compound 0206-20 (Example 17): LCMS: 399 [M+1]$^+$; $^1$H NMR (DMSO-d$_6$) δ 3.61 (s, 3H), 6.72 (m, 5H), 7.51 (d, 1H, J=6.3 Hz), 7.74 (d, 1H, J=8.7 Hz).

Step 23c. 4-(4-Amino-2-(2-iodo-5-methoxyphenylthio)-1H-imidazo[4,5-c]pyridin-1-yl)butanenitrile (Compound 26)

A mixture of compound 0206-26 (150 mg, 0.38 mmol), 4-bromobutanenitrile (83.6 mg, 0.565 mmol), Cs$_2$CO$_3$ (208 mg, 0.64 mmol) in DMF (5 mL) was stirred at 80° C. for 2 h. The mixture was evaporated to remove DMF and purified first by column chromatography on silica gel (CH$_2$Cl$_2$/MeOH at 100/1) and then by pre-HPLC to yield the title compound 26 as a white solid (20 mg, 11.3%): m. p. 146~150° C. LCMS: 466 [M+1]$^+$; $^1$H NMR (DMSO-d$_6$) δ 1.95 (m, 2H), 2.54 (m, 2H), 3.59 (s, 3H), 4.24 (t, 2H, J=7.5 Hz), 6.31 (d, 1H, J=3.3 Hz), 6.48 (s, 2H), 6.69 (dd, 1H, J$_1$=2.7 Hz, J$_2$=8.7 Hz), 6.85 (d, 1H, J=6.0 Hz), 7.77 (m, 2H).

Example 24

Preparation of 4-(4-amino-2-(6-bromobenzo[d][1,3]dioxol-5-ylthio)-1H-imidazo[4,5-c]pyridin-1-yl)butanenitrile (Compound 27)

The title compound 27 was prepared as a light yellow solid (43 mg, 24%) from compound 0206-22 (150 mg, 0.411 mmol), 4-bromobutanenitrile (91 mg, 0.616 mmol), Cs$_2$CO$_3$ (227 mg, 0.699 mmol) in DMF (6 mL) using a procedure similar to that described for compound 26 (Example 23): m. p. 140~149° C. LCMS: 432 [M+1]$^+$; $^1$H NMR (DMSO-d$_6$) δ 1.96 (m, 2H), 2.56 (t, 2H, J=7.2 Hz), 4.25 (t, 2H, J=7.8 Hz), 6.08 (s, 2H), 6.39 (s, 2H), 6.70 (s, 1H), 6.83 (d, 1H, J=8.4 Hz), 7.36 (s, 1H), 7.73 (d, 1H, J=5.7 Hz).

Example 25

Preparation of 4-(4-amino-2-(6-iodobenzo[d][1,3]dioxol-5-ylthio)-1H-imidazo[4,5-c]pyridin-1-yl)butanenitrile (Compound 28)

The title compound 28 was prepared as a white solid (82 mg, 39%) from compound 0206-3 (180 mg, 0.437 mmol), 4-bromobutanenitrile (97 mg, 0.655 mmol), Cs$_2$CO$_3$ (241 mg, 0.743 mmol) in DMF (6.3 mL) using a procedure similar to that described for compound 26 (Example 23): m. p. 210~222° C. LCMS: 480 [M+1]$^+$; $^1$H NMR (DMSO-d$_6$) δ 2.05 (m, 2H), 2.62 (t, 2H, J=7.2 Hz), 4.36 (t, 2H, J=7.2 Hz), 6.10 (s, 2H), 7.00 (s, 1H), 7.30 (d, 1H, J=7.5 Hz), 7.53 (s, 1H), 7.77 (d, 1H, J=6.9 Hz), 8.52 (s, 2H), 13.07 (s, 1H).

Example 26

Preparation of 5-(4-amino-2-(6-bromobenzo[d][1,3]dioxol-5-ylthio)-1H-imidazo[4,5-c]pyridin-1-yl)pentanenitrile (Compound 29)

The title compound 29 was prepared as a light yellow solid (68 mg, 37%) from compound 0206-22 (150 mg, 0.411 mmol), 5-bromopentanenitrile (100 mg, 0.616 mmol), Cs$_2$CO$_3$ (227 mg, 0.699 mmol) in DMF (6 mL) using a procedure similar to that described for compound 26 (Example 23): m. p. 133~135° C. LCMS: 446 [M+1]$^+$; $^1$H NMR (DMSO-d$_6$) δ 1.51 (m, 2H), 1.73 (m, 2H), 2.50 (m, 2H), 4.21 (t, 2H, J=6.6 Hz), 6.07 (s, 2H), 6.38 (s, 2H), 6.69 (s, 1H), 6.84 (d, 1H, J=7.5 Hz), 7.36 (s, 1H), 7.72 (d, 1H, J=6.0 Hz).

Example 27

Preparation of 5-(4-amino-2-(6-iodobenzo[d][1,3]dioxol-5-ylthio)-1H-imidazo[4,5-c]pyridin-1-yl)pentanenitrile (Compound 30)

The title compound 30 was prepared as a white solid (92 mg, 48%) from compound 0206-3 (162 mg, 0.393 mmol), 5-bromopentanenitrile (96 mg, 0.590 mmol), Cs$_2$CO$_3$ (217 mg, 0.668 mmol) in DMF (5.7 mL) using a procedure similar to that described for compound 26 (Example 23): m. p. 179~191° C. LCMS: 494 [M+1]$^+$; $^1$H NMR (DMSO-d$_6$) δ 1.58 (m, 2H), 1.80 (m, 2H), 2.53 (m, 2H), 4.33 (t, 2H, J=6.6 Hz), 6.10 (s, 2H), 7.02 (s, 1H), 7.33 (d, 1H, J=7.5 Hz), 7.54 (s, 1H), 7.77 (d, 1H, J=7.2 Hz), 8.55 (s, 2H), 13.21 (s, 1H).

Example 28

Preparation of 1-(2-aminoethyl)-2-(6-iodobenzo[d][1,3]dioxol-5-ylthio)-1H-imidazo[4,5-c]pyridin-4-amine (Compound 32)

Step 28a. 2-(2-(4-Amino-2-(6-iodobenzo[d][1,3]dioxol-5-ylthio)-1H-imidazo[4,5-c]pyridin-1-yl)ethyl)isoindoline-1,3-dione (Compound 0302-32)

A mixture of compound 0206-3 (500 mg, 1.2 mmol), 2-(2-bromoethyl)isoindoline-1,3-dione (457 mg, 1.8 mmol) and $Cs_2CO_3$ (672 mg, 2.1 mmol) in anhydrous DMF (8 mL) was stirred at 50° C. for 4 h. The reaction mixture was cooled to room temperature and filtered. The filtrate was evaporated under high vacuum to give a crude product as an orange solid which was purified by column chromatography on silica gel ($CH_2Cl_2$/MeOH=100/1) to provide the title compound 0302-32 as a pale yellow solid (390 mg, 56%): LC-MS: 586 [M+1]$^+$. $^1$H NMR (300 MHz, DMSO-$d_6$) δ 3.92 (t, 2H, J=5.3 Hz), 4.50 (t, 2H, J=5.3 Hz), 6.00 (s, 2H), 6.38 (s, 2H), 6.49 (s, 1H), 6.75 (d, 1H, J=6.0 Hz), 7.19 (s, 1H), 7.64 (d, 1H, J=6.0 Hz), 7.73 (m, 4H).

Step 28b. 1-(2-Aminoethyl)-2-(6-iodobenzo[d][1,3]dioxol-5-ylthio)-1H-imidazo[4,5-c]pyridin-4-amine (Compound 32)

A mixture of compound 0302-32 (5 g, 8.55 mmol) and $N_2H_4$—$H_2O$ (4.28 g, 85.5 mmol) in $CH_2Cl_2$ (150 mL) and EtOH (15 mL) was stirred at 50° C. for 2 h. The solid was removed by filtration and the filtrate was washed with brine (100 mL×2), dried over $Na_2SO_4$, filtered and evaporated to give the title compound 32 as a white solid (3 g, 77%): m. p. 111~121° C. LC-MS: 456 [M+1]$^+$. $^1$H NMR (300 MHz, DMSO-$d_6$) δ 1.46 (s, 2H) 2.80 (t, 2H, J=6.3 Hz), 4.16 (t, 2H, J=6.6 Hz), 6.05 (s, 2H), 6.29 (s, 2H), 6.69 (s, 1H), 6.84 (d, 1H, J=6.0 Hz), 7.46 (s, 1H), 7.70 (d, 1H, J=5.7 Hz).

Example 29

Preparation of 2-(6-bromobenzo[d][1,3]dioxol-5-ylthio)-1-(2-(neopentylamino)ethyl)-1H-imidazo[4,5-c]pyridin-4-amine (Compound 33)

Step 29a. 2-(2-(4-Amino-2-(6-bromobenzo[d][1,3]dioxol-5-ylthio)-1H-imidazo[4,5-c]pyridin-1-yl)ethyl)isoindoline-1,3-dione (Compound 0302-33)

The title compound 0302-33 was prepared as a pale yellow solid (720 mg, 50%) from compound 0206-22 (975 mg, 2.67 mmol), 2-(2-bromoethyl)isoindoline-1,3-dione (1.017 g, 4.00 mmol), $Cs_2CO_3$ (1.475 g, 4.54 mmol) in anhydrous DMF (38 mL) using a procedure similar to that described for compound 0302-32 (Example 28): LCMS: 538 [M+1]$^+$.

Step 29b. 1-(2-Aminoethyl)-2-(6-bromobenzo[d][1,3]dioxol-5-ylthio)-1H-imidazo[4,5-c]pyridin-4-amine (Compound 0303-33)

The title compound 0303-33 was prepared as a pale yellow solid (495 mg, 91%) from compound 0302-33 (720 mg, 1.337 mmol) and $N_2H_4$—$H_2O$ (886 mg, 14.71 mmol) in $CH_2Cl_2$ (27 mL) and EtOH (3 mL) using a procedure similar to that described for compound 0303-32 (Example 28): LCMS: 408 [M+1]$^+$.

Step 29c. 2-(6-Bromobenzo[d][1,3]dioxol-5-ylthio)-1-(2-(neopentylamino)ethyl)-1H-imidazo[4,5-c]pyridin-4-amine (Compound 33)

To a solution of compound 0303-33 (150 mg, 0.613 mmol) in methanol (10 mL) was added pivalaldehyde (63 mg, 0.736 mmol). After the mixture was stirred for 30 min at room temperature, $NaBH_3CN$ (154 mg, 2.452 mmol) was added slowly, and the mixture was stirred for additional 30 min. The reaction was terminated by adding saturated $NaHCO_3$ (10 mL) and the resulting mixture was diluted with water (100 mL) and extracted with dichloromethane (50×2). The combined organic layer was concentrated to leave a residue which was purified by pre-HPLC to give the title compound 33 as a white solid (60 mg, 20%): m.p. 181~187° C. LCMS: 478 [M+1]$^+$; $^1$H NMR (DMSO-$d_6$) δ 0.76 (s, 9H), 1.61 (s, 1H), 2.18 (s, 2H), 2.76 (t, 2H, J=6.3 Hz), 4.24 (t, 2H, J=6.3 Hz), 6.06 (s, 2H), 6.31 (s, 2H), 6.62 (s, 1H), 6.83 (d, 1H, J=5.7 Hz), 7.34 (s, 1H), 7.70 (d, 1H, J=5.7 Hz).

Example 30

Preparation of 2-(6-iodobenzo[d][1,3]dioxol-5-ylthio)-1-(2-(neopentylamino)ethyl)-1H-imidazo[4,5-c]pyridin-4-amine (Compound 34)

The title compound 34 was prepared as a white solid (2.718 g, 26%) from compound 32 (9.1 g, 19.9 mmol), pivalaldehyde (2.06 g, 24 mmol) and $NaBH_3CN$ (5.027 g, 80 mmol) using a procedure similar to that described for compound 33 (Example 29): m.p. 203~207° C. LCMS: 526 [M+1]$^+$; $^1$H NMR (DMSO-$d_6$) δ 0.77 (s, 9H), 1.60 (s, 1H), 2.18 (s, 2H), 2.75 (t, 2H, J=5.7 Hz), 4.23 (t, 2H, J=5.4 Hz), 6.04 (s, 2H), 6.33 (s, 2H), 6.58 (s, 1H), 6.83 (d, 1H, J=6.0 Hz), 7.46 (s, 1H), 7.77 (d, 1H, J=5.7 Hz).

Example 30

(Method 2): Preparation of 2-(6-iodobenzo[d][1,3]dioxol-5-ylthio)-1-(2-(neopentylamino)ethyl)-1H-imidazo[4,5-c]pyridin-4-amine (Compound 34)

Step 30a'. 2-(4-Amino-2-(6-iodobenzo[d][1,3]dioxol-5-ylthio)-1H-imidazo[4,5-c]pyridin-1-yl)ethyl acetate (Compound 0402-34)

A mixture of compound 0206-3 (300 mg, 0.728 mmol), 2-bromoethyl acetate (182 mg, 1.092 mmol) and $Cs_2CO_3$ (402 mg, 1.24 mmol) in DMF (10 mL) was stirred at 85° C. for 2 h. DMF was evaporated under vacuum and the residue was purified by column chromatography on silica gel (methylene chloride/methanol at 100:1) to yield the title compound 0402-34 as a white solid (188 mg, 50.4%): LCMS: 499 [M+1]$^+$; $^1$H NMR (DMSO-$d_6$) δ 1.86 (s, 3H), 4.26 (t, 2H, J=4.8 Hz), 4.45 (t, 2H, J=4.8 Hz), 6.03 (s, 2H), 6.35 (s, 2H), 6.68 (s, 1H), 6.81 (d, 1H, J=6.0 Hz), 7.76 (s, 1H), 7.71 (d, 1H, J=6.0 Hz).

Step 30b'. 2-(4-Amino-2-(6-iodobenzo[d][1,3]dioxol-5-ylthio)-1H-imidazo[4,5-c]pyridin-1-yl)ethanol (Compound 0403-34)

A suspension of compound 0402-34 (180 mg, 0.36 mmol) in MeOH (3 mL) was treated with $K_2CO_3$ (60 mg, 0.43 mmol) at 50° C. for 1 h. The mixture was diluted with water (15 mL) and filtered to provide the title compound 0403-34 as a white solid (150 mg, 91%): LCMS: 457 [M+1]$^+$; $^1$H NMR (DMSO-d$_6$) δ 3.63 (m, 2H), 4.27 (t, 2H, J=5.4 Hz), 4.98 (t, 2H, J=5.7 Hz), 6.05 (s, 2H), 6.31 (s, 2H), 6.69 (s, 1H), 6.80 (d, 1H, J=6.0 Hz), 7.46 (s, 1H), 7.69 (d, 1H, J=5.7 Hz).

Step 30c'. 2-(4-Amino-2-(6-iodobenzo[d][1,3]dioxol-5-ylthio)-1H-imidazo[4,5-c]pyridin-1-yl)ethyl methanesulfonate (Compound 0404-34)

Compound 0403-34 (133 mg, 0.292 mmol) was dissolved in hot anhydrous dioxane (4 mL). The solution was cooled to 40° C. and was then treated with NEt$_3$ (89 mg, 0.876 mmol) and MsCl (50 mg, 0.438 mmol) for 20 min. The mixture was concentrated and purified by column chromatography on silica gel (CH$_2$Cl$_2$/MeOH=50/1) to provide the title compound 0404-34 as a white solid (122 g, 78.3%): LCMS: 535 [M+1]$^+$; $^1$H NMR (DMSO-d$_6$) δ 3.07 (s, 3H), 4.46 (t, 2H, J=4.5 Hz), 4.59 (t, 2H, J=5.1 Hz), 6.05 (s, 2H), 6.59 (s, 2H), 6.71 (s, 1H), 6.90 (d, 1H, J=6.0 Hz), 7.48 (s, 1H), 7.73 (d, 1H, J=6.6 Hz).

Step 30d'. 2-(6-Iodobenzo[d][1,3]dioxol-5-ylthio)-1-(2-(neopentylamino)ethyl)-1H-imidazo[4,5-c]pyridin-4-amine (Compound 34)

A mixture of compound 0404-34 (170 mg, 0.318 mmol) 2,2-dimethylpropan-1-amine hydrochloride (786 mg, 6.36 mmol) and K$_2$CO$_3$ (1.318 g, 9.54 mmol) in toluene (10 mL) was heated at 60° C. for 1 h. the solvent was removed and the crude was purified by column chromatography on silica gel (CH$_2$Cl$_2$/MeOH=40/1) and followed pre-HPLC to provide the title compound 34 as a pale yellow solid (25 mg, 15%): m.p. 193~201° C. LCMS: 526 [M+1]$^+$; $^1$H NMR (DMSO-d$_6$) δ 0.77 (s, 9H), 1.60 (s, 1H), 2.18 (s, 2H), 2.75 (t, 2H, J=5.7 Hz), 4.23 (t, 2H, J=5.4 Hz), 6.04 (s, 2H), 6.33 (s, 2H), 6.58 (s, 1H), 6.83 (d, 1H, J=6.0 Hz), 7.46 (s, 1H), 7.77 (d, 1H, J=5.7 Hz).

Example 31

Preparation of 2-(7-iodo-2,3-dihydrobenzo[b][1,4]dioxin-6-ylthio)-1-(2-(neopentylamino)ethyl)-1H-imidazo[4,5-c]pyridin-4-amine (Compound 37)

Step 31a. 2-(7-Iodo-2,3-dihydrobenzo[b][1,4]dioxin-6-ylthio)-1-(4-methoxybenzyl)-1H-imidazo[4,5-c]pyridin-4-amine (Compound 0205-37)

The title compound 0205-37 was prepared as a brown solid (2.2 g, 38%) from compound 0204 (3 g, 10.5 mmol), 6,7-Diiodo-2,3-dihydrobenzo[b][1,4]dioxine (0107-7) (8.1 g, 21 mmol), neocuproine hydrate (0.2 g, 1.05 mmol), CuI (0.2 g, 1.05 mmol) and NaOt-Bu (1.5 g, 15.7 mmol) in anhydrous DMF (100 mL) using a procedure similar to that described for compound 0205-20 (Example 17): LCMS: 547[M+1]$^+$; $^1$H NMR (DMSO-d$_6$) δ 3.69 (s, 3H), 4.19 (m, 4H), 5.49 (s, 2H), 6.68 (s, 1H), 6.83 (d, 2H, J=8.4 Hz), 7.11 (d, 2H, J=8.7 Hz), 7.28 (d, 1H, J=7.2 Hz), 7.35 (s, 1H), 7.71 (d, 1H, J=7.2 Hz), 8.42 (s, 2H), 13.36 (s, 1H).

Step 31b. 2-(7-Iodo-2,3-dihydrobenzo[b][1,4]dioxin-6-ylthio)-1H-imidazo[4,5-c]pyridin-4-amine (Compound 0206-37)

The title compound 0206-37 was prepared as a yellow solid (1.5 g, 88%) from compound 0205-37 (2.2 g, 4 mmol) was dissolved in TFA (20 mL) using a procedure similar to that described for compound 0206-20 (Example 17): LCMS: 427 [M+1]$^+$; $^1$H NMR (DMSO-d$_6$) δ 4.29 (m, 4H), 6.96 (d, 1H, J=6.9 Hz), 7.20 (s, 1H), 7.50 (s, 1H), 7.63 (d, 1H, J=6.9 Hz), 8.42 (s, 2H), 13.36 (s, 1H).

Step 31c. 2-(2-(4-Amino-2-(7-iodo-2,3-dihydrobenzo[b][1,4]dioxin-6-ylthio)-1H-imidazo[4,5-c]pyridin-1-yl)ethyl)isoindoline-1,3-dione (Compound 0302-37)

The title compound 0302-37 was prepared as a white solid (1.2 g, 57%) from compound 0206-37 (1.5 g, 3.5 mmol), 2-(2-bromoethyl)isoindoline-1,3-dione (1.34 g, 5.3 mmol), Cs$_2$CO$_3$ (1.94 g, 6.0 mmol) and DMF (50 mL) using a procedure similar to that described for compound 0302-32 (Example 28): LCMS: 600 [M+1]$^+$; $^1$H NMR (DMSO-d$_6$) δ 3.92 (t, 2H, J=5.7 Hz), 4.16 (m, 4H), 4.48 (t, 2H, J=4.8 Hz), 6.38 (s, 2H), 6.41 (s, 1H), 6.75 (d, 1H, J=6 Hz), 7.15 (s, 1H), 7.64 (d, 1H, J=5.7 Hz), 7.77 (m, 4H).

Step 31d. 1-(2-Aminoethyl)-2-(7-iodo-2,3-dihydrobenzo[b][1,4]dioxin-6-ylthio)-1H-imidazo[4,5-c]pyridin-4-amine (Compound 0303-37)

The title compound 0303-37 was prepared as a pale yellow solid (790 mg, 84%) from compound 0302-37 (1.2 g, 2 mmol) and N$_2$H$_4$—H$_2$O (1 g, 20 mmol) in CH$_2$Cl$_2$ (28 mL) and EtOH (3 mL) using a procedure similar to that described for compound 0303-32 (Example 28): LC-MS: 470 [M+1]$^+$. $^1$H NMR (300 MHz, DMSO-d$_6$) δ 1.51 (m, 2H), 2.77 (t, 2H, J=6.6 Hz), 4.16 (m, 6H), 6.27 (s, 2H), 6.53 (s, 1H), 6.81 (d, 1H, J=6 Hz), 7.35 (s, 1H), 7.67 (d, 1H, J=5.7 Hz).

Step 31e. 2-(7-Iodo-2,3-dihydrobenzo[b][1,4]dioxin-6-ylthio)-1-(2-(neopentylamino)ethyl)-1H-imidazo[4,5-c]pyridin-4-amine (Compound 37)

The title compound 37 was prepared as a white solid (128 mg, 14%) from compound 0303-37 (790 mg, 1.7 mmol), pivalaldehyde (217 mg, 2.5 mmol) and NaBH$_3$CN (423 mg, 6.7 mmol) using a procedure similar to that described for compound 33 (Example 29): m.p. 193~200° C. LCMS: 540 [M+1]$^+$; $^1$H NMR (DMSO-d$_6$) δ 0.793 (s, 9H), 2.32 (s, 2H), 2.88 (t, 2H, J=6.3 Hz), 4.18 (m, 4H), 4.32 (t, 2H, J=6.6 Hz), 6.50 (s, 1H), 6.76 (s, 2H), 6.94 (d, 1H, J=6Hz), 7.37 (s, 1H), 7.73 (d, 1H, J=6.3 Hz).

Example 32

Preparation of 1-(2-(tert-butylamino)ethyl)-2-(6-iodobenzo[d][1,3]dioxol-5-ylthio)-1H-imidazo[4,5-c]pyridin-4-amine (Compound 40)

A solution of compound 0404-34 (250 mg, 0.47 mmol) in tert-butylamine (30 mL) was stirred at 60° C. for 24 h in a pressure vessel. The solvent was removed and the crude was purified by column chromatography on silica gel (CH$_2$Cl$_2$/MeOH=50/1) and followed by pre-HPLC to provide the title compound 40 as a white solid (34 mg, 15%): m.p. 194~197° C. LCMS: 512 [M+1]$^+$; $^1$H NMR (DMSO-d$_6$) δ 0.88 (s, 9H), 1.60 (s, 1H), 2.70 (t, J=6.0 Hz, 2H), 4.20 (t, J=6.0 Hz, 2H), 6.05 (s, 2H), 6.35 (s, 2H), 6.70 (s, 1H), 6.83 (d, J=6.0 Hz, 1H), 7.48 (s, 1H), 7.72 (d, J=6.0 Hz, 1H).

Example 33

Preparation of 2-(6-iodobenzo[d][1,3]dioxol-5-ylthio)-1-(2-(isopropylamino)ethyl)-1H-imidazo[4,5-c]pyridin-4-amine (Compound 42)

The title compound 42 was prepared as a white solid (40 mg, 17%) from compound 0404-34 (252 mg, 0.47 mmol) in isopropylamine (30 mL) using a procedure similar to that described for compound 40 (Example 32): m.p. 170~172° C. LCMS: 498 [M+1]$^+$; $^1$H NMR (DMSO-d$_6$) δ 0.86 (d, J=6.3 Hz, 6H), 1.68 (s, 1H), 2.62 (m, 1H), 2.74 (t, J=6.6 Hz, 2H), 4.21 (t, J=6.6 Hz, 2H), 6.04 (s, 2H), 6.36 (s, 2H), 6.67 (s, 1H), 6.82 (d, J=6.0 Hz, 1H), 7.47 (s, 1H), 7.71 (d, J=6.0 Hz, 1H).

Example 34

Preparation of 2-(6-iodobenzo[d][1,3]dioxol-5-ylthio)-1-(2-(pentan-3-ylamino)ethyl)-1H-imidazo[4,5-c]pyridin-4-amine (Compound 44)

To a solution of compound 32 (228 mg, 0.5 mmol) in methanol (9 mL) was added 3-pentanone (65 mg, 0.75 mmol). After the reaction was stirred for 30 min at room temperature, NaBH$_3$CN (125 mg, 2 mmol) was added slowly. Trace of CH$_3$COOH was added and the mixture was stirred for overnight. The reaction was terminated by adding saturated NaHCO$_3$ (20 mL). The mixture was diluted with water (100 mL) and extracted with dichloromethane (50 mL×3). The extract was concentrated and purified by pre-HPLC to give the title compound 44 as a white solid (139 mg, 53%): m.p. 142~147° C. LCMS: 526 [M+1]$^+$; $^1$H NMR (DMSO-d$_6$): δ 0.75 (t, J=6.6 Hz, 6H), 1.31 (m, 4H), 2.42 (m, 1H), 2.85 (t, J=7.2 Hz, 2H), 4.33 (t, J=7.2 Hz, 2H), 6.06 (s, 2H), 6.52 (s, 2H), 6.66 (s, 1H), 6.92 (d, J=6.3 Hz, 1H), 7.49 (s, 1H), 7.74 (d, J=6.0 Hz, 1 H).

Example 35

Preparation of 1-(2-(dimethylamino)ethyl)-2-(6-iodobenzo[d][1,3]dioxol-5-ylthio)-1H-imidazo[4,5-c]pyridin-4-amine (Compound 46)

To a solution of compound 32 (150 mg, 0.32 mmol) in methanol (6 mL) was added aqueous HCHO solution (52 mg, 0.64 mmol). After stirred for 30 min at room temperature, NaBH$_3$CN (81 mg, 1.28 mmol) was added slowly, and the mixture was stirred overnight. The reaction was terminated by adding saturated NaHCO$_3$ (10 ml). The mixture was diluted with water (100 ml) and extracted with dichloromethane (50 mL×2). The extract was concentrated and purified by pre-HPLC to give the title compound 46 (30 mg, 19%) as a white solid. m.p. 170~172° C.; LCMS: 484[M+1]$^+$; $^1$H NMR (DMSO-d$_6$): δ 2.14 (s, 6H), 2.48 (t, J=6.3 Hz, 2H), 4.27 (t, J=6.3 Hz, 2H), 6.05 (s, 2H), 6.38 (s, 2H), 6.67 (s, 1H), 6.81 (d, J=6.0 Hz, 1H), 7.48 (s, 1H), 7.72 (d, J=6.0 Hz, 1H).

Example 36

Preparation of 2-(6-iodobenzo[d][1,3]dioxol-5-ylthio)-1-(2-(methylamino)ethyl)-1H-imidazo[4,5-c]pyridin-4-amine (Compound 48)

The title compound 48 was prepared as a white solid (40 mg, 18%) from compound 0404-34 (250 mg, 0.47 mmol) in methylamine alcoholic solution (30 mL) using a procedure similar to that described for compound 40 (Example 32): m.p. 145~155° C. LCMS: 470 [M+1]$^+$; $^1$H NMR (DMSO-d$_6$) δ 1.85 (s, 1H), 2.23 (s, 6H), 2.73 (t, J=6.6 Hz, 2H), 4.24 (t, J=6.6 Hz, 2H), 6.05 (s, 2H), 6.34 (s, 2H), 6.68 (s, 1H), 6.82 (d, J=6.0 Hz, 1H), 7.47 (s, 1H), 7.71 (d, J=6.0 Hz, 1H).

Example 37

Preparation of 2-(2-iodo-5-methoxyphenylthio)-1-(2-(neopentylamino)ethyl)-1H-imidazo[4,5-c]pyridin-4-amine (Compound 50)

Step 37a. 2-(2-(4-Amino-2-(2-iodo-5-methoxyphenylthio)-1H-imidazo[4,5-c]pyridin-1-yl)ethyl)isoindoline-1,3-dione (Compound 0302-50)

The title compound 0302-50 was prepared as a white solid (315 mg, 44%) from compound 2-(2-Iodo-5-methoxyphenylthio)-1H-imidazo[4,5-c]pyridin-4-amine (Compound 0206-26) (500 mg, 1.256 mmol), 2-(2-bromoethyl)isoindoline-1,3-dione (478 mg, 1.884 mmol) and Cs$_2$CO$_3$ (694 mg, 2.135 mmol) in anhydrous DMF (18 mL) using a procedure similar to that described for compound 0302-32 (Example 28): LCMS: 572 [M+1]$^+$.

Step 37b. 1-(2-Aminoethyl)-2-(2-iodo-5-methoxyphenylthio)-1H-imidazo[4,5-c]pyridin-4-amine (Compound 0303-50)

The title compound 0303-50 was prepared as a white solid. (206 mg, 86%) from compound 0302-50 (310 mg, 0.543 mmol) and N$_2$H$_4$—H$_2$O (320 mg, 5.43 mmol) in CH$_2$Cl$_2$ (10 mL) and EtOH (2 mL) using a procedure similar to that described for compound 0303-32 (Example 28): LCMS: 442 [M+1]$^+$.

Step 37c. 2-(2-Iodo-5-methoxyphenylthio)-1-(2-(neopentylamino)ethyl)-1H-imidazo[4,5-c]pyridin-4-amine (Compound 50)

The title compound 50 was prepared as a white solid (45 mg, 28%) from compound 0303-50 (140 mg, 0.317 mmol), pivalaldehyde (33 mg, 0.381 mmol) and NaBH$_3$CN (80 mg, 1.268 mmol) using a procedure similar to that described for compound 33 (Example 29): m.p. 155~167° C. LCMS: 512 [M+1]$^+$; $^1$H NMR (DMSO-d$_6$) δ 0.76 (s, 9H), 2.15 (s, 2H), 2.74 (t, 2H, J=6.3 Hz), 3.58 (s, 3H), 4.22 (t, 2H, J=6.3 Hz), 6.30 (d, 1H, J=2.4 Hz), 6.43 (s, 2H), 6.67 (dd, 1H, J$_1$=3.0 Hz, J$_2$=9.0 Hz), 6.85 (d, 1H, J=6.07 Hz), 7.74 (m, 2H).

Example 38

Preparation of 2-(6-bromobenzo[d][1,3]dioxol-5-ylthio)-1-(3-(isopropylamino)propyl)-1H-imidazo[4,5-c]pyridin-4-amine (Compound 51)

Step 38a. 3-(4-Amino-2-(6-bromobenzo[d][1,3]dioxol-5-ylthio)-1H-imidazo[4,5-c]pyridin-1-yl)propyl acetate (Compound 0402-51)

A mixture of compound 0206-22 (500 mg, 1.37 mmol), 3-bromopropyl acetate (372 mg, 2.05 mmol) and Cs$_2$CO$_3$ (757 mg, 2.33 mmol) in DMF (17 mL) was stirred at 85° C. for 2 h. DMF was evaporated under vacuum and the residue was purified by column chromatography on silica gel (methylene chloride/methanol at 100:1) to yield the title compound 0402-51 as a white solid (340 mg, 53%): LCMS: 465 [M+1]$^+$; $^1$H NMR (DMSO-d$_6$) δ 1.92 (m, 5H), 3.94 (t, 2H, J=5.7 Hz), 4.27 (t, 2H, J=6.9 Hz), 6.07 (s, 2H), 6.39 (s, 2H), 6.64 (s, 1H), 6.80 (d, 1H, J=6.0 Hz), 7.36 (s, 1H), 7.72 (d, 1H, J=5.7 Hz).

Step 38b. 3-(4-Amino-2-(6-bromobenzo[d][1,3]dioxol-5-ylthio)-1H-imidazo[4,5-c]pyridin-1-yl)propan-1-ol (Compound 0403-51)

A suspension of compound 0402-51 (340 mg, 0.73 mmol) in MeOH (7 mL) was treated with $K_2CO_3$ (122 mg, 0.88 mmol) at 50° C. for 1 h. The mixture was diluted with water (25 mL) and filtered to provide the title compound 0403-51 as a white solid (264 mg, 85%): LCMS: 423 [M+1]$^+$; $^1$H NMR (DMSO-$d_6$) δ 1.78 (m, 2H), 3.39 (m, 2H), 4.24 (t, 2H, J=7.2 Hz), 4.65 (t, 2H, J=4.8 Hz), 6.08 (s, 2H), 6.35 (s, 2H), 6.67 (S, 1H), 6.80 (d, 1H, J=5.7 Hz), 7.36 (s, 1H), 7.71 (d, 1H, J=6.0 Hz).

Step 38c. 3-(4-Amino-2-(6-bromobenzo[d][1,3]dioxol-5-ylthio)-1H-imidazo[4,5-c]pyridin-1-yl)propyl methanesulfonate (0404-51)

Compound 0403-51 (264 mg, 0.624 mmol) was dissolved in hot anhydrous dioxane (8.6 mL). The solution was cooled to 40° C. and was treated with NEt$_3$ (189 mg, 1.87 mmol) and MsCl (107 mg, 0.935 mmol) for 20 min. The mixture was concentrated and purified by column chromatography on silica gel (CH$_2$Cl$_2$/MeOH=50/1) to give the title compound 0404-51 as a white solid (143 g, 50%): LCMS: 501 [M+1]$^+$.

Step 38d. 2-(6-Bromobenzo[d][1,3]dioxol-5-ylthio)-1-(3-(isopropylamino)propyl)-1H-imidazo[4,5-c]pyridin-4-amine (Compound 51)

A solution of compound 0404-51 (113 mg, 0.225 mmol) in isopropylamine (5 mL) was stirred at 60° C. for 1 h in a pressure vessel. The solvent was removed and the crude was purified by column chromatography on silica gel (CH$_2$Cl$_2$/MeOH=40/1) to provide the title compound 51 as a white solid (31 mg, 30%): m.p. 140~149° C. LCMS: 464 [M+1]$^+$; $^1$H NMR (DMSO-$d_6$) δ 1.05 (m, 6H), 1.91 (m, 2H), 2.67 (t, 2H, J=7.2 Hz), 2.89 (m, 1H), 4.27 (t, 2H, J=7.5 Hz), 6.08 (s, 2H), 6.38 (s, 2H), 6.68 (s, 1H), 6.88 (d, 1H, J=5.7 Hz), 7.37 (s, 1H), 7.73 (d, 1H, J=6.0 Hz).

Example 39

Preparation of 2-(6-iodobenzo[d][1,3]dioxol-5-ylthio)-1-(3-(isopropylamino)propyl)-1H-imidazo[4,5-c]pyridin-4-amine (Compound 52)

Step 39a. 3-(4-Amino-2-(6-iodobenzo[d][1,3]dioxol-5-ylthio)-1H-imidazo[4,5-c]pyridin-1-yl)propyl acetate (Compound 0402-52)

The title compound 0402-52 was prepared as a white solid (310 mg, 50%) from compound 2-(6-Iodobenzo[d][1,3]dioxol-5-ylthio)-1H-imidazo[4,5-c]pyridin-4-amine (Compound 0206-3) (500 mg, 1.213 mmol), 3-bromopropyl acetate (329 mg, 1.819 mmol) and Cs$_2$CO$_3$ (670 mg, 2.062 mmol) in DMF (17 mL) using a procedure similar to that described for compound 0402-51 (Example 38).

Step 39b. 3-(4-Amino-2-(6-iodobenzo[d][1,3]dioxol-5-ylthio)-1H-imidazo[4,5-c]pyridin-1-yl)propan-1-ol (Compound 0403-52)

The title compound 0403-52 was prepared as a white solid (250 mg, 88%) from compound 0402-52 (310 mg, 0.605 mmol) and K$_2$CO$_3$ (100 mg, 0.727 mmol) in MeOH (5 mL) using a procedure similar to that described for compound 0403-51 (Example 38): LCMS: 471 [M+1]$^+$; $^1$H NMR (DMSO-$d_6$) δ 1.78 (m, 2H), 3.39 (m, 2H), 4.22 (t, 2H, J=6.9 Hz), 4.64 (t, 2H, J=4.8 Hz), 6.05 (s, 2H), 6.33 (s, 2H), 6.66 (s, 1H), 6.79 (d, 1H, J=6.0 Hz), 7.48 (s, 1H), 7.71 (d, 1H, J=5.7 Hz).

Step 39c. 3-(4-Amino-2-(6-iodobenzo[d][1,3]dioxol-5-ylthio)-1H-imidazo[4,5-c]pyridin-1-yl)propyl methanesulfonate (Compound 0404-52)

The title compound 0404-52 was prepared as a white solid (181 g, 62%) from compound 0403-52 (250 mg, 0.532 mmol), NEt$_3$ (161 mg, 1.596 mmol) and MsCl (91 mg, 0.798 mmol) using a procedure similar to that described for compound 0404-51 (Example 38): LCMS: 549 [M+1]$^+$; $^1$H NMR (DMSO-$d_6$) δ 2.08 (m, 2H), 3.16 (s, 3H 4.25 (m, 4H), 6.05 (s, 2H), 6.39 (s, 2H), 6.67 (s, 1H), 6.82 (d, 1H, J=5.7 Hz), 7.48 (s, 1H), 7.73 (d, 1H, J=5.7 Hz).

Step 39d. 2-(6-Iodobenzo[d][1,3]dioxol-5-ylthio)-1-(3-(isopropylamino)propyl)-1H-imidazo[4,5-c]pyridin-4-amine (Compound 52)

The title compound 52 was prepared as a white solid (54 mg, 32%) from compound 0404-52 (180 mg, 0.328 mmol) in isopropylamine (5 mL) using a procedure similar to that described for compound 51 (Example 38): m.p. 185~193° C. LCMS: 512 [M+1]$^+$; $^1$H NMR (DMSO-$d_6$) δ 0.97 (m, 6H), 1.81 (m, 2H), 2.55 (m, 2H), 2.73 (m, 1H), 4.24 (t, 2H, J=6.3 Hz), 6.05 (s, 2H), 6.38 (s, 2H), 6.65 (s, 1H), 6.84 (d, 1H, J=5.4 Hz), 7.48 (s, 1H), 7.72 (d, 1H, J=5.7 Hz).

Example 40

Preparation of 2-(2-bromo-5-methoxyphenylthio)-1-(3-(isopropylamino)propyl)-1H-imidazo[4,5-c]pyridin-4-amine (Compound 53)

Step 40a. 2-(2-Bromo-5-methoxyphenylthio)-1-(4-methoxybenzyl)-1H-imidazo[4,5-c]pyridin-4-amine (Compound 0205-53)

A mixture of compound 0204 (1.549 g, 5.41 mol), 1-bromo-2-iodo-4-methoxybenzene (Compound 0104-13) (2.54 g, 8.115 mol), neocuproine hydrate (113 mg, 0.541 mmol), CuI (103 mg, 0.541 mmol) and NaOt-Bu (519 mg, 5.41 mmol) in anhydrous DMF (50 mL) was stirred for 24 h at 110° C. (oil bath) under nitrogen atmosphere. The solvent was removed under high vacuum and the crude purified by column chromatography on silica gel (CH$_2$Cl$_2$/MeOH at 100/1) to give the title compound 0205-53 as a brown solid (1.67 g, 65%): LCMS: 471 [M+1]$^+$.

Step 40b. 2-(2-Bromo-5-methoxyphenylthio)-1H-imidazo[4,5-c]pyridin-4-amine (Compound 0206-53)

Compound 0205-53 (1.67 g, 3.55 mmol) was dissolved in TFA (12 mL) and stirred for 2 h at 80° C. The solvent was evaporated and the residue was adjusted to pH 7 with saturated NaHCO$_3$. The resulting precipitate was collected by filtration and further purified by column chromatography on silica gel (CH$_2$Cl$_2$/MeOH at 30/1) to give the title compound 0206-53 as a yellow solid (1.105 g, 88%): LCMS: 351 [M+1]$^+$; $^1$H NMR (DMSO-d$_6$) δ 3.65 (s, 3H), 6.78 (m, 3H), 7.08 (s, 2H), 7.55 (m, 2H).

Step 40c. 3-(4-Amino-2-(2-bromo-5-methoxyphenylthio)-1H-imidazo[4,5-c]pyridin-1-yl)propyl acetate (Compound 0402-53)

The title compound 0402-53 was prepared as a light yellow solid (750 mg, 53%) from compound 0206-53 (1.105 g, 3.15 mmol), 3-bromopropyl acetate (855 mg, 4.72 mmol) and Cs$_2$CO$_3$ (1.74 g, 5.35 mmol) in DMF (57 mL) using a procedure similar to that described for compound 0402-51 (Example 38): LCMS: 451 [M+1]$^+$.

Step 40d. 3-(4-Amino-2-(2-bromo-5-methoxyphenylthio)-1H-imidazo[4,5-c]pyridin-1-yl)propan-1-ol (Compound 0403-53)

The title compound 0403-53 was prepared as a white solid (560 mg, 82%) from compound 0402-53 (750 mg, 1.66 mmol) and K$_2$CO$_3$ (276 mg, 1.99 mmol) in MeOH (13 mL) using a procedure similar to that described for compound 0403-51 (Example 38): LCMS: 409 [M+1]$^+$; $^1$H NMR (DMSO-d$_6$) δ 1.78 (m, 2H), 3.37 (m, 2H), 3.61 (s, 3H), 4.25 (t, 2H, J=7.2 Hz), 4.63 (t, 1H, J=5.4 Hz), 6.32 (d, 1H, J=3.0 Hz), 6.44 (s, 2H), 6.83 (m, 2H), 7.60 (d, 1H, J=9.0 Hz), 7.74 (d, 1H, J=5.7 Hz).

Step 40e. 3-(4-Amino-2-(2-bromo-5-methoxyphenylthio)-1H-imidazo[4,5-c]pyridin-1-yl)propyl methanesulfonate (Compound 0404-53)

The title compound 0404-52 was prepared as a white solid (300 g, 47%) from compound 0403-53 (560 mg, 1.368 mmol), NEt$_3$ (415 mg, 4.105 mmol) and MsCl (235 mg, 2.052 mmol) using a procedure similar to that described for compound 0404-51 (Example 38): LCMS: 487 [M+1]$^+$.

Step 40f. 2-(2-Bromo-5-methoxyphenylthio)-1-(3-(isopropylamino)propyl)-1H-imidazo[4,5-c]pyridin-4-amine (53)

The title compound 53 was prepared as a white solid (54 mg, 32%) from compound 0404-53 (300 mg, 0.639 mmol) in isopropylamine (20 mL) using a procedure similar to that described for compound 51 (Example 38): m.p. 125~129° C. LCMS: 450 [M+1]$^+$; $^1$H NMR (DMSO-d$_6$) δ 0.89 (d, 6H, J=5.4 Hz), 1.51 (s, 1H), 1.74 (m, 2H), 2.38 (t, 2H, J=6.9 Hz), 2.55 (m, 1H), 3.60 (s, 3H), 4.24 (t, 2H, J=7.2 Hz), 6.33 (d, 1H, J=2.4 Hz), 6.46 (s, 2H), 6.84 (m, 2H), 7.60 (d, 1H, J=8.7 Hz), 7.72 (d, 1H, J=5.4 Hz).

Example 41

Preparation of 2-(2-iodo-5-methoxyphenylthio)-1-(3-(isopropylamino)propyl)-1H-imidazo[4,5-c]pyridin-4-amine (Compound 54)

Step 41a. 2-(2-Iodo-5-methoxyphenylthio)-1-(4-methoxybenzyl)-1H-imidazo[4,5-c]pyridin-4-amine (Compound 0205-54)

The title compound 0205-54 was prepared as a brown solid (734 mg, 55%) from compound 0204 (1 g, 3.5 mmol), 1,2-Diiodo-4-methoxybenzene (Compound 0104-12) (1.5 g, 4.2 mmol), neocuproine hydrate (73 mg, 0.35 mmol), CuI (66 mg, 0.35 mmol) and NaOt-Bu (335 mg, 3.5 mmol) in anhydrous DMF (33 mL) using a procedure similar to that described for compound 0205-53 (Example 40): LCMS: 519 [M+1]$^+$.

Step 41b. 2-(2-Iodo-5-methoxyphenylthio)-1H-imidazo[4,5-c]pyridin-4-amine (Compound 0206-54)

The title compound 0206-54 was prepared as a yellow solid (181 mg, 53%) from compound 0205-54 (443 mg, 0.85 mmol) and TFA (4 mL) using a procedure similar to that described for compound 0206-53 (Example 40): LCMS: 399 [M+1]$^+$; $^1$H NMR (DMSO-d$_6$) δ 3.61 (s, 3H), 6.72 (m, 5H), 7.51 (d, 1H, J=6.3 Hz), 7.74 (d, 1H, J=8.7 Hz).

Step 41c. 3-(4-Amino-2-(2-iodo-5-methoxyphenylthio)-1H-imidazo[4,5-c]pyridin-1-yl)propyl acetate (Compound 0402-54)

The title compound 0402-54 was prepared as a light yellow solid (531 mg, 53%) from compound 0206-54 (800 mg, 2.01 mmol), 3-bromopropyl acetate (546 mg, 3.02 mmol) and Cs$_2$CO$_3$ (1.11 g, 3.42 mmol) in DMF (36 mL) using a procedure similar to that described for compound 0402-51 (Example 38): LCMS: 499 [M+1]$^+$.

Step 41d. 3-(4-Amino-2-(2-iodo-5-methoxyphenylthio)-1H-imidazo[4,5-c]pyridin-1-yl)propan-1-ol (Compound 0403-54)

The title compound 0403-54 was prepared as a white solid (412 mg, 85%) from compound 0402-54 (531 mg, 1.066 mmol) and K$_2$CO$_3$ K$_2$CO$_3$ (177 mg, 1.279 mmol) in MeOH (8.3 mL) using a procedure similar to that described for compound 0403-51 (Example 38): LCMS: 457 [M+1]$^+$.

Step 41e. 3-(4-Amino-2-(2-iodo-5-methoxyphenylthio)-1H-imidazo[4,5-c]pyridin-1-yl)propyl methanesulfonate (Compound 0404-54)

The title compound 0404-53 was prepared as a white solid (260 mg, 54%) from compound 0403-54 (412 mg, 0.905 mmol), NEt$_3$ (275 mg, 2.716 mmol) and MsCl (156 mg, 1.358 mmol) using a procedure similar to that described for compound 0404-51 (Example 38): LCMS: 535 [M+1]$^+$.

Step 41f. 2-(2-Iodo-5-methoxyphenylthio)-1-(3-(isopropylamino)propyl)-1H-imidazo[4,5-c]pyridin-4-amine (Compound 54)

The title compound 54 was prepared as a white solid (18 mg, 16%) from compound 0404-54 (120 mg, 0.225 mmol) in isopropylamine (20 mL) using a procedure similar to that described for compound 51 (Example 38): LCMS: 498 [M+1]$^+$; $^1$H NMR (DMSO-d$_6$) δ 0.91 (d, 6H, J=6.3 Hz), 1.75 (m, 2H), 2.43 (t, 2H, J=5.7 Hz), 2.59 (m, 1H), 3.58 (s, 3H), 4.23 (t, 2H, J=7.2 Hz), 6.32 (d, 1H, J=2.7 Hz), 6.44 (s, 2H), 6.68 (dd, 1H, J$_1$=3.0 Hz, J$_2$=9.0 Hz), 6.85 (d, 1H, J=6.3 Hz), 7.75 (m, 2H).

Example 42

Preparation of 2-(6-iodobenzo[d][1,3]dioxol-5-ylthio)-1-(3-(neopentylamino)propyl)-1H-imidazo[4,5-c]pyridin-4-amine (Compound 56)

Step 42a. 2-(3-(4-Amino-2-(6-iodobenzo[d][1,3]dioxol-5-ylthio)-1H-imidazo[4,5-c]pyridin-1-yl)propyl)isoindoline-1,3-dione (Compound 0302-56)

The title compound 0302-56 was prepared as a pale yellow solid (410 mg, 57%) from compound 2-(6-Iodobenzo[d][1, 3]dioxol-5-ylthio)-1H-imidazo[4,5-c]pyridin-4-amine (Compound 0206-3) (500 mg, 1.2 mmol), 2-(3-bromopropyl) isoindoline-1,3-dione (610 mg, 2.4 mmol) and $Cs_2CO_3$ (652 mg, 2.0 mmol) in anhydrous DMF (8.5 mL) using a procedure similar to that described for compound 0302-32 (Example 28): LC-MS: 599.7 [M+1]$^+$; $^1$H NMR (DMSO-d$_6$): δ 1.93 (m, 2H), 3.61 (t, J=6.6 Hz, 2H), 4.21 (t, J=8.1 Hz, 2H), 6.04 (s, 2H), 6.40 (s, 2H), 6.50 (s, 1H), 6.87 (d, J=6.0 Hz, 1 H), 7.21 (s, 1H), 7.70 (d, J=6.0 Hz, 1H), 7.85 (s, 4H).

Step 42b. 1-(3-Aminopropyl)-2-(6-iodobenzo[d][1,3] dioxol-5-ylthio)-1H-imidazo[4,5-c]pyridin-4-amine (Compound 0303-56)

The title compound 0303-56 was prepared as a pale yellow solid (200 mg, 74%) from compound 0302-56 (350 mg, 0.58 mmol) and $N_2H_4$—$H_2O$ (580 mg, 11.6 mmol) in $CH_2Cl_2$ (7.0 mL) and EtOH (0.6 mL) using a procedure similar to that described for compound 0303-32 (Example 28): LC-MS: 469.7 [M+1]$^+$.

Step 42c. 2-(6-Iodobenzo[d][1,3]dioxol-5-ylthio)-1-(3-(neopentylamino)propyl)-1H-imidazo[4,5-c]pyridin-4-amine (Compound 56)

The title compound 56 was prepared as a white solid (110 mg, 37%) from compound 0303-56 (257 mg, 0.55 mmol) and pivalaldehyde (60 mg, 0.70 mmol). using a procedure similar to that described for compound 33 (Example 29): m.p. 170~174° C. LCMS: 540 [M+1]$^+$; $^1$H NMR (DMSO-d$_6$): δ 0.84 (s, 9H), 1.76 (m, 2H), 2.14 (s, 2H), 2.43 (t, J=6.9 Hz, 2H), 4.23 (t, J=7.2 Hz, 2H), 6.04 (s, 2H), 6.36 (s, 2H), 6.63 (s, 1H), 6.80 (d, J=6.0 Hz, 1H), 7.47 (s, 1H), 7.71 (d, J=6.0 Hz, 1H).

Example 43

Preparation of 1-(3-(tert-butylamino)propyl)-2-(6-iodobenzo[d][1,3]dioxol-5-ylthio)-1H-imidazo[4,5-c]pyridin-4-amine (Compound 58)

The title compound 58 was prepared as a white solid (64 mg, 37%) from compound 3-(4-amino-2-(6-iodobenzo[d][1, 3]dioxol-5-ylthio)-1H-imidazo[4,5-c]pyridin-1-yl)propyl methanesulfonate (0404-52) (180 mg, 0.328 mmol) in tert-butylamine (20 mL) using a procedure similar to that described for compound 51 (Example 38): m.p. 224~227° C. LCMS: 526 [M+1]$^+$; $^1$H NMR (DMSO-d$_6$): δ 0.95 (s, 9H), 1.71 (m, 2H), 2.38 (t, J=7.2 Hz, 2H), 4.23 (t, J=7.2 Hz, 2H), 6.04 (s, 2H), 6.37 (s, 2H), 6.64 (s, 1H), 6.82 (d, J=6.0 Hz, 1H), 7.48 (s, 1H), 7.72 (d, J=6.0 Hz, 1H).

Example 44

Preparation of 2-(6-iodobenzo[d][1,3]dioxol-5-ylthio)-1-(3-(pentan-3-ylamino)propyl)-1H-imidazo [4,5-c]pyridin-4-amine (Compound 60)

To a solution of 1-(3-Aminopropyl)-2-(6-iodobenzo[d][1, 3]dioxol-5-ylthio)-1H-imidazo[4,5-c]pyridin-4-amine (Compound 0303-56) (150 mg, 0.32 mmol) in methanol (6 mL) was added 3-pentanone (33 mg, 0.38 mmol). After stirred for 30 min at room temperature, $NaBH_3CN$ (80 mg, 1.28 mmol) was added slowly. Trace of $CH_3COOH$ was added and the mixture was stirred for overnight. The reaction was terminated by adding saturated $NaHCO_3$ (10 mL). The mixture was diluted with water (100 mL) and extracted with dichloromethane (50 mL×2). The extract was concentrated and purified by pre-HPLC to give the title compound 60 as a white solid (34 mg, 20%): m.p. 164~166° C. LCMS: 540 [M+1]$^+$; $^1$H NMR (DMSO-d$_6$): δ 0.80 (s, 9H), 1.29 (m, 4H), 2.21 (m, 1H), 2.43 (t, J=6.3 Hz, 2H), 4.24 (t, J=6.9 Hz, 2H), 6.05 (s, 2H), 6.40 (s, 2H), 6.64 (s, 1H), 6.83 (d, J=5.7 Hz, 1H), 7.49 (s, 1H), 7.72 (d, J=5.7 Hz, 1H).

Example 45

Preparation of 2-(6-bromobenzo[d][1,3]dioxol-5-ylthio)-1-(2-isopropoxyethyl)-1H-imidazo[4,5-c] pyridin-4-amine (Compound 61)

A solution of 2-(6-bromobenzo[d][1,3]dioxol-5-ylthio)-1H-imidazo[4,5-c]pyridin-4-amine (compound 0206-22) (500 mg, 1.37 mmol), $PPh_3$ (718 mg, 2.74 mmol), 2-isopropoxyethanol (185 mg, 1.78 mmol) and DIAD (830 mg, 4.11 mmol) in toluene (12 mL) and $CH_2Cl_2$ (3 mL) was stirred at room temperature for 20 min. The solvent was removed under vacuum and the crude purified by column chromatography on silica gel ($CH_2Cl_2$/MeOH at 30/1) and followed by pre-HPLC to give the title compound 61 as a white solid (113 mg, 18%): m. p. 183~190° C. LCMS: 451 [M+1]$^+$; $^1$H NMR (DMSO-d$_6$) δ 0.94 (d, 6H, J=5.4 Hz), 3.45 (m, 1H), 3.64 (t, 2H, J=7.52 Hz), 4.51 (t, 2H, J=3.9 Hz), 6.12 (s, 2H), 7.02 (s, 1H), 7.28 (d, 1H, J=7.5 Hz), 7.40 (s, 1H), 7.74 (d, 1H, J=6.6 Hz), 8.57 (s, 2H), 13.28 (s, 1H).

Example 46

Preparation of 2-(6-iodobenzo[d][1,3]dioxol-5-ylthio)-1-(2-isopropoxyethyl)-1H-imidazo[4,5-c] pyridin-4-amine (Compound 62)

The title compound 62 was prepared as a white solid (100 mg, 28%) from compound 2-(6-Iodobenzo[d][1,3]dioxol-5-ylthio)-1H-imidazo[4,5-c]pyridin-4-amine (Compound 0206-3) (300 mg, 0.727 mmol), $PPh_3$ (381 mg, 1.46 mmol), 2-isopropoxyethanol (98.5 mg, 0.946 mmol) and DIAD (441 mg, 2.18 mmol) in toluene (6 mL) and $CH_2Cl_2$ (1.5 mL) using a procedure similar to that described for compound 61 (Example 45): m. p. 195~201° C. LCMS: 499 [M+1]$^+$; $^1$H NMR (DMSO-d$_6$) δ 0.95 (d, 6H, J=6.6 Hz), 3.45 (m, 1H), 3.64 (t, 2H, J=5.1 Hz), 4.49 (t, 2H, J=5.1 Hz), 6.09 (s, 2H), 6.99 (s, 1H), 7.27 (d, 1H, J=6.9 Hz), 7.52 (s, 1H), 7.73 (d, 1H, J=7.5 Hz), 8.49 (s, 2H), 13.12 (s, 1H).

Example 47

Preparation of 2-(2-iodo-5-methoxyphenylthio)-1-(2-isopropoxyethyl)-1H-imidazo[4,5-c]pyridin-4-amine (Compound 64)

The title compound 64 was prepared as a white solid (20 mg, 8.2%) from compound 2-(2-iodo-5-methoxyphenylthio)-1H-imidazo[4,5-c]pyridin-4-amine (compound 0206-54) (200 mg, 0.50 mmol), $PPh_3$ (263 mg, 1.00 mmol), 2-isopropoxyethanol (68 mg, 0.65 mmol) and DIAD (304 mg, 1.51 mmol) in toluene (5 mL) and $CH_2Cl_2$ (1 mL) using a procedure similar to that described for compound 61 (Example 45): m. p. 102~108° C. LCMS: 485 [M+1]$^+$; $^1$H NMR (DMSO-d$_6$) δ 0.89 (d, 6H, J=6.9 Hz), 3.38 (m, 1H), 3.56 (t, 2H, J=5.4 Hz), 3.60 (s, 3H), 4.35 (t, 2H, J=4.5 Hz), 6.39 (m, 3H), 6.67 (dd, 1H, J$_1$=2.1 Hz, J$_2$=8.1 Hz), 6.83 (d, 1H, J=6.0 Hz), 7.74 (m, 2H).

Example 48

Preparation of 4-(4-amino-2-(6-iodobenzo[d][1,3]dioxol-5-ylthio)-1H-imidazo[4,5-c]pyridin-1-yl)butanamide (Compound 66)

Step 48a. Ethyl 4-(4-amino-2-(6-iodobenzo[d][1,3]dioxol-5-ylthio)-1H-imidazo[4,5-c]pyridin-1-yl)butanoate (Compound 0502-66)

A mixture of 2-(6-Iodobenzo[d][1,3]dioxol-5-ylthio)-1H-imidazo[4,5-c]pyridin-4-amine (Compound 0206-3) (200 mg, 0.485 mmol), ethyl 4-bromobutanoate (142 mg, 0.728 mmol), $Cs_2CO_3$ (268 mg, 0.825 mmol) in DMF (7 mL) was stirred at 85° C. for 2 h. DMF was evaporated under vacuum and the residue was purified by column chromatography on silica gel (methylene chloride/methanol at 100:1) to yield the title compound 0502-66 as a white solid (168 mg, 66%): LCMS: 527 $[M+1]^+$.

Step 48b. 4-(4-Amino-2-(6-iodobenzo[d][1,3]dioxol-5-ylthio)-1H-imidazo[4,5-c]pyridin-1-yl)butanamide (Compound 66)

Compound 0502-66 (180 mg, 0.342 mmol) was dissolved in 5 mL ammonia in methanol (40%, W/W) and the mixture was stirred at 50° C. in a sealed tube overnight. Solvent was evaporated under reduced pressure and the residue was purified by column chromatography on silica gel (methylene chloride/methanol at 40:1) to yield the title compound 66 as a white solid (68 mg, 40%): m.p. 227~232° C., LCMS: 498 $[M+1]^+$; $^1H$ NMR (DMSO-$d_6$) δ 1.84 (m, 2H), 2.06 (t, 2H, J=7.2 Hz), 4.17 (t, 2H, J=7.2 Hz), 6.05 (s, 2H), 6.39 (s, 2H), 6.68 (s, 1H), 6.81 (m, 2H), 7.28 (s, 1H), 7.47 (s, 1H), 7.71 (d, 1H, J=6.0 Hz).

Example 49

Preparation of 5-(4-amino-2-(6-iodobenzo[d][1,3]dioxol-5-ylthio)-1H-imidazo[4,5-c]pyridin-1-yl)pentanamide (Compound 68)

Step 49a. Methyl 5-(4-amino-2-(6-iodobenzo[d][1,3]dioxol-5-ylthio)-1H-imidazo[4,5-c]pyridin-1-yl)pentanoate (Compound 0502-68)

The title compound 0502-68 was prepared as a white solid (131 mg, 51%) from compound 2-(6-Iodobenzo[d][1,3]dioxol-5-ylthio)-1H-imidazo[4,5-c]pyridin-4-amine (Compound 0206-3) (200 mg, 0.485 mmol), methyl 5-bromopentanoate (142 mg, 0.728 mmol), $Cs_2CO_3$ (268 mg, 0.825 mmol) in DMF (8 mL) using a procedure similar to that described for compound 0502-66 (Example 48): LCMS: 527 $[M+1]^+$; $^1H$ NMR (DMSO-$d_6$) δ 1.47 (m, 2H), 1.63 (m, 2H), 2.28 (t, 2H, J=7.5 Hz), 3.54 (s, 3H), 4.17 (t, 2H, J=6.9 Hz), 6.05 (s, 2H), 6.38 (s, 2H), 6.66 (s, 1H), 6.80 (d, 1H, J=6.0 Hz), 7.48 (s, 1H), 7.71 (d, 1H, J=5.7 Hz).

Step 49b. 5-(4-Amino-2-(6-iodobenzo[d][1,3]dioxol-5-ylthio)-1H-imidazo[4,5-c]pyridin-1-yl)pentanamide (Compound 68)

The title compound 68 was prepared as a white solid (38 mg, 30%) from compound 0502-68 (131 mg, 0.249 mmol) and 10 mL ammonia in methanol (40%, W/W) using a procedure similar to that described for compound 0502-66 (Example 48): m.p. 203~210° C., LCMS: 512 $[M+1]^+$; $^1H$ NMR (DMSO-$d_6$) δ 1.44 (m, 2H), 1.62 (m, 2H), 2.02 (t, 2H, J=7.2 Hz), 4.16 (t, 2H, J=6.9 Hz), 6.06 (s, 2H), 6.52 (s, 2H), 6.70 (m, 2H), 6.84 (d, 1H, J=5.7 Hz), 7.23 (s, 1H), 7.49 (s, 1H), 7.71 (d, 1H, J=6.0 Hz).

Example 50

Preparation of 6-(4-amino-2-(6-iodobenzo[d][1,3]dioxol-5-ylthio)-1H-imidazo[4,5-c]pyridin-1-yl)hexanamide (Compound 70)

Step 50a. Ethyl 6-(4-amino-2-(6-iodobenzo[d][1,3]dioxol-5-ylthio)-1H-imidazo[4,5-c]pyridin-1-yl)hexanoate (Compound 0502-70)

The title compound 0502-70 was prepared as a white solid (200 mg, 30%) from compound 2-(6-Iodobenzo[d][1,3]dioxol-5-ylthio)-1H-imidazo[4,5-c]pyridin-4-amine (Compound 0206-3) (500 mg, 1.2 mmol), methyl ethyl 6-bromohexanoate (401 mg, 1.8 mmol), $Cs_2CO_3$ (670 mg, 2.1 mmol) in DMF (18 mL) using a procedure similar to that described for compound 0502-66 (Example 48): LCMS: 555 $[M+1]^+$.

Step 50b. 6-(4-Amino-2-(6-iodobenzo[d][1,3]dioxol-5-ylthio)-1H-imidazo[4,5-c]pyridin-1-yl)hexanamide (Compound 70)

The title compound 70 was prepared as a white solid (35 mg, 18%) from compound 0502-70 (200 mg, 0.36 mmol) and 28 mL ammonia in methanol (40%, W/W) using a procedure similar to that described for compound 0502-66 (Example 48): m.p. 194~198° C., LCMS: 526 $[M+1]^+$; $^1H$ NMR (DMSO-$d_6$) δ 1.20 (m, 2H) 1.41 (m, 2H), 1.57 (m, 2H), 1.96 (t, 2H, J=7.8 Hz), 4.14 (t, 2H, J=7.4 Hz), 6.05 (s, 2H), 6.38 (s, 2H), 6.68 (2, 2H), 6.81 (d, 1H, J=5.7 Hz), 7.19 (s, 1H), 7.48 (s, 1H), 7.71 (d, 1H, J=6.0 Hz).

Example 51

Preparation of N-(2-(4-amino-2-(6-iodobenzo[d][1,3]dioxol-5-ylthio)-1H-imidazo[4,5-c]pyridin-1-yl)ethyl)acetamide (Compound 72)

Compound 32 (200 mg, 0.44 mmol) and $NEt_3$ (0.1 ml, 0.66 mmol) was dissolved in dichloromethane (10 ml) and cooled to 0° C. with ice-water bath. To this cold solution was added acetyl chloride (38 mg, 0.48 mmol) dropwise. The solution was stirred at 0° C. for 0.5 h and then the solvent was removed under reduced pressure. The residue was purified by pre-HPLC to give the title compound 72 as a white solid (47 mg, 22%): m.p. 193~197° C., LC-MS: 498 $[M+1]^+$. $^1H$ NMR (300 MHz, DMSO-$d_6$) δ 1.67 (s, 3H), 3.32 (m, 2H), 4.21 (t, 2H, J=5.6 Hz), 6.02 (s, 2H), 6.29 (s, 2H), 6.70 (s, 1H), 6.71 (d, 1H, J=5.7 Hz), 7.43 (s, 1H), 7.68 (d, 1H, J=5.7 Hz), 7.97 (t, 1H, J=6.0 Hz).

Example 52

Preparation of N-(3-(4-amino-2-(6-iodobenzo[d][1,3]dioxol-5-ylthio)-1H-imidazo[4,5-c]pyridin-1-yl)propyl)acetamide (Compound 74)

A suspension of 1-(3-aminopropyl)-2-(6-iodobenzo[d][1,3]dioxol-5-ylthio)-1H-imidazo[4,5-c]pyridin-4-amine (Compound 0303-56) (190 mg, 0.41 mmol) in acetic acid (1.4 mL) was cooled to 0° C. To this cold solution was added acetic anhydride (125 mg, 1.23 mmol). The reaction mixture was allowed to warm to room temperature and stirred at room temperature overnight. The reaction mixture was diluted with CH$_2$Cl$_2$ (8 mL) and the solvent was removed under reduced pressure to leave a residue which was purified by pre-HPLC to give the title product 74 as a white solid (90 mg, 43%): m.p. 102~104° C., LC-MS: 512.0 (M+H$^+$). $^1$H NMR (300 MHz, DMSO-d$_6$) δ 1.77 (m, 5H), 3.01 (m, 2H), 4.16 (t, 2H, J=7.5 Hz), 6.05 (s, 2H), 6.36 (s, 2H), 6.62 (s, 1H), 6.80 (d, 1H, J=5.7 Hz), 7.47 (s, 1H), 7.71 (d, 1H, J=6.0 Hz), 7.90 (t, 1H, J=4.5 Hz).

Example 53

Preparation of N-(4-(4-amino-2-(6-iodobenzo[d][1,3]dioxol-5-ylthio)-1H-imidazo[4,5-c]pyridin-1-yl)butyl)acetamide (Compound 76)

Step 53a. 2-(4-(4-Amino-2-(6-iodobenzo[d][1,3]dioxol-5-ylthio)-1H-imidazo[4,5-c]pyridin-1-yl)butyl)isoindoline-1,3-dione (Compound 0302-76)

A mixture of 2-(6-Iodobenzo[d][1,3]dioxol-5-ylthio)-1H-imidazo[4,5-c]pyridin-4-amine (Compound 0206-3) (412 mg, 1.0 mmol), 2-(4-bromobutyl)isoindoline-1,3-dione (620 mg, 2.2 mmol), Cs$_2$CO$_3$ (814 mg, 2.5 mmol) in anhydrous DMF (6 mL) was heated to 85° C. and stirred for 2 h. The reaction mixture was cooled to room temperature and filtered. The solvent DMF was removed under high vacuum to give a crude product as an orange solid which was purified by column chromatography on silica gel (CH$_2$Cl$_2$/MeOH/NEt$_3$=100/1/0.05) to give the title compound 0302-76 as a pale yellow solid (482 mg, 79%): LC-MS: 614 [M+1]$^+$.

Step 53b. 1-(4-Aminobutyl)-2-(6-iodobenzo[d][1,3]dioxol-5-ylthio)-1H-imidazo[4,5-c]pyridin-4-amine (Compound 0303-76)

A mixture of compound 0302-76 (470 mg, 0.77 mmol) and N$_2$H$_4$—H$_2$O (767 mg, 15.34 mmol) in CH$_2$Cl$_2$ (10.0 mL) and ethanol (1.0 mL) was heated to 50° C. and stirred for 1.5 h. The solvent was removed under reduced pressure and H$_2$O (25 mL) was added. The mixture was extracted with CH$_2$Cl$_2$ (30 mL×3). The combined organic layer was washed with H$_2$O (12 mL×2), dried over Na$_2$SO$_4$, filtered and evaporated to give the title compound 0303-76 as a pale yellow solid (240 mg, 65%): LC-MS: 483.7 (M+H$^+$).

Step 53c. N-(4-(4-Amino-2-(6-iodobenzo[d][1,3]dioxol-5-ylthio)-1H-imidazo[4,5-c]pyridin-1-yl)butyl)acetamide (Compound 76)

A suspension of 0303-76 (240 mg, 0.5 mmol) in acetic acid (1.6 mL) was cooled to 0° C. To this cold solution was added acetic anhydride (204 mg, 2.0 mmol). The reaction mixture was allowed to warm to room temperature and stirred overnight. The reaction mixture was diluted with CH$_2$Cl$_2$ (10 mL) and the solvent was removed under reduced pressure. The resulting residue was purified by pre-HPLC to give the title compound 76 as a white solid (70 mg, 27%): m.p. 198~201° C., LC-MS: 526.0 (M+H$^+$). $^1$H NMR (300 MHz, DMSO-d$_6$) δ 1.33 (m, 2H), 1.69 (m, 2H), 2.97 (m, 2H), 4.16 (t, 2H, J=7.2 Hz), 6.05 (s, 2H), 6.36 (s, 2H), 6.66 (s, 1H), 6.80 (d, 1H, J=5.7 Hz), 7.48 (s, 1H), 7.70 (d, 1H, J=5.7 Hz), 7.78 (t, 1H, J=4.5 Hz).

Example 54

Preparation of 2-(6-chlorobenzo[d][1,3]dioxol-5-ylthio)-1-(2-(neopentylamino)ethyl)-1H-imidazo[4,5-c]pyridin-4-amine (Compound 77)

Step 54a. 2-(2-(4-Amino-2-(6-chlorobenzo[d][1,3]dioxol-5-ylthio)-1H-imidazo[4,5-c]pyridin-1-yl)ethyl)isoindoline-1,3-dione (Compound 0302-77)

A mixture of 0206 (2.5 g, 7.8 mmol), 2-(2-bromoethyl)isoindoline-1,3-dione (0301) (3.0 mg, 11.7 mmol) and Cs$_2$CO$_3$ (4.3 g, 2.1 mmol) in anhydrous DMF (28 mL) was stirred at 85° C. for 4 h. The reaction mixture was cooled to room temperature and filtered. The filtrate was concentrated under high vacuum to give a crude product as an orange solid which was purified by column chromatography on silica gel (CH$_2$Cl$_2$/MeOH=100/1) to provide compound 0302-77 (1.5 g, 39%) as a pale yellow solid: LC-MS: 494 [M+1]$^+$; $^1$H NMR (400 MHz, DMSO-d$_6$) δ 3.93 (t, 2H, J=5.2 Hz), 4.52 (t, 2H, J=5.2 Hz), 6.05 (s, 2H), 6.60 (m, 3H), 6.83 (d, 1H, J=6.0 Hz), 6.99 (s, 1H), 7.66 (d, 1H, J=6.0 Hz), 7.76 (m, 4H).

Step 54b. 1-(2-Aminoethyl)-2-(6-chlorobenzo[d][1,3]dioxol-5-ylthio)-1H-imidazo[4,5-c]pyridin-4-amine (0303-77)

A mixture of 0302-77 (1.5 g, 3 mmol) and N$_2$H$_4$—H$_2$O (1.8 g, 85%, 85.5 mmol) in CH$_2$Cl$_2$ (50 mL) and EtOH (5 mL) was heated to 50° C. and stirred for 3 h. The solid was removed by filtration and the filtrate was washed with brine (100 mL×2). The organic layer was dried over Na$_2$SO$_4$, filtered and concentrated to give the title product 0303-77 (850 mg, 77%) as an orange solid: LC-MS: 364 [M+1]$^+$; $^1$H NMR (400 MHz, DMSO-d$_6$) δ 1.98 (s, 2H) 2.80 (m, 2H), 4.18 (t, 2H, J=6.4 Hz), 6.09 (s, 2H), 6.31 (s, 2H), 6.76 (s, 1H), 6.84 (d, 1H, J=5.6 Hz), 7.24 (s, 1H), 7.69 (d, 1H, J=5.6 Hz).

Step 54c. 2-(6-Chlorobenzo[d][1,3]dioxol-5-ylthio)-1-(2-(neopentylamino)ethyl)-1H-imidazo[4,5-c]pyridin-4-amine (Compound 77)

To a solution of 0303-77 (850 mg, 2.34 mmol) in methanol (33 mL) was added pivalaldehyde (242 mg, 2.8 mmol). After stirred for 30 min at room temperature, NaBH$_3$CN (588 g, 9.36 mmol) was added slowly, and the mixture was stirred for another 30 min. The mixture was diluted with water (500 mL) and extracted with dichloromethane (100 mL×2). The extract was concentrated and purified by column chromatography on silica gel (CH$_2$Cl$_2$/MeOH=50/1) and crystallization (CH$_2$Cl$_2$/Et$_2$O=1/4) to give the title compound 77 (195 mg, 19%) as a light yellow solid: m.p. 160~161° C. LCMS: 434 [M+1]$^+$; $^1$H NMR (DMSO-d$^6$) δ 0.76 (s, 9H), 1.60 (s, 1H), 2.17 (s, 2H), 2.76 (m, 2H), 4.24 (t, 2H, J=6.0 Hz), 6.07 (s, 2H), 6.32 (s, 2H), 6.68 (s, 1H), 6.83 (d, 1H, J=6.0 Hz), 7.24 (s, 1H), 7.70 (d, 1H, J=5.6 Hz).

Example 55

Preparation of 2-(6-methylbenzo[d][1,3]dioxol-5-ylthio)-1-(2-(neopentylamino)ethyl)-1H-imidazo[4,5-c]pyridin-4-amine (Compound 78)

Step 55a. 5-Iodo-6-methylbenzo[d][1,3]dioxole (Compound 0107-78)

NIS (6.6 g, 29.4 mmol) was added into a solution of compound 3,4-(methylenedioxy)toluene (5 g, 36.7 mmol) in MeCN (250 ml). To this mixture was added TFA (8.35 g, 73.4 mmol). The mixture was stirred overnight at room temperature. The solution was concentrated to leave a residue which was purified by column chromatography on silica to provide compound 0107-78 (12.3 g, 63%) as a red liquid. 1H NMR (DMSO-d$^6$): δ 2.26 (s, 3H), 5.99 (s, 2H), 6.94 (s, 1H), 7.30 (s, 1H).

Step 55b. 1-(4-Methoxybenzyl)-2-(6-methylbenzo[d] [1,3]dioxol-5-ylthio)-1H-imidazo[4,5-c]pyridin-4-amine (Compound 0205-78)

A mixture of compound 0204 (2.86 g, 10 mmol), compound 0107-78 (3.14 g, 12 mmol), NaOt-Bu (960 mg, 10 mmol), neocuproine hydrate (208 mg, 1 mmol) and CuI (190 mg, 1 mmol) in dry DMF (60 ml) was stirred at 110° C. overnight. The mixture was concentrated and purified by column chromatography on silica gel (CH$_2$Cl$_2$/MeOH=100/1) to provide compound 0205-78 (2.0 g, 48%) as an orange solid. LCMS: 421 [M+1]$^+$; 1H NMR (DMSO-d$^6$): δ 2.26 (s, 3H), 3.69 (s, 3H), 5.38 (s, 2H), 5.98 (s, 2H), 6.80 (m, 7H), 7.05 (d, J=8 Hz, 2H), 7.66 (s, 1H).

Step 55c. 2-(6-Methylbenzo[d][1,3]dioxol-5-ylthio)-1H-imidazo[4,5-c]pyridin-4-amine (Compound 0206-78)

A mixture of compound 0205-78 (2.0 g, 4.76 mmol) and CF$_3$COOH (20 ml) was stirred at 85° C. for 4 h. The mixture was concentrated and diluted with water (50 ml). The resulting solid was collected to provide the title compound 0206-78 (1.4 g, 78%) as a brown solid: LCMS: 301 [M+1]$^+$; 1H NMR (DMSO-d$^6$): δ 2.28 (s, 3H), 6.06 (s, 2H), 6.87 (s, 2H), 7.02 (s, 1H), 7.15 (s, 1H), 7.58 (s, 1H), 7.93 (s, 1H), 12.98 (s, 1H).

Step 55d. 2-(2-(4-Amino-2-(6-methylbenzo[d][1,3] dioxol-5-ylthio)-1H-imidazo[4,5-c]pyridin-1-yl) ethyl)isoindoline-1,3-dione (Compound 0302-78)

A mixture of compound 0206-78 (1.4 g, 4.67 mmol), 2-(2-bromoethyl)isoindoline-1,3-dione (1.78 g, 7.00 mmol), and Cs$_2$CO$_3$ (2.58 g, 7.93 mmol) in DMF (40 ml) was stirred for 4 h at 80° C. The reaction was filtered and the filtrate was concentrated. The product was purified by column chromatography (dichloromethane/methanol=20/1) to provide the title compound 0302-78 (760 mg, 34%) as a brown solid: LCMS: 474 [M+1]$^+$; 1H NMR (DMSO-d$^6$): δ 2.12 (s, 3H), 3.90 (t, J=5.4 Hz, 2H), 4.44 (t, J=5.4 Hz, 2H), 5.96 (s, 2H), 6.59 (s, 2H), 6.78 (t, 3H), 7.61 (d, J=5.6 Hz, 1H), 7.78 (m, 4H).

Step 55e. 1-(2-Aminoethyl)-2-(6-methylbenzo[d][1, 3]dioxol-5-ylthio)-1H-imidazo[4,5-c]pyridin-4-amine (Compound 0303-78)

To a mixture of H$_2$NNH$_2$ H$_2$O (800 mg, 16.1 mmol) in dichloromethane/methanol (30 ml, 10:1) was added compound 0302-78 (760 mg, 1.61 mmol). The mixture was stirred for 4 h at room temperature and then filtered. The filtrate was washed with brine and the organic phase was concentrated to provide the title compound 0303-78 (500 mg, 90%) as an orange solid: LCMS: 344 [M+1]$^+$; 1H NMR (DMSO-d$^6$): δ 1.93 (br, 2H), 2.32 (s, 3H), 2.75 (t, J=6.4 Hz, 2H), 4.11 (t, J=6.8 Hz, 2H), 5.99 (s, 2H), 6.16 (s, 2H), 6.79 (m, 2H), 6.93 (s, 1H), 7.64 (d, J=5.6 Hz, 1H).

Step 55f. 2-(6-Methylbenzo[d][1,3]dioxol-5-ylthio)-1-(2-(neopentylamino)ethyl)-1H-imidazo[4,5-c]pyridin-4-amine (Compound 78)

NaBH$_3$CN (366 mg, 5.82 mmol) was added to a solution of compound 0303-78 (500 mg, 1.46 mmol) and pivalaldehyde (151 mg, 1.75 mmol) in methanol (20 ml). The mixture was stirred for 0.5 h at room temperature. Dichloromethane (40 ml) was added into the above mixture and washed with brine for 3 times. The organic phase was dried over MgSO$_4$ and concentrated to give crude product which was purified by column chromatography (dichloromethane/methanol=20/1) and followed by recrystallization with dichloromethane and ether to provide the title compound 78 (30 mg, 5%) as a white solid: mp 155-156° C.; LCMS: 344 [M+1]$^+$; 1H NMR (DMSO-d$^6$) δ 0.76 (s, 9H), 2.17 (s, 2H), 2.33 (s, 3H), 2.70 (t, J=6.2 Hz, 2H), 4.18 (t, J=6.2 Hz, 2H), 5.98 (s, 2H), 6.20 (s, 2H), 6.78 (t, 2H), 6.93 (s, 1H), 7.65 (d, J=5.6 Hz, 1H).

Example 56

Preparation of 2-(6-(methylthio)benzo[d][1,3]dioxol-5-ylthio)-1-(2-(neopentylamino)ethyl)-1H-imidazo [4,5-c]pyridin-4-amine (Compound 87)

Step 56a. 5-(Methylthio)benzo[d][1,3]dioxole (Compound 0106-87)

To a suspension of magnesium turnings (2.25 g, 93.7 mmol) in anhydrous THF (50 mL) was added dropwise 5-bromo-1,3-benzodioxol (15.03 g, 75.1 mmol) over 1.5 h under an atmosphere of nitrogen. After being heated under reflux for 1 h. the mixture was cooled to −45° C. and powered sulfur (2.43 g, 75 mmol) was added to it. The mixture was stirred at −45° C. for 1.5 h and then at room temperature for 1.5 h, at which time water (4.1 mL) and 6M HCl (22.5 mL) were added to it. Then without purification adjust the reaction PH to 7.5, and then CH$_3$I (10.8 mL) was added followed by TEBA. The mixture was extracted with CH$_2$Cl$_2$, and the crude product was purified by column chromatography on silica gel (PE=100%) to provide the title product 0106-87 (7.034 g, 55.8%) as a white soil: $^1$H NMR (400 MHz, DMSO-d$_6$) δ 2.41 (s, 3H), 5.99 (s, 2H), 6.75 (q, 1H, J=2 Hz, 8 Hz), 6.86 (d, 1H, J=8 Hz), 6.92 (d, 1H, J=1.6 Hz).

Step 56b. 5-iodo-6-(methylthio)benzo[d][1,3]dioxole (Compound 0107-87)

A mixture of 0106-87 (9.034 g, 53.8 mmol), HNO$_3$ (5.4 ml), (CH$_3$CO)$_2$O (108 ml) was stirred at −10° C. for 2 h. The reaction was then poured onto the ice water for 0.5 h. The resulting yellow solid was collected to provide 5-(methothio)-6-nitrobenzo[d][1,3]dioxole (6.2 g, 54.3%): LCMS: 214 [M+1]$^+$; $^1$H NMR (400 MHz, DMSO-d$_6$) δ 2.49 (s, 3H), 6.25 (s, 2H), 7.12 (s, 1H), 7.79 (s, 1H).

A mixture of 5-(methothio)-6-nitrobenzo[d][1,3]dioxole (6.2 g, 29.2 mmol), Fe (16.36 g, 29.2 mmol), HCl (11.68 ml) in EtOH (73 ml) and H$_2$O (180 ml) was stirred at 110° C. for 2h. The reaction mixture was adjusted the PH to 11 and filtered. The filtrate was concentrated and purified by column chromatography on silica gel (petroleum ether/ethyl acetate=10/1) to get 6-(methylthio)benzo[d][1,3]dioxol-5-amine as a dark liquid (3.6 g, 67.3%): LCMS: 184 [M+1]$^+$; $^1$H NMR (400 MHz, DMSO-d$_6$) δ 2.3 (s, 3H), 5.05 (s, 2H), 5.86 (s, 2H) 6.39 (s, 1H), 6.83 (s, 1H).

The above prepared 6-(methylthio)benzo[d][1,3]dioxol-5-amine (3.6 g) was added into the mixture of H$_2$SO$_4$ (8.07 ml), CH₃CN (150 ml) and AcOH (225 ml) in water (150 ml) at 0° C. The mixture was stirred until becoming a clear solution. To this solution was added NaNO₂ (1.495 g) at 0° C. The mixture was warmed to room temperature and allowed to stir at rt for 30 min. The solution was slowly dropped into a solution of KI (9.811 g) in water (150 ml) at 50° C., cooled to room temperature to get a black solid which was purified by column chromatography on silica gel (petroleum ether) to obtain the title compound 0107-87 (3.4 g, 58.8%). $^1$H NMR (400 MHz, DMSO-d₆) δ 2.3 (s, 3H), 6.05 (s, 2H), 6.94 (s, 1H), 7.38 (s, 1H).

Step 56c. 1-(4-Methoxybenzyl)-2-(6-(methylthio)benzo[d][1,3]dioxol-5-ylthio)-1H-imidazo[4,5-c]pyridin-4-amine (Compound 0205-87)

The title compound 0205-87 was prepared (1.1 g, 65.3%) as a brown solid from compound 0204 (943 mg, 3.4 mmol), 0107-87 (2 g, 6.8 mmol), neocuproine hydrate (71 mg, 3.4 mmol), CuI (64.7 mg, 3.4 mmol) and NaOt-Bu (490 mg, 5.1 mmol) in anhydrous DMF (50 mL) using a procedure similar to that described for compound 0205-78 (Example 55): LCMS: 453 [M+1]⁺; $^1$H NMR (DMSO-d⁶) δ 3.68 (s, 3H), 5.37 (s, 2H), 6.00 (s, 2H), 6.45 (s, 2H), 6.64 (s, 1H), 6.81 (d, 2H, J=9.2 Hz), 6.94 (s, 1H), 7.04 (d, 2H, J=9.2 Hz), 7.65 (s, 1H).

Step 56d. 2-(6-(Methylthio)benzo[d][1,3]dioxol-5-ylthio)-1H-imidazo[4,5-c]pyridin-4-amine (Compound 0206-87)

The title compound 0206-87 was prepared (879 mg, 100%) as a yellow solid from compound 0205-87 (1.1 g, 2.45 mmol) and TFA (15 mL) using a procedure similar to that described for compound 0206-78 (Example 55): LCMS: 333 [M+1]⁺; $^1$H NMR (DMSO-d⁶) δ 2.40 (s, 3H), 6.09 (s, 2H), 6.74 (d, 1H, J=6.8 Hz,), 7.03 (s, 1H), 7.11 (s, 3H), 7.53 (d, 1H, J=5.6 Hz).

Step 56e. tert-Butyl 2-(4-amino-2-(6-(methylthio)benzo[d][1,3]dioxol-5-ylthio)-1H-imidazo[4,5-c]pyridin-1-yl)ethylcarbamate (Compound 0305-87)

A mixture of 0206-87 (879 mg, 2.65 mmol), tert-butyl 2-bromoethylcarbamate (891 mg, 3.975 mmol) and Cs₂CO₃ (1.464 g, 4.5 mmol) in anhydrous DMF (25 ml) was heated to 80° C. and stirred for 2 h. The reaction mixture was cooled to room temperature and filtered. The filtrate was concentrated to remove DMF under high vacuum to give a crude product as an orange solid which was purified by column chromatography on silica gel (CH₂Cl₂/MeOH=50/1) to provide the title compound 0305-87 (372 mg, 29.5%) as a yellow solid: LCMS: 476 [M+1]⁺; $^1$H NMR (400 MHz, DMSO-d₆) δ 1.26 (s, 9H), δ 2.43 (s, 3H), 3.22 (t, 2H, J=6.6 Hz) 4.18 (t, 2H, J=6.6 Hz), 6.03 (s, 2H), 6.83 (t, 2H, J=5 Hz), 6.96 (s, 1H), 7.08 (s, 1H), 7.67 (d, 1H, J=5 Hz).

Step 56f. 1-(2-Aminoethyl)-2-(6-(methylthio)benzo[d][1,3]dioxol-5-ylthio)-1H-imidazo[4,5-c]pyridin-4-amine (Compound 0303-87)

A mixture of TFA (1.8 ml) and compound 0305-87 (372 mg, 995 mmol) in CH₂Cl₂ (10 mL) was stirred at rt for 2 h. Saturated NaHCO₃ solution was added and was then extracted with dichloromethane. The organic phase was isolated and evaporated to obtain the title compound 0303-87 as a solid (260 mg, 88.7%): LCMS: 376 [M+1]⁺; $^1$H NMR (400 MHz, DMSO-d₆) δ 2.45 (s, 3H), 2.793 (t, 3H, J=6.6 Hz) 4.18 (t, 2H, J=6.6 Hz), 6.04 (s, 2H), 6.24 (s, 2H), 6.77 (s, 1H), 6.82 (d, 1H, J=6.0 Hz), 7.02 (s, 1H), 7.67 (d, 1H, J=6 Hz).

Step 56g. 2-(6-(Methylthio)benzo[d][1,3]dioxol-5-ylthio)-1-(2-(neopentylamino)ethyl)-1H-imidazo[4,5-c]pyridin-4-amine (Compound 87)

To a solution of compound 0303-87 (245 mg, 65.3 mmol) in methanol (15 mL) was added pivalaldehyde (84.41 g, 980 mmol). After stirred for 30 min at room temperature, NaBH₃CN (164.14 mg, 2.612 mmol) was added slowly, and the mixture was stirred for another 30 min. The mixture was diluted with water (500 mL) and extracted with dichloromethane (500 mL×2). The extract was concentrated and purified by column chromatography on silica gel (CH₂Cl₂/MeOH=50/1) and crystallization (CH₂Cl₂/Et₂O=1/4) to give the title compound 87 (52 mg, 17.9%) as a white solid: m.p. 170~170° C. LCMS: 446 [M+1]⁺; $^1$H NMR (DMSO-d⁶) δ 0.75 (s, 9H), 1.56 (s, 1H), 2.16 (s, 2H), 2.43 (s, 2H), 2.72 (s, 2H), 4.22 (t, 2H), 6.02 (s, 2H), 6.25 (s, 2H), 6.68 (s, 1H), 6.79 (d, 1H, J=5.2 Hz), 7.01 (s, 1H), 7.66 (d, 1H, J=5.2 Hz).

Example 57

Preparation of 2-(6-methoxybenzo[d][1,3]dioxol-5-ylthio)-1-(2-(neopentylamino)ethyl)-1H-imidazo[4,5-c]pyridin-4-amine (Compound 79)

Step 57a. 5-Methoxybenzo[d][1,3]dioxole (Compound 0106-79)

NaOH (1.2 g, 30 mmol) was added into a solution of sesamol (2.76 g, 20 mmol) in methanol (15 ml) at 0° C. The mixture was stirred for 1 h at 0° C. and then MeI (3.41 g, 24 mmol) was added into the above solution dropwise. The reaction mixture was stirred for 3 h at room temperature. The solution was concentrated and purified by column chromatography (petroleum ether) to give compound 0106-79 (2.5 g, 82%) as a colorless liquid: $^1$H NMR (DMSO-d⁶) δ 3.67 (s, 3H), 5.94 (s, 2H), 6.33 (dd, 1H), 6.60 (d, J=2.4 Hz, 1H), 6.79 (d, J=8.4 Hz, 1H).

Step 57b. 5-Iodo-6-methoxybenzo[d][1,3]dioxole (Compound 0107-79)

To a mixture of NIS (3.38 g, 15 mmol) and compound 0106-79 (2.28 g, 15 mmol) in MeCN (100 ml) was added TFA (3.42 g, 30 mmol). The reaction mixture was stirred overnight at room temperature. The reaction was concentrated and purified by column chromatography on silica (petroleum ether) to provide the title compound 0107-79 (3.3 g, 79%) as a white solid: $^1$H NMR (DMSO-d⁶) δ 3.74 (s, 3H), 5.60 (s, 2H), 6.85 (s, 1H), 7.27 (s, 1H).

Step 57c. 2-(6-Methoxybenzo[d][1,3]dioxol-5-ylthio)-1-(4-methoxybenzyl)-1H-imidazo[4,5-c]pyridin-4-amine (Compound 0205-79)

The title compound 0205-79 was prepared (800 mg, 26%) as a brown solid from compound 0204 (2.0 g, 7 mmol), compound 0107-79 (2.33 g, 8.4 mmol), NaOt-Bu (672 mg, 7 mmol), neocuproine hydrate (146 mg, 0.7 mmol) and CuI (133 mg, 0.7 mmol) in dry DMF (40 ml) using a procedure similar to that described for compound 0205-78 (Example 55): LCMS: 437 [M+1]⁺; $^1$H NMR (DMSO-d⁶) δ 3.70 (s, 6H), 5.43 (s, 2H), 5.99 (s, 2H), 6.79 (s, 1H), 6.84 (d, 3H), 7.01 (s, 1H), 7.08 (d, J=8.4 Hz, 2H), 7.43 (s, 2H), 7.69 (s, 1H).

Step 57d. 2-(6-Methoxybenzo[d][1,3]dioxol-5-ylthio)-1H-imidazo[4,5-c]pyridin-4-amine (Compound 0206-79)

The title compound 0206-79 was prepared (570 mg, 98%) as a brown solid from compound 0205-79 (0.8 g, 1.83 mmol) and $CF_3COOH$ (10 ml) using a procedure similar to that described for compound 0206-78 (Example 55): LCMS: 317 [M+1]$^+$; $^1$H NMR (DMSO-d$^6$) δ 3.74 (s, 3H), 6.07 (s, 2H), 6.82 (d, 2H), 7.01 (s, 1H), 7.10 (s, 1H), 7.60 (m, 2H), 12.71 (br, 1H).

Step 57e. tert-Butyl 2-(4-amino-2-(6-methoxybenzo[d][1,3]dioxol-5-ylthio)-1H-imidazo[4,5-c]pyridin-1-yl)ethylcarbamate (Compound 0305-79)

The title compound 0305-79 was prepared (200 mg, 25%) as a brown solid from compound 0206-79 (570 mg, 1.8 mmol), tert-butyl 2-bromoethylcarbamate (605 mg, 2.7 mmol) and $Cs_2CO_3$ (997 mg, 3.1 mmol) in DMF (15 ml) using a procedure similar to that described for compound 0305-87 (Example 56): LCMS: 460 [M+1]$^+$; $^1$H NMR (DMSO-d$^6$) δ 1.29 (s, 9H), 3.20 (m, 2H), 3.73 (s, 3H), 4.21 (t, J=5.6 Hz, 2H), 5.98 (s, 2H), 6.33 (s, 2H), 6.72 (d, J=6.0 Hz, 2H), 6.89 (s, 1H), 7.65 (d, J=6.0 Hz, 1H).

Step 57f. 1-(2-Aminoethyl)-2-(6-methoxybenzo[d][1,3]dioxol-5-ylthio)-1H-imidazo[4,5-c]pyridin-4-amine (Compound 0303-79)

A solution of compound 0305-79 (1.0 g, 2.18 mmol) and TFA (4 mL) in $CH_2Cl_2$ (50 mL) was stirred at room temperature for 2 h. The mixture was adjusted to pH 8~9 with saturated $Na_2CO_3$ aqueous solution and extracted by $CH_2Cl_2$. The organic layer was separated and dried over $Na_2SO_4$, concentrated to obtain the title compound 0303-79 (734 mg, 93%) which was used directly to the next step without further purification: LCMS: 360 [M+1]$^+$; $^1$H NMR (DMSO-d$^6$) δ 2.78 (t, J=6.4 Hz, 2H), 3.71 (m, 2H), 3.75 (s, 3H), 5.99 (s, 2H), 6.23 (s, 2H), 6.70 (s, 1H), 6.80 (d, J=6.0 Hz, 1H,), 6.91 (s, 1H), 7.66 (d, J=6.0 Hz, 1H).

Step 57g. 2-(6-methoxybenzo[d][1,3]dioxol-5-ylthio)-1-(2-(neopentylamino)ethyl)-1H-imidazo[4,5-c]pyridin-4-amine (Compound 79)

To a solution of compound 0303-79 (734 mg, 2.04 mmol) in methanol (40 mL) was added pivalaldehyde (352 mg, 4.08 mmol). After stirred for 30 min at room temperature, $NaBH_3CN$ (423 mg, 6.7 mmol) was added slowly, and the mixture was stirred for another 30 min. The mixture was diluted with water (100 mL) and extracted with dichloromethane (100 mL×2). The extract was concentrated and purified by column chromatography on silica gel ($CH_2Cl_2$/MeOH=50/1) and crystallization ($CH_2Cl_2$/$Et_2O$=1/4) to give the title compound 79 (151 mg, 17%) as a yellow solid: m.p. 164~167° C. LCMS: 430 [M+1]$^+$; $^1$H NMR (DMSO-d$^6$) δ 0.78 (s, 9H), 2.19 (s, 2H), 2.74 (t, J=6.0 Hz, 2H), 3.76 (s, 3H), 4.25 (t, J=6.0 Hz, 2H), 5.99 (s, 2H), 6.25 (s, 2H), 6.66 (s, 1H), 6.81 (d, J=6.0 Hz, 1H), 6.92 (s, 1H), 7.68 (d, J=6.0 Hz, 1H).

Example 58

Preparation of 2-(6-tert-butylbenzo[d][1,3]dioxol-5-ylthio)-1-(2-(neopentylamino)ethyl)-1H-imidazo[4,5-c]pyridin-4-amine (Compound 86)

Step 58a. 5-tert-Butylbenzo[d][1,3]dioxole (Compound 0106-86)

Aqueous NaOH (8 g, 100 mmol, 50%) was added slowly into a solution of 4-tert-butylcatechol (8.3 g, 50 mmol) in DMSO (100 ml) at 90° C. The solution was stirred for 1 h at 90° C. and then $CH_2I_2$ (10 ml) was added dropwise into the above solution. The mixture was stirred for 2 h at 90° C. and was distilled under reduced pressure to give the title compound 0106-86 (4 g, 45%) as a colorless liquid: $^1$H NMR (400M): (DMSO-d$^6$) δ 1.23 (s, 9H), 5.95 (s, 2H), 6.80 (s, 2H), 6.98 (s, 1H).

Step 58b. 5-tert-Butyl-6-iodobenzo[d][1,3]dioxole (Compound 0107-86)

$HNO_3$ (4.5 ml) was added into a solution of compound 0106-86 (8 g, 45 mmol) in $Ac_2O$ (90 ml) at -10° C. The mixture was stirred for 2 h at -10° C. The PH of the mixture was adjusted to 7-8 with 10% NaOH. Dichloromethane (200 ml) and water (100 ml) was added into the above mixture and was extracted with dichloromethane for 3 times. The organic phase was dried over $MgSO_4$, filtered and concentrated to give 5-tert-Butyl-6-nitrobenzo[d][1,3]dioxole (9.5 g, 95%) as a yellow liquid. 1H NMR (400M): (DMSO-d$^6$) δ 1.29 (s, 9H), 6.13 (s, 2H), 7.16 (s, 1H), 7.24 (s, 1H).

The above prepared 5-tert-Butyl-6-nitrobenzo[d][1,3]dioxole (1.1 g, 5 mmol), Fe (5.5 g, 100 mmol) and HCl (2 ml) was added into ethanol (6 ml) and water (18 ml). The mixture was stirred for 2 h at refluxed temperature. The PH was adjusted to 7-8 and the mixture was filtered and washed with methanol. The filtrate was concentrated and purified by column chromatography (petroleum ether/ethyl acetate 1%-5%) to give 6-tert-butylbenzo[d][1,3]dioxol-5-amine (240 mg, 25%) as a red solid. LCMS: 194 [M+1]$^+$; 1H NMR (400M): (DMSO-d$^6$) δ 1.28 (s, 9H), 4.46 (s, 2H), 5.77 (s, 2H), 6.32 (s, 1H), 6.63 (s, 1H).

6-tert-butylbenzo[d][1,3]dioxol-5-amine (1.55 g, 8.03 mmol) was added to a solution of $H_2SO_4$ (5.51 g, 56.22 mmol) in MeCN (60 ml) and water (60 ml) at 0° C. NaNO2 (0.61 g, 8.83 mmol) was then added to the above mixture. The reaction mixture was stirred for 1 h at 0° C. and then a solution of KI (4 g, 24.1 mmol) in water (60 ml) was added dropwise. The reaction mixture was stirred overnight at room temperature. The resulting solid was collected and purified by column chromatography (petroleum ether) to give the title compound 0107-86 (2.2 g, 90%) as a white solid. 1H NMR (400M): (DMSO-d$^6$) δ 1.44 (s, 9H), 6.00 (s, 2H), 7.01 (s, 1H), 7.46 (s, 1H).

Step 58c. 2-(6-tert-Butylbenzo[d][1,3]dioxol-5-ylthio)-1-(4-methoxybenzyl)-1H-imidazo[4,5-c]pyridin-4-amine (Compound 0205-86)

The title compound 0205-86 was prepared (1.8 g, 56%) as a brown solid from compound 0204 (2.0 g, 7 mmol), compound 0107-86 (2.13 g, 7 mmol), NaOt-Bu (672 mg, 7 mmol), neocuproine hydrate (146 mg, 0.7 mmol), and CuI (133 mg, 0.7 mmol) in dry DMF (40 ml) using a procedure similar to that described for compound 0205-78 (Example 55): LCMS: 463 [M+1]$^+$; $^1$H NMR (DMSO-d$^6$) δ 1.41 (s, 9H), 3.71 (s, 3H), 5.43 (s, 2H), 6.01 (s, 2H), 6.66 (s, 1H), 6.88 (d, J=8.8 Hz, 2H), 7.02 (s, 1H), 7.13 (m, 3H), 7.55 (s, 2H), 7.70 (s, 1H).

Step 58d. 2-(6-tert-Butylbenzo[d][1,3]dioxol-5-ylthio)-1H-imidazo[4,5-c]pyridin-4-amine (Compound 0206-86)

The title compound 0206-86 was prepared (1.3 g, 98%) as a brown solid from compound 0205-86 (1.8 g, 3.9 mmol) and CF$_3$COOH (20 ml) using a procedure similar to that described for compound 0206-78 (Example 55): LCMS: 343 [M+1]$^+$; $^1$H NMR (DMSO-d$^6$) δ 1.43 (s, 9H), 6.08 (s, 2H), 6.91 (d, J=5.6 Hz, 1H), 7.10 (d, 1H), 7.59 (d, J=6.8 Hz, 1H), 8.40 (s, 2H), 13.11 (s, 1H).

Step 58e. tert-Butyl 2-(4-amino-2-(6-tert-butylbenzo[d][1,3]dioxol-5-ylthio)-1H-imidazo[4,5-c]pyridin-1-yl)ethylcarbamate (Compound 0305-86)

The title compound 0305-86 was prepared (440 mg, 24%) as a brown solid from compound 0206-86 (1.3 g, 3.8 mmol), tert-butyl 2-bromoethylcarbamate (1.3 g, 5.7 mmol), and Cs$_2$CO$_3$ (2.1 g, 6.5 mmol) in DMF (40 ml) using a procedure similar to that described for compound 0305-87 (Example 56): LCMS: 486 [M+1]$^+$; $^1$H NMR (DMSO-d$^6$) δ 1.27 (s, 9H), 1.50 (s, 9H), 3.25 (d, 2H), 4.20 (s, 2H), 5.98 (s, 2H), 6.32 (s, 2H), 6.67 (s, 1H), 6.75 (d, J=4.8 Hz, 1H), 7.01 (m, 2H), 7.67 (d, J=5.2 Hz, 1H).

Step 58f. 1-(2-Aminoethyl)-2-(6-tert-butylbenzo[d][1,3]dioxol-5-ylthio)-1H-imidazo[4,5-c]pyridin-4-amine (Compound 0303-86)

The title compound 0303-86 was prepared (349 mg, 95%) from compound 0305-86 (445 g, 0.92 mmol) and TFA (4 mL) in CH$_2$Cl$_2$ (50 mL) using a procedure similar to that described for compound 0303-79 (Example 57): LCMS: 386 [M+1]$^+$; $^1$H NMR (DMSO-d$^6$) δ 1.50 (s, 9H), 2.78 (t, J=6.4 Hz, 2H), 3.17 (s, 2H), 4.10 (t, J=6.4H, 3H), 5.98 (s, 2H), 6.20 (s, 2H), 6.57 (s, 1H), 6.84 (d, J=6.0 Hz, 1H,), 7.02 (s, 1H), 7.69 (d, J=6.0 Hz, 1H).

Step 58g. 2-(6-tert-Butylbenzo[d][1,3]dioxol-5-ylthio)-1-(2-(neopentylamino)ethyl)-1H-imidazo[4,5-c]pyridin-4-amine (Compound 86)

The title compound 86 was prepared (190 mg, 46%) as yellow solid from compound 0303-86 (349 mg, 0.9 mmol), pivalaldehyde (156 mg, 1.8 mmol) and NaBH$_3$CN (226 mg, 3.6 mmol) using a procedure similar to that described for compound 79 (Example 57): m.p. 142~148° C. LCMS: 456 [M+1]$^+$; $^1$H NMR (DMSO-d$^6$) δ 0.77 (s, 9H), 1.52 (s, 9H), 2.18 (s, 2H), 2.76 (t, J=8.4 Hz, 2H), 4.22 (t, J=8.4 Hz, 2H), 5.97 (s, 2H), 6.34 (s, 2H), 6.51 (s, 1H), 6.84 (d, J=8.0 Hz, 1H), 7.02 (s, 1H), 7.70 (d, J=8.0 Hz, 1H).

Example 59

Preparation of 1-(2-(neopentylamino)ethyl)-2-(6-vinylbenzo[d][1,3]dioxol-5-ylthio)-1H-imidazo[4,5-c]pyridin-4-amine (Compound 84)

Step 59a. 2,4-Dihydroxy-3-nitropyridine (Compound 0108)

Fuming HNO$_3$ (90 mL) was added to a stirring solution of 2,4-dihydroxypyridine (0601) (100 g, 0.9 mol) in con. H$_2$SO$_4$ (300 mL) at 0° C. After 45 min, the solution was poured into crushed ice and the mixture was chilled in a freezer. The resulting precipitate was filtered, washed with cold water, and dried to give the title compound 0108 (135 g, 96%) as a light yellow solid: LCMS: 157 [M+1]$^+$; $^1$H NMR (DMSO-d$^6$) δ 6.05 (d, 1H, J=7.2 Hz), 7.47 (d, 1H, J=7.2 Hz), 11.91 (s, 1H), 12.47 (s, 1H).

Step 59b. 2,4-Dichloro-3-nitropyridine (Compound 0109)

Compound 0108 (10 g, 64 mmol) was dissolved in POCl$_3$ (70 mL) and heated overnight at 85° C. The excess POCl$_3$ was evaporated at atmosphere pressure. The residuum was neutralized (pH 7) with saturated NaHCO$_3$. The precipitate was filtered and dried to give the title compound 0109 (9.95 g, 80.5%) as a yellow solid: $^1$H NMR (CDCl$_3$) δ 7.47 (d, J=5.7 Hz, 1H), 8.44 (d, J=5.1 Hz, 1H).

Step 59c. tert-Butyl 2-(2-chloro-3-nitropyridin-4-ylamino)ethylcarbamate (Compound 0602-84)

A mixture of compound 0109 (55 g, 0.285 mol), tert-butyl N-(2-aminoethyl)carbamate (59.3 g, 0.37 mol) and Et$_3$N (43.2 g, 0.427 mol) in DMF (450 mL) was heated to 65° C. and stirred for 2.5 h. The DMF was removed under reduced pressure and the residue was poured into brine, extracted with EtOAc, dried and concentrated. The residue was then recrystallized with EtOH-water to provide the title compound 0602-84 (65 g, 72%) as a yellow solid: LCMS: 317 [M+1]$^+$; $^1$H NMR (DMSO-d$^6$) δ 1.36 (s, 9H), 3.10 (q, 2H, J$_1$=8.0 Hz, J$_2$=16 Hz), 3.30 (q, 2H, J$_1$=8.0 Hz, J$_2$=16 Hz), 6.98 (d, 2H, J=8 Hz), 7.38 (t, 1H, J=7.2 Hz), 8.04 (d, 1H, J=8.0 Hz).

Step 59d. tert-Butyl 2-(3-amino-2-chloropyridin-4-ylamino)ethylcarbamate (Compound 0603-84)

A mixture of compound 0602-84 (70 g, 0.221 mol), iron dust (62 g, 1.105 mol) and FeSO$_4$ 7H$_2$O (18.5 g, 66 mmol) in saturated NH$_4$Cl aqueous solution (750 mL) and MeOH (1400 mL) was heated to 80° C. for 3 h. The reaction was then filtered and washed with MeOH. The filtrate was concentrated and the residue was dissolved in dichloromethane. The dichloromethane solution was washed with water and concentrated to give the title compound 0603-84 (55 g, 87%) as a red solid. LCMS: 287 [M+1]$^+$; $^1$H NMR (DMSO-d$^6$) δ 1.37 (s, 9H), 3.13 (m, 4H), 4.69 (s, 2H), 5.76 (d, 1H, J=5.2 Hz), 6.45 (d, 1H, J=5.6 Hz), 6.92 (d, 1H, J=5.2 Hz), 7.41 (d, 1H, J=5.2 Hz).

Step 59e. tert-Butyl 2-(4-chloro-2-thioxo-2,3-dihydroimidazo[4,5-c]pyridin-1-yl)ethylcarbamate (Compound 604-84)

A mixture of compound 0603-84 (55 g, 0.192 mol), KOH (54 g, 0.959 mol), CS$_2$ (73 g, 0.959 mol) in EtOH (500 mL) and H$_2$O (50 mL) was stirred for 12 h at 85° C. Then the mixture was cooled to room temperature and diluted with water. The mixture was adjusted to pH 7 with AcOH, filtered to give the title compound 604-84 (54.5 g, 87%) as a yellow solid: LCMS: 329 [M+1]$^+$; $^1$H NMR (DMSO-d$^6$) δ 1.20 (s, 9H), 3.33 (s, 2H), 4.24 (t, 2H, J=4.8 Hz), 6.89 (t, 1H, J=5.2 Hz), 7.33 (d, 1H, J=5.2 Hz), 8.14 (d, 1H, J=5.2 Hz), 13.59 (s, 1H).

Step 59f. 1-(2-Aminoethyl)-4-chloro-1H-imidazo[4,5-c]pyridine-2(3H)-thione salt (Compound 0605-84)

A mixture of compound 0604-84 (63.8 g, 0.194 mol) and TFA (150 mL, 1.94 mol) in dichloromethane (750 mL) was stirred for 2 h at 25° C. The solvent was removed and dried to give the title compound 0605-84 (163 g) as a yellow solid which was used directly in next step without further purification: LCMS: 229 [M+1]$^+$; $^1$H NMR (DMSO-d$^6$) δ 3.27 (q, 2H, J$_1$=5.2 Hz, J$_2$=11.2 Hz), 4.47 (t, 2H, J=6.0 Hz), 7.55 (d, 1H, J=5.2 Hz), 7.92 (s, 2H), 8.20 (d, 1H, J=5.2 Hz), 12.22 (s, 2H), 13.78 (s, 1H).

Step 59g. 4-Chloro-1-(2-(neopentylamino)ethyl)-1H-imidazo[4,5-c]pyridine-2(3H)-thione (Compound 0606-84)

A suspension of compound 0605-84 (163 g, 0.194 mol) in MeOH (1300 mL) was adjusted to pH 8 with NEt$_3$ (~100 mL) at ice bath. Then pivalaldehyde (33.4 g, 0.388 mol) was added to the mixture and the mixture was stirred for 30 min at room temperature. NaBH$_3$CN (48.76 g, 0.776 mol) was added to the mixture and the mixture was stirred at room temperature overnight. The resulting solid was filtered to give the title compound 0606-84 (38.6 g, total yield of two steps: 67%) as a yellow solid: LCMS: 299 [M+1]$^+$; $^1$H NMR (DMSO-d$^6$) δ 0.79 (s, H), 2.36 (s, 2H) 2.95 (t, 2H, J=6.0 Hz), 4.32 (t, 2H, J=6.0 Hz), 7.49 (d, 1H, J=5.6 Hz), 8.07 (d, 1H, J=5.6 Hz).

Step 59h. 4-Amino-1-(2-(neopentylamino)ethyl)-1H-imidazo[4,5-c]pyridine-2(3H)-thione (Compound 0607-84)

A mixture of compound 0606-84 (11.4 g, 38.2 mmol) and sodium amide (30 g, 769 mmol) in 400 mL liquid ammonia was stirred at 25° C. for 24 h in a autoclave. Ammonia was volatilized before opening the autoclave. Water was added carefully until all solids were dissolved. This solution was adjust pH 7 with acetic acid and filtered to obtain the title compound 0607-84 (9 g, 84%) as a gray solid: LCMS: 280 [M+1]$^+$; $^1$H NMR (DMSO-d$^6$) δ 0.792 (s, 9H), 2.27 (s, 2H), 2.84 (m, 2H), 4.19 (m, 2H), 6.06 (s, 2H), 6.77 (m, 1H), 7.71 (m, 1H).

Step 59i. 5-Iodo-6-vinylbenzo[d][1,3]dioxole (Compound 0107-84)

To a solution of 3,4-(methylenedioxy)benzyl alcohol (1.8 g, 12 mmol) and CF$_3$COOAg (3.434 g, 15.5 mmol) in dry CHCl$_3$ (55 mL) at −5° C. was added I$_2$ (3.9 g, 15.5 mmol) in portion. The resulting yellow mixture was maintain at −5° C. for 5 min, then filtered. The filtrate was washed with 20% Na$_2$S$_2$O$_3$, dried and evaporated. The crude was purified by column chromatography on silica gel (petroleum ether) to obtain (6-iodobenzo[d][1,3]dioxol-5-yl)methanol (1.8 g, 56%) as a white solid. LCMS: 279[M+1]$^+$; $^1$H NMR (DMSO-d$^6$) δ 4.31 (d, 2H, J=4.2 Hz), 5.40 (t, 1H, J=4.2 Hz), 6.03 (s, 2H), 7.03 (s, 1H), 7.34 (s, 2H).

(6-Iodobenzo[d][1,3]dioxol-5-yl)methanol (2.7 g, 9.7 mmol) in dry CH$_2$Cl$_2$ was added dropwise to PCC (3.1 g, 14.6 mmol) in dry CH2Cl2 at 0° C. under N2 atmosphere. The mixture was stirred at room temperature for 20 h. After reaction, the crude product was purified by column chromatography on silica gel (petroleum ether) to obtain 6-iodobenzo[d][1,3]dioxole-5-carbaldehyde (2 g, 77%) as white solid. LCMS: 277[M+1]$^+$; $^1$H NMR (DMSO-d$^6$) δ 6.20 (s, 2H), 7.28 (s, 1H), 7.61 (s, 1H), 9.79 (s, 1H).

To a mixture of PPh$_3$CH$_3$I (5.5 g, 13.5 mmol) in dry THF was added t-BuOK (1.7 g, 14.8 mmol) at 0° C. The reaction mixture was stirred for 20 min. Above prepared compound 6-iodobenzo[d][1,3]dioxole-5-carbaldehyde in THF was then added to the reaction mixture dropwise. After reaction, the crude was purified by column chromatography on silica gel (petroleum ether) to obtain the title compound 0107-84 (2.65 g, 78%) as white solid. LCMS: 275 [M+1]$^+$; $^1$H NMR (DMSO-d$^6$) δ 5.24 (d, 1H, J=10.8Hz), 5.65 (d, 1H, J=17.1 Hz), 6.07 (s, 2H), 6.73 (m, 1H), 7.28 (s, 1H), 7.39 (s, 1 H).

Step 59j. 1-(2-(Neopentylamino)ethyl)-2-(6-vinylbenzo[d][1,3]dioxol-5-ylthio)-1H-imidazo[4,5-c]pyridin-4-amine (Compound 84)

A mixture of 0607-84 (100 mg, 0.36 mmol), 0107-84 (118 mg, 0.43 mmol), neocuproine hydrate (7.5 mg, 0.036 mmol), CuI (6.8 mg, 0.036 mmol) and NaOt-Bu (52 mg, 0.54 mmol) in anhydrous DMF (5 mL) was stirred for 12 h at 110° C. (oil bath) under nitrogen atmosphere. The solvent was poured into water, the mixture was then extracted with ethyl acetate. Solvents were removed and the crude was purified by prep-TLC (CH$_2$Cl$_2$/MeOH at 20/1) to obtain the title compound 84 (32 mg, 21%) as a yellow solid: m.p. 175~178° C. LCMS: 547[M+1]$^+$; $^1$H NMR (DMSO-d$^6$) δ 0.77 (s, 9H), 2.18 (s, 2H), 2.72 (t, 2H, J=4.5 Hz), 4.21 (t, 2H, J=4.8 Hz), 5.31 (d, 1H, J=8.4 Hz), 5.77 (d, 1H, J=13.5 Hz), 6.05 (s, 2H), 6.28 (s, 2H), 6.81 (m, 2H), 7.22 (m, 1H), 7.32 (s, 1H), 7.67 (d, 1H, J=4.5 Hz).

Example 60

Preparation of 6-(4-amino-1-(2-(neopentylamino)ethyl)-1H-imidazo[4,5-c]pyridin-2-ylthio)benzo[d][1,3]dioxole-5-carbonitrile (Compound 89)

Step 60a. 6-Iodobenzo[d][1,3]dioxole-5-carbonitrile (Compound 0107-89)

A mixture of 5,6-diiodobenzo[1,3]dioxole (1 g, 2.7 mmol) and CuCN (240 mg, 2.7 mmol) in DMF (15 mL) was stirred at 140° C. for 16 h, The mixture was filtered and the filtrate was added water. The resulting brown solid was filtered and purified by column chromatography on silica gel (petroleum ether/ethyl acetate=10/1) to obtain title compound 107-89 (450 mg, 61%) as a white solid: LCMS: 274[M+1]$^+$; $^1$H NMR (DMSO-d$^6$) δ 6.20 (s, 2H), 7.48 (s, 1H), 7.60 (s, 1H).

Step 60b. 6-(4-Amino-1-(2-(neopentylamino)ethyl)-1H-imidazo[4,5-c]pyridin-2-ylthio)benzo[d][1,3]dioxole-5-carbonitrile (Compound 89)

The title compound 89 was prepared (26 mg, 11.4%) as a yellow solid from compound 0607-84 (150 mg, 0.54 mmol), 0107-89 (176 mg, 0.64 mmol), neocuproine hydrate (11.2 mg, 0.054 mmol), CuI (10.2 mg, 0.054 mmol) and NaOt-Bu (77 mg, 0.81 mmol) in anhydrous DMF (5 mL) using a procedure similar to that described for compound 84 (Example 59): m.p. 126~130° C. LCMS: 425 [M+1]$^+$; $^1$H NMR (DMSO-d$^6$) δ 0.76 (s, 9H), 2.20 (s, 2H), 2.79 (t, 2H, J=4.8 Hz), 4.27 (t, 2H, J=4.5 Hz), 6.18 (s, 2H), 6.31 (s, 2H), 6.83 (d, 1H, J=4.5 Hz), 6.99 (s, 1H), 7.53 (s, 1H), 7.68 (s, 1H).

Example 61

Preparation of 2-(6-iodo-2,2-dimethylbenzo[d][1,3]dioxol-5-ylthio)-1-(2-(neopentylamino)ethyl)-1H-imidazo[4,5-c]pyridin-4-amine (Compound 101)

Step 61a. 5,6-Diiodo-2,2-dimethylbenzo[d][1,3]dioxole (Compound 0107-101)

A mixture of catechol (10 g, 91 mmol), 2,2-Dimethoxypropane (8.6 g, 82.6 mmol) and p-TsOH (33 mg, 0.17 mmol) in toluene (100 ml) was stirred at reflux for 6 h. After reaction, the mixture was cooled to room temperature and NaHCO$_3$ was added to neutralize the mixture. The solvent was removed and the residue was purified by distillation under reduced pressure at 36° C. to obtain 2,2-dimethylbenzo[d][1, 3]dioxole (2.34 g, 17%) as a yellow oil. $^1$H NMR (CDCl$_3$-d$^6$) δ 1.69 (s, 6H), 6.78 (m, 4H).

A solution of compound 2,2-dimethylbenzo[d][1,3]dioxole (2.34 g, 15.6 mmol) in MeCN (80 ml) was added NIS (10.5 g, 46.8 mmol) and followed with TFA (3.56 g, 31.2 mmol). The solution was stirred overnight at room temperature. The solution was concentrated and the residue was purified by column chromatography on silica (petroleum ether) to provide the title compound 0107-101 (5.6 g, 89%) as a white solid: $^1$H NMR(CDCl$_3$-d$^6$) δ 1.58 (s, 6H), 7.15 (s, 2H).

Step 61b. 2-(6-Iodo-2,2-dimethylbenzo[d][1,3]dioxol-5-ylthio)-1-(2-(neopentylamino)ethyl)-1H-imidazo[4,5-c]pyridin-4-amine (Compound 101)

The title compound 101 was prepared (31 mg, 10%) as a white solid from compound 0607-84 (200 mg, 0.72 mmol), 0107-101 (431 mg, 1.07 mmol), neocuproine hydrate (15 mg, 0.072 mmol), CuI (14 mg, 0.072 mmol) and NaOt-Bu (69 mg, 0.72 mmol) in anhydrous DMF (5 mL) using a procedure similar to that described for compound 84 (Example 59): m.p.: 214-216° C.; LCMS: 554 [M+1]$^+$; $^1$H NMR (DMSO-d$^6$) δ 0.76 (s, 9H), 1.60 (s, 6H), 2.16 (s, 2H), 2.73 (t, 2H, J=5.6 Hz), 4.24 (t, 2H, J=5.6 Hz), 6.36 (s, 2H), 6.51 (s, 1H), 6.84 (d, 2H, J=5.2 Hz), 7.38 (s, 1H), 7.70 (d, 1H, J=5.2 Hz).

Example 62

Preparation of 1-(2-(neopentylamino)ethyl)-2-(6-nitrobenzo[d][1,3]dioxol-5-ylthio)-1H-imidazo[4,5-c]pyridin-4-amine (Compound 113)

Step 62a. 5-Iodo-6-nitrobenzo[d][1,3]dioxole (Compound 0107-113)

1,3-Benzodioxole (10.0 g, 82 mmol) was added dropwise to a solution of con. HNO$_3$ (65%~68%, 18 g) in H$_2$O (39 g) at 60~65° C. The mixture was then heated to 90° C. and stirred for 2 h at this temperature. The mixture was cooled to room temperature and poured into ice/water, filtered to give compound 5-nitrobenzo[d][1,3]dioxole (12.0 g, 87%) as a yellow solid. LCMS: 168 [M+1]$^+$; $^1$H NMR (DMSO-d$^6$) δ 6.27 (s, 2H), 7.12 (d, 1H, J=12 Hz), 7.76 (d, 1H, 3.2 Hz), 7.91 (dd, 1H, J$_1$=12 Hz, J$_2$=3.2 Hz).

Compound 5-nitrobenzo[d][1,3]dioxole (5.0 g, 30 mmol) was added in one portion to a solution of fuming HNO$_3$ and con. HNO$_3$ (V/V=1/1, 120 mL) at −10 to −5° C. The mixture was stirred for 3 h at this temperature and poured into ice/water, filtered to get compound 5,6-dinitrobenzo[d][1,3]dioxole (7.0 g, quantitative) as a yellow solid. The compound was used directly without purification. $^1$H NMR (DMSO-d$^6$) δ 6.39 (s, 2H), 7.86 (s, 2H).

Compound 5,6-dinitrobenzo[d][1,3]dioxole (6.0 g, 28.3 mmol) was added to stirred glacial acetic acid (120 mL) under N$_2$ atmosphere. After the mixture was heated to boiling, the heat source was removed and iron powder (4.75 g) added with vigorous stirring. Quick spontaneous boiling occurred, the mixture turned dark and the exothermic reaction subsided (2~5 min). The mixture was refluxed for 10 min and poured into ice/water. The orange-red product was isolated by filtration, dissolved in glacial acetic acid, and the solution filtered while hot. The filtrate was poured into ice-cold water. The orange-red solid product was isolated by filtration and dried to provide compound 6-nitrobenzo[d][1,3]dioxol-5-amine (4.35 g, 84%). LCMS: 183 [M+1]$^+$; $^1$H NMR (DMSO-d$^6$) δ 6.06 (s, 2H), 6.51 (s, 1H), 7.36 (s, 1H), 7.73 (s, 2H).

A suspension of compound 6-nitrobenzo[d][1,3]dioxol-5-amine (2.65 g, 14.6 mmol) in con. HCl (15 mL) and water (5 mL) was heated on a steam bath for 5 min and then cooled to 5° C. with stirring. A solution of sodium nitrite (1.0 g, 14.4 mmol) in water (15 mL) was added until all the solids dissolved. The solution was stirred for additional 5 min and a solution of potassium iodide (2.4 g, 14.5 mmol) in water was then added rapidly with vigorous stirring at 5° C. The mixture was filtered and the residue was dissolved with dichloromethane, dried and purified by column chromatograph (ethyl acetate/petroleum ether=1/10) to provide the title compound 0107-113 (1.6 g, 38%) as a yellow solid. 1H NMR (DMSO-d$^6$) δ 6.24 (s, 2H), 7.64 (s, 1H), 7.67 (s, 1H).

Step 62b. 1-(2-(Neopentylamino)ethyl)-2-(6-nitrobenzo[d][1,3]dioxol-5-ylthio)-1H-imidazo[4,5-c]pyridin-4-amine (Compound 113)

The title compound 113 was prepared (40 mg, 26%) as a yellow solid from compound 0607-84 (100 mg, 0.358 mmol), 0107-113 (137 mg, 0.466 mmol), necocuproine (8 mg, 0.036 mmol), CuI (7 mg, 0.036 mmol), and NaO-t-Bu (52 mg, 0.537 mmol) in anhydrous DMF (5 ml) using a procedure similar to that described for compound 84 (Example 59): m.p. 111~114° C. LCMS: 445[M+1]$^+$, $^1$H NMR (DMSO-d$^6$) δ 0.72 (s, (H), 1.61 (s, 1H), 2.12 (s, 2H), 2.74 (t, 2H, J=5.2 Hz), 4.21 (t, 2H, J=5.2 Hz), 6.16 (s, 1H), 6.18 (s, 2H), 6.49 9 s, 2H), 6.85 (d, 1H, J=6.4 Hz), 7.73 (d, 1H, J=6.4 hz), 7.85 (s, 1H).

Example 63

Preparation of 2-(6-(dimethylamino)benzo[d][1,3]dioxol-5-ylthio)-1-(2-(neopentylamino)ethyl)-1H-imidazo[4,5-c]pyridin-4-amine (Compound 111)

Step 63a. 6-Iodo-N,N-dimethylbenzo[d][1,3]dioxol-5-amine (Compound 0107-111)

To a solution of 3,4-(Methylenedioxy)aniline (8 g, 58.3 mmol) in AcOH (120 ml) was added Ac2O (48 mL). The mixture was stirred for overnight. After reaction, the mixture was poured into saturated NaHCO$_3$ solution, and then filtered. The filtrate was extracted with ethyl acetate to give N-(benzo[d][1,3]dioxol-5-yl)acetamide (10 g, 95%). LCMS: 180[M+1]$^+$; $^1$H NMR (DMSO-d$^6$) δ 2.0 (s, 3H), 5.96 (s, 2H), 6.82 (d, 1H, J=8.1 Hz), 6.91 (d, 1H, J=2.1 Hz), 7.30 (d, 1H, J=1.8 Hz), 9.84 (s, 1H).

A 1.0 M solution of iodine monochloride in methylene chloride (72.6 mL) was added dropwise to a solution of N-(benzo[d][1,3]dioxol-5-yl)acetamide (10 g, 55.8 mmol) in methylene chloride (66 mL) and acetic acid (11 mL). The mixture was stirred under nitrogen overnight and then washed with saturated sodium thiosulfate (2×150 mL) and brine (150 mL). The methylene chloride solution was dried (MgSO$_4$) and evaporated, and the residue was purified by column chromatography on silica gel (CH$_2$Cl$_2$/petroleum at 20/1) to obtain N-(6-iodobenzo[d][1,3]dioxol-5-yl)acetamide (3.7 g, 22%) as a white solid. LCMS: 306 [M+1]$^+$; $^1$H NMR (DMSO-d$^6$) δ 2.00 (s, 3H), 6.06 (s, 2H), 6.95 (s, 1H), 7.37 (s, 1H), 9.34 (s, 1H).

A solution of N-(6-iodobenzo[d][1,3]dioxol-5-yl)acetamide (200 mg, 0.656 mmol) and NaOH (1.31 g, 32.8 mmol)

in ethanol (26 mL) and water (6 mL) was heated to reflux with stirring for 4 h. The mixture was cooled and the solvent was removed under vacuum. The residue was partitioned between methylene chloride (100 mL) and water (100 mL). The organic layer was washed with water (2×100 mL), dried (MgSO$_4$) and evaporated under vacuum to give 6-iodobenzo [d][1,3]dioxol-5-amine (170 mg, 98%) as orange solid. LCMS: 264 [M+1]$^+$; $^1$H NMR (DMSO-d$^6$) δ 4.88 (s, 2H), 5.87 (s, 2H), 6.47 (s, 1H), 7.07 (s, 1H).

To a solution of 6-iodobenzo[d][1,3]dioxol-5-amine (1 g, 3.8 mmol) and paraformaldehyde (1.14 g, 38 mmol) in methanol (10 mL) was added NaBH$_3$CN (2.39 g, 38 mmol) slowly with stirring. The mixture was heated to 50° C. for 4 h. Water (100 mL) was added and extracted with methylene chloride (100 mL). The organic layer was washed with brine (100 mL), dried (MgSO$_4$) and evaporated under vacuum to give crude title compound 0107-111 (1.16 g) as a brown oil which was used directly to the next step without further purification. LCMS: 292 [M+1]$^+$; $^1$H NMR (DMSO-d$^6$) δ 2.56 (s, 6H), 6.02 (s, 2H), 6.96 (s, 1H), 7.32 (s, 1H).

Step 63b. 2-(6-(Dimethylamino)benzo[d][1,3]dioxol-5-ylthio)-1-(2-(neopentylamino)ethyl)-1H-imidazo [4,5-c]pyridin-4-amine (Compound 111)

The title compound 111 was prepared (20 mg, 6.6%) as a brown solid from compound 0607-84 (190 mg, 0.68 mmol), 0107-111 (200 mg, 0.68 mmol), neocuproine hydrate (14 mg, 0.068 mmol), CuI (12 mg, 0.068 mmol) and NaOt-Bu (66 mg, 0.068 mmol) in anhydrous DMF (6 mL) using a procedure similar to that described for compound 84 (Example 59): LCMS: 443 [M+1]$^+$; $^1$H NMR (DMSO-d$^6$) δ 0.748 (s, 9H), 2.16 (s, 2H), 2.63 (s, 6H), 2.74 (t, 2H, J=6.0 Hz), 4.21 (t, 2H, J=6.0 Hz) 5.94 (s, 2H), 6.16 (s, 1H), 6.38 (s, 2H), 6.84 (d, 1H, J=6.0 Hz), 7.01 (s, 1H), 7.70 (d, 1H, J=5.6 Hz).

Example 64

Preparation of 2-(6-((dimethylamino)methyl)benzo [d][1,3]dioxol-5-ylthio)-1-(2-(neopentylamino) ethyl)-1H-imidazo[4,5-c]pyridin-4-amine (Compound 115)

Step 64a. N-((6-Iodobenzo[d][1,3]dioxol-5-yl)methyl)acetamide compound (Compound 0107-115)

To a solution of 3,4-methylenedioxybenzylamine (10 g, 66.2 mmol) in acetic acid (50 mL) was added acetic anhydride (15.27 g, 150 mmol). The mixture was stirred at 20° C. for 30 minutes. Then it was adjusted to PH7 with 10% NaOH. The mixture was filtered to obtain a solid which was washed water and dried in vacuum to give N-(benzo[d][1,3]dioxol-5-ylmethyl)acetamide as a white solid (9.24 g, 77%). LC-MS: 194 [M+1]$^+$; $^1$H-NMR (DMSO-d$^6$): δ 1.84 (s, 3H), 4.12 (d, 2H, J=6.4 Hz), 5.98 (s, 2H), 6.71 (m, 2H), 6.83 (m, 2H), 8.28 (s, 1H).

N-(benzo[d][1,3]dioxol-5-ylmethyl)acetamide (9.24 g, 47.9 mmol) was added to 1.0 M solution of iodine monochloride in methylene chloride (80 mL). The mixture was stirred at room temperature for 2 hours, and then the mixture was poured into 10% Na$_2$S$_2$O$_3$ and stirred until the red color faded. It was then extracted with CH$_2$Cl$_2$ and the organic layer was washed with water and brine, dried and concentrated to get the crude product which was purified by column chromatography (mobile phase: petroleum/methylene chloride=1/19) to give N-((6-iodobenzo[d][1,3]dioxol-5-yl)methyl)acetamide compound as a white solid (5.82 g, 38%). LC-MS: 320 [M+1]$^+$. $^1$H-NMR (DMSO-d$^6$): δ 1.89 (s, 3H), 4.11 (d, 2H, J=6.0 Hz), 6.04 (s, 2H), 7.07 (s, 1H), 7.37 (s, 1H), 8.28 (t, 1H, J=6.0 Hz).

N-((6-Iodobenzo[d][1,3]dioxol-5-yl)methyl)acetamide (2.4 g, 7.5 mmol) was added to methanolic hydrochloric acid solution (4 N) (60 mL). The mixture was stirred at 80° C. overnight. Solvent was removed and the residue was dissolved in water, adjusted to PH 7 with 10% NaHCO$_3$, filtered to obtain (6-iodobenzo[d][1,3]dioxol-5-yl)methanamine as a yellow solid (1.76 g, 85%). LC-MS: 278 [M+1]$^+$. $^1$H-NMR (DMSO-d$^6$): δ 1.88 (s, 2H), 3.57 (s, 2H), 6.02 (s, 2H), 7.13 (s, 1H), 7.33 (s, 1H).

A mixture of (6-iodobenzo[d][1,3]dioxol-5-yl)methanamine (1.76 g, 6.35 mmol), NaBH$_3$CN (4.00 g, 63.5 mmol), and formaldehyde (1.9 g, 63.5 mmol) in methanol (10 mL) was stirred at 50° C. for 2 hours. The solvent was removed and the residue was dissolved in CH$_2$Cl$_2$, washed with water and brine, dried and concentrated to give the title compound 0107-115 as a yellow oil (700 mg, 36%). LC-MS: 306 [M+1]$^+$. $^1$H-NMR (DMSO-d$^6$): δ 2.15 (s, 6H), 3.29 (s, 2H), 6.02 (s, 2H), 6.95 (s, 1H), 7.33 (s, 1H).

Step 64b. 2-(6-((Dimethylamino)methyl)benzo[d][1, 3]dioxol-5-ylthio)-1-(2-(neopentylamino)ethyl)-1H-imidazo[4,5-c]pyridin-4-amine (Compound 115)

The title compound 115 was prepared (27 mg, 15%) as a yellow solid from compound 0607-84 (100 mg, 0.358 mmol), 0107-115 (120 mg, 0.394 mmol), CuI (7 mg, 0.0358 mmol), t-BuONa (34 mg, 0.0358 mmol), neocuporine (8 mg, 0.0358 mmol) and DMF (3 mL) using a procedure similar to that described for compound 84 (Example 59): m.p. 81~86° C. LC-MS: 457.2 [M+1]$^+$. $^1$H-NMR (DMSO-d$^6$): δ 0.77 (s, 9H), 2.16 (s, 8H), 2.70 (m, 2H), 3.48 (s, 2H), 4.18 (m, 2H), 6.00 (s, 2H), 6.28 (m, 2H), 6.64 (s, 1H), 6.80 (m, 1H), 6.97 (s, 1H), 7.68 (m, 1H).

Example 65

Preparation of 2-(6-ethylbenzo[d][1,3]dioxol-5-ylthio)-1-(2-(neopentylamino)ethyl)-1H-imidazo[4,5-c]pyridin-4-amine (Compound 85)

Step 65a. 5-Ethyl-6-iodobenzo[d][1,3]dioxole (Compound 0107-85)

t-BuOK (7.77 g, 69.3 mmol) was added portions to a suspension of compound methyltriphenylphosphonium iodide (28.0 g, 68.3 mmol) in dry THF (250 mL) over 10 min at 0° C. The resulting yellow suspension was stirred for 20 min at this temperature. A solution of piperonal (8.0 g, 53.3 mmol) in dry THF (25 mL) was added dropwise to the above suspension and the mixture was stirred for 1 h at 0° C. The reaction mixture was concentrated and the residue was purified by column chromatograph (petroleum ether) to provide compound 5-vinylbenzo[d][1,3]dioxole (7.4 g, 94%) as colorless liquid. $^1$H-NMR (DMSO-d$^6$): 5.09 (d, 1H, J=11.2 Hz), 5.68 (d, 1H, J=18 Hz), 6.00 (s, 2H), 6.63 (1, 1H, J$_1$=11.2 Hz, J$_2$=18 Hz), 6.85 (m, 2H), 7.11 (s, 1H).

A mixture of 5-vinylbenzo[d][1,3]dioxole (6.0 g, 40.5 mmol) and 10% Pd/C (840 mg) in MeOH (50 mL) was hydrogenated for 8 h at 10 atm. Then Pd/C was filtered and the MeOH was removed to give compound 5-ethylbenzo[d][1,3] dioxole (3.0 g, 50%) as colorless liquid. $^1$H-NMR (DMSO-d$^6$): δ 1.11 (t, 3H, J=7.2 Hz), 2.50 (q, 2H, J$_1$=7.2 Hz, J$_2$=16 Hz), 5.93 (s, 2H), 6.64 (d, 1H, J=8 Hz), 6.77 (m, 2H).

A mixture of compound 5-ethylbenzo[d][1,3]dioxole (3.0 g, 20 mmol), NIS (6.0 g, 22 mmol) and TFA (2.3 g, 20 mmol) in 30 mL of $CH_3CN$ was stirred for 5 hours at room temperature. Saturated $Na_2S_2O_3$ solution was then added dropwise to the mixture until the color was faded. $CH_3CN$ was evaporated in vacuo and the mixture was extracted with ethyl acetate (20 mL×2). The organic phase was dried and concentrated to obtain the title compound 0107-85 (5.3 g, 96%) as a yellow solid. GC-MS 276 $[M+1]^+$, $^1H$ NMR (DMSO-$d^6$): δ 1.06 (t, 3H, J=7.6 Hz), 2.57 (q, 2H, J=7.6 Hz), 6.00 (s, 2H), 6.93 (s, 1H), 7.30 (s, 1H).

Step 65b. 2-(6-Ethylbenzo[d][1,3]dioxol-5-ylthio)-1-(2-(neopentylamino)ethyl)-1H-imidazo[4,5-c]pyridin-4-amine (Compound 85)

The title compound 85 was prepared (40 mg, 26%) as a yellow solid from compound 0607-84 (100 mg, 0.358 mmol), 0107-85 (127 mg, 0.466 mmol), neocuproine (8 mg, 0.0358 mmol), CuI (7 mg, 0.036 mmol), and t-BuONa (52 mg, 0.537 mmol) in anhydrous DMF (5 ml) using a procedure similar to that described for compound 84 (Example 59): m.p. 145~147° C., LCMS: 428 $[M+1]^+$ $^1H$ NMR (DMSO-$d^6$): δ 0.79 (s, 9H), 1.14 (t, 3H, J=7.2 Hz), 1.65 (bs, 1H), 2.18 (s, 2H), 2.75 (t, 2H, J=5.6 Hz), 2.78 (q, 2H, J=7.6 Hz), 4.23 (t, 2H, J=6.0 Hz), 6.01 (s, 2H), 6.21 (s, 2H), 6.72 (s, 1H), 6.82 (d, 1H, J=5.6 Hz), 6.96 (s, 1H), 7.69 (d, 1H, J=5.2 Hz)

Biological Assays:

As stated hereinbefore the derivatives defined in the present invention possess anti-proliferation activity. These properties may be assessed, for example, using one or more of the procedures set out below:

(a) An In Vitro Assay which Determines the Ability of a Test Compound to Inhibit Hsp90 Chaperone Activity.

The Hsp90 chaperone assay was performed to measure the ability of HSP90 protein to refold the heat-denatured luciferase protein. HSP90 was first incubated with different concentrations of test compounds in denaturation buffer (25 mM Tris, pH7.5, 8 mM $MgSO_4$, 0.01% bovine gamma globulin and 10% glycerol) at room temperature for 30 min. Luciferase protein was added to denaturation mix and incubated at 50° C. for 8 min. The final concentration of HSP90 and luciferase in denaturation mixture were 0.375 μM and 0.125 μM respectively. A 5 μl sample of the denatured mix was diluted into 25 μl of renaturation buffer (25 mM Tris, pH7.5, 8 mM MgSO4, 0.01% bovine gamma globulin and 10% glycerol, 0.5 mM ATP, 2 mM DTT, 5 mM KCl, 0.3 μM HSP70 and 0.15 μM HSP40). The renaturation reaction was incubated at room temperature for 150 min, followed by dilution of 10 μl of the renatured sample into 90 μl of luciferin reagent (Luclite, PerkinElmer Life Science). The mixture was incubated at dark for 5 min before reading the luminescence signal on a TopCount plate reader (PerkinElmer Life Science).

(b) HSP90 Competition Binding (Fluorescence Polarization) Assay.

A fluorescein isothiocyanate (FITC) labeled GM was purchase from InvivoGen (ant-fgl-1). The interaction between HSP90 and labeled GM forms the basis for the fluorescence polarization assay. A free and fast-tumbling FITC labeled GM emits random light with respect to the plane of polarization plane of excited light, resulting in a lower polarization degree (mP) value. When GM is bound to HSP90, the complex tumble slower and the emitted light is polarized, resulting in a higher mP value. This competition binding assay was performed in 96-well plate and with each assay contained 10 and 50 nM of labeled GM and purified HSP90 protein (Assay Design, SPP-776F) respectively. The assay buffer contained 20 mM HEPES (pH 7.3), 50 mM KCl, 1 mM DTT, 50 mM $MgCl_2$, 20 mM $Na_2MoO_4$, 0.01% NP40 with 0.1 mg/ml bovine gamma-globulin. Compounds are diluted in DMSO and added to the final assay before labeled GM with concentration range from 20 uM to 2 nM. mP value was determined by BioTek Synergy II with background subtraction after 24 hours of incubation at 4° C.

The following TABLE B lists compounds representative of the invention and their activity in HSP90 assays. In these assays, the following grading was used: I≧10 μM, 10 μM>II>1 μM, 1 μM>III>0.1 μM, and IV≦0.1 μM for $IC_{50}$.

TABLE B

| Compound No. | HSP90 Chaperone ($IC_{50}$) | HSP90 Binding ($IC_{50}$) |
| --- | --- | --- |
| 1 | III | III |
| 2 | III | III |
| 3 | III | IV |
| 4 |  | III |
| 7 |  | III |
| 9 |  | I |
| 11 | I | I |
| 12 | II | III |
| 13 | II | II |
| 14 | II | II |
| 15 |  | I |
| 16 |  | I |
| 17 | I | I |
| 18 |  | II |
| 19 | II | II |
| 21 |  | I |
| 22 |  | II |
| 23 |  | III |
| 24 |  | II |
| 25 |  | III |
| 26 |  | II |
| 27 |  | II |
| 28 |  | III |
| 29 |  | II |
| 30 |  | III |
| 32 |  | III |
| 33 |  | III |
| 34 | III | IV |
| 37 |  | IV |
| 40 |  | III |
| 42 |  | III |
| 44 |  | III |
| 46 |  | III |
| 48 |  | II |
| 50 |  | III |
| 51 |  | II |
| 52 |  | III |
| 53 |  | II |
| 54 |  | II |
| 56 |  | III |
| 58 |  | III |
| 60 |  | III |
| 61 |  | III |
| 62 |  | III |
| 64 |  | II |
| 66 |  | III |
| 68 |  | III |
| 70 |  | III |
| 72 |  | III |
| 74 |  | III |
| 76 |  | III |
| 77 |  | III |
| 78 |  | II |
| 79 |  | III |
| 84 |  | III |
| 85 |  | III |
| 86 |  | II |
| 87 |  | III |
| 89 |  | III |
| 101 |  | I |
| 111 |  | IV |

TABLE B-continued

| Compound No. | HSP90 Chaperone (IC$_{50}$) | HSP90 Binding (IC$_{50}$) |
|---|---|---|
| 113 | | III |
| 115 | | I |

A representative compound of the invention has been shown to have a favorable pharmacological kinetic (PK) profile and a high degree of brain penetration following systemic administration. In a tMAO model (Dellovade, T. *Annu. Rev. Neurosci.*, 2006, 29, 539-563), a single iv dose of 10 mg/kg of the compound in rat has been demonstrated to significantly reduce total brain infarct volume by approximately 33% at 4 hours post-tMCAO.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by formula I:

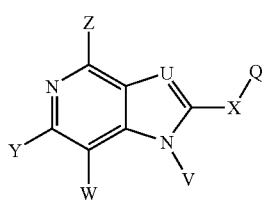

(I)

or its geometric isomers, enantiomers, diastereomers, racemates, pharmaceutically acceptable salts and solvates thereof, wherein
U is N;
W is hydrogen, halogen, amino, hydroxy, thiol, alkyl, substituted alkyl, substituted or unsubstituted alkoxy, substituted or unsubstituted alkylamino, substituted or unsubstituted dialkylamino, substituted or unsubstituted alkylthio, substituted or unsubstituted alkylsulfonyl, CF$_3$, NO$_2$, CN, N$_3$, sulfonyl, acyl, aryl, substituted aryl, heteroaryl, substituted heteroaryl, heterocyclic, substituted heterocyclic, cycloalkyl, or substituted cycloalkyl;
X is O, S, S(O), S(O)$_2$, N(R$_8$), or C(O) where R$_8$ is hydrogen, acyl, aliphatic or substituted aliphatic;
Y is independently hydrogen, halogen, NO$_2$, CN, or lower alkyl;
Z is amino, substituted or unsubstituted alkylamino, substituted or unsubstituted dialkylamino, substituted or unsubstituted alkylcarbonylamino;
Q is aryl, substituted aryl, heteroaryl, substituted heteroaryl, cycloalkyl, or heterocycloalkyl;
V is hydrogen, straight- or branched-, substituted or unsubstituted alkyl, substituted or unsubstituted alkenyl, substituted or unsubstituted alkynyl.

2. A compound represented by formula (II):

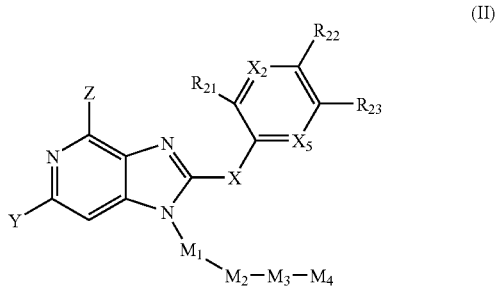

(II)

or its geometric isomers, enantiomers, diastereomers, racemates, pharmaceutically acceptable salts and solvates thereof, wherein X$_2$ and X$_5$ are independently CH or N; R$_{21}$-R$_{23}$ are independently selected from the group consisting of hydrogen, halogen, amino, substituted amino, hydroxy, substituted hydroxyl, thiol, substituted thiol, alkyl, substituted alkyl, alkenyl, substituted alkenyl, alkynyl, substituted alkynyl, substituted or unsubstituted alkoxy, substituted or unsubstituted alkylamino, substituted or unsubstituted dialkylamino, substituted or unsubstituted alkylthio, substituted or unsubstituted alkylsulfonyl, CF$_3$, NO$_2$, CN, N$_3$, substituted carbonyl, sulfonyl, acyl, aryl, substituted aryl, heteroaryl, substituted heteroaryl, heterocyclic, substituted heterocyclic, cycloalkyl, or substituted cycloalkyl; R$_{22}$ and R$_{23}$ can be taken together from the carbon to which they are attached to form a saturated or unsaturated fused 5-8 membered cyclic ring optionally substituted with 0-3 heteroatom; M$_1$ is absent, C$_1$-C$_6$ alkyl, C$_2$-C$_6$ alkenyl, C$_2$-C$_6$ alkynyl, aryl or heteroaryl; M$_2$ is absent, O, S, SO, SO$_2$, N(R$_8$), or C=O; M$_3$ is absent, C=O, O, S, SO, SO$_2$ or N(R$_8$); M$_4$ is hydrogen, halogen, CN, N$_3$, hydroxy, substituted hydroxy, amino, substituted amino, CF$_3$, C$_1$-C$_6$ alkyl, C$_2$-C$_6$ alkenyl, C$_2$-C$_6$ alkynyl, cycloalkyl, heterocyclic, aryl or heteroaryl;
X is O, S, S(O), S(O)$_2$, N(R$_8$), or C(O);
Y is independently hydrogen, halogen, NO$_2$, CN, or lower alkyl; and,
Z is amino, substituted or unsubstituted alkylamino, substituted or unsubstituted dialkylamino, substituted or unsubstituted alkylcarbonylamino.

3. A compound represented by formula (III):

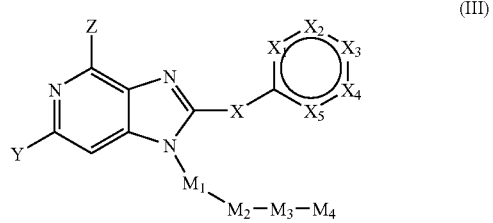

(III)

or its geometric isomers, enantiomers, diastereomers, racemates, pharmaceutically acceptable salts, and solvates thereof, wherein X$_1$-X$_5$ are independently N or CR$_{21}$; where R$_{21}$ is independently selected from the group consisting of hydrogen, halogen, amino, substituted amino, hydroxy, substituted hydroxy, thiol, substituted thiol, alkyl, substituted alkyl, alkenyl, substituted alkenyl, alkynyl, substituted alkynyl, substituted or unsubstituted alkoxy, substituted or unsubstituted alkylamino, substituted or unsubstituted dialkylamino, substituted or unsubstituted alkylthio, substituted or unsubstituted alkylsulfonyl, $CF_3$, $NO_2$, CN, $N_3$, substituted carbonyl, sulfonyl, acyl, aryl, substituted aryl, heteroaryl, substituted heteroaryl, heterocyclic, substituted heterocyclic, cycloalkyl, or substituted cycloalkyl; $M_1$ is absent, $C_1$-$C_6$ alkyl, $C_2$-$C_6$ alkenyl, $C_2$-$C_6$ alkynyl, aryl or heteroaryl; $M_2$ is absent, O, S, SO, $SO_2$, $N(R_8)$, or C=O; $M_3$ is absent, C=O, O, S, SO, $SO_2$ or $N(R_8)$; $M_4$ is hydrogen, halogen, CN, $N_3$, hydroxy, substituted hydroxy, amino, substituted amino, $CF_3$, $C_1$-$C_6$ alkyl, $C_2$-$C_6$ alkenyl, $C_2$-$C_6$ alkynyl, cycloalkyl, heterocyclic, aryl or heteroaryl;

X is O, S, S(O), $S(O)_2$, $N(R_8)$, or C(O);

Y is independently hydrogen, halogen, $NO_2$, CN, or lower alkyl; and,

Z is amino, substituted or unsubstituted alkylamino, substituted or unsubstituted dialkylamino, substituted or unsubstituted alkylcarbonylamino.

4. A compound according to claim 2 represented by formula (IV):

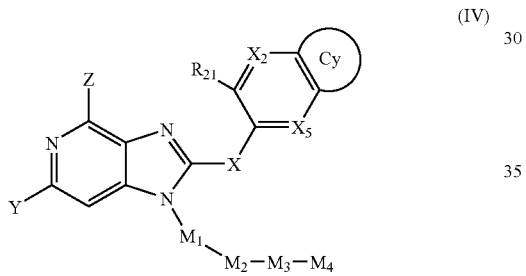

(IV)

or its geometric isomers, enantiomers, diastereomers, racemates, pharmaceutically acceptable salts, and solvates thereof, wherein $X_2$ and $X_5$ are independently CH or N; $R_{21}$ is independently selected from the group consisting of hydrogen, halogen, amino, substituted amino, hydroxy, substituted hydroxy, thiol, substituted thiol, alkyl, substituted alkyl, alkenyl, substituted alkenyl, alkynyl, substituted alkynyl, substituted or unsubstituted alkoxy, substituted or unsubstituted alkylamino, substituted or unsubstituted dialkylamino, substituted or unsubstituted alkylthio, substituted or unsubstituted alkylsulfonyl, $CF_3$, $NO_2$, CN, $N_3$, substituted carbonyl, sulfonyl, acyl, aryl, substituted aryl, heteroaryl, substituted heteroaryl, heterocyclic, substituted heterocyclic, cycloalkyl, or substituted cycloalkyl; Cy is a saturated or unsaturated fused 5-8 membered cyclic ring optionally substituted with 0-3 heteroatom; $M_1$ is absent, $C_1$-$C_6$ alkyl, $C_2$-$C_6$ alkenyl, $C_2$-$C_6$ alkynyl, aryl or heteroaryl; $M_2$ is absent, O, S, SO, $SO_2$, $N(R_8)$, or C=O; $M_3$ is absent, C=O, O, S, SO, $SO_2$ or $N(R_8)$; $M_4$ is hydrogen, halogen, CN, $N_3$, hydroxy, substituted hydroxy, amino, substituted amino, $CF_3$, $C_1$-$C_6$ alkyl, $C_2$-$C_6$ alkenyl, $C_2$-$C_6$ alkynyl, cycloalkyl, heterocyclic, aryl or heteroaryl; and X, Y and Z are as previously defined in claim 2.

5. A compound according to claim 2 represented by formula

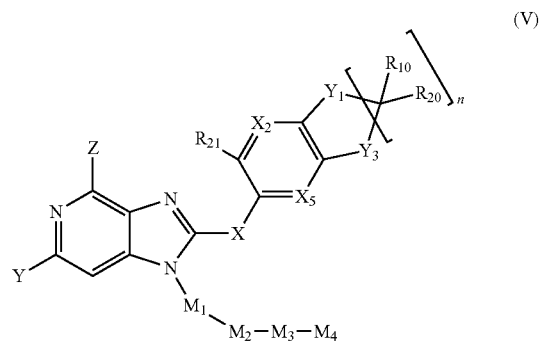

(V)

or its geometric isomers, enantiomers, diastereomers, racemates, pharmaceutically acceptable salts, and solvates thereof, wherein $X_2$ and $X_5$ are independently CH or N; $R_{21}$ is independently selected from the group consisting of hydrogen, halogen, amino, substituted amino, hydroxy, substituted hydroxy, thiol, substituted thiol, alkyl, substituted alkyl, alkenyl, substituted alkenyl, alkynyl, substituted alkynyl, substituted or unsubstituted alkoxy, substituted or unsubstituted alkylamino, substituted or unsubstituted dialkylamino, substituted or unsubstituted alkylthio, substituted or unsubstituted alkylsulfonyl, $CF_3$, $NO_2$, CN, $N_3$, substituted carbonyl, sulfonyl, acyl, aryl, substituted aryl, heteroaryl, substituted heteroaryl, heterocyclic, substituted heterocyclic, cycloalkyl, or substituted cycloalkyl; $Y_1$ and $Y_3$ are independently O, S, $N(R_8)$, $CH(R_{21})$; n is 1, 2, or 3; $M_1$ is absent, $C_1$-$C_6$ alkyl, $C_2$-$C_6$ alkenyl, $C_2$-$C_6$ alkynyl, aryl or heteroaryl; $M_2$ is absent, O, S, SO, $SO_2$, $N(R_8)$, or C=O; $M_3$ is absent, C=O, O, S, SO, $SO_2$ or $N(R_8)$; $M_4$ is hydrogen, halogen, CN, $N_3$, hydroxy, substituted hydroxy, amino, substituted amino, $CF_3$, $C_1$-$C_6$ alkyl, $C_2$-$C_6$ alkenyl, $C_2$-$C_6$ alkynyl, cycloalkyl, heterocyclic, aryl or heteroaryl; $R_{10}$ and $R_{20}$ are independently hydrogen, alkyl, substituted alkyl, aryl or substituted aryl; and X, Y and Z are as previously defined in claim 2.

6. A compound according to claim 2 selected from the compounds delineated in Table A or its geometric isomers, enantiomers, diastereomers, racemates, pharmaceutically acceptable salts and solvates thereof:

TABLE A

| Compound # | Structure |
|---|---|
| 1 | 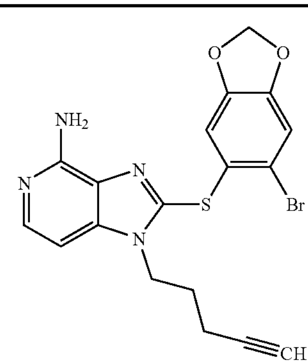 |

TABLE A-continued

| Compound # | Structure |
|---|---|
| 2 | 4-amino-imidazo[4,5-c]pyridine, 2-[(6-chloro-1,3-benzodioxol-5-yl)thio]-, 1-(pent-4-yn-1-yl) |
| 3 | 4-amino-imidazo[4,5-c]pyridine, 2-[(6-iodo-1,3-benzodioxol-5-yl)thio]-, 1-(pent-4-yn-1-yl) |
| 4 | 4-amino-imidazo[4,5-c]pyridine, 2-[(6-iodo-1,3-benzodioxol-5-yl)thio]-, 1-pentyl |
| 5 | 4-amino-imidazo[4,5-c]pyridine, 2-[(7-bromo-2,3-dihydro-1,4-benzodioxin-6-yl)thio]-, 1-(pent-4-yn-1-yl) |

TABLE A-continued

| Compound # | Structure |
|---|---|
| 6 | 4-amino-imidazo[4,5-c]pyridine, 2-[(7-chloro-2,3-dihydro-1,4-benzodioxin-6-yl)thio]-, 1-(pent-4-yn-1-yl) |
| 7 | 4-amino-imidazo[4,5-c]pyridine, 2-[(7-iodo-2,3-dihydro-1,4-benzodioxin-6-yl)thio]-, 1-(pent-4-yn-1-yl) |
| 8 | 4-amino-imidazo[4,5-c]pyridine, 2-[(7-iodo-2,3-dihydro-1,4-benzodioxin-6-yl)thio]-, 1-pentyl |
| 9 | 4-amino-imidazo[4,5-c]pyridine, 2-[(2,3-dihydro-1-benzofuran-5-yl)thio]-, 1-(pent-4-yn-1-yl) |

TABLE A-continued

| Compound # | Structure |
|---|---|
| 10 | 4-amino-2-(benzofuran-5-ylthio)-1-(pent-4-yn-1-yl)-1H-imidazo[4,5-c]pyridine |
| 11 | 4-amino-2-((3-methoxyphenyl)thio)-1-(pent-4-yn-1-yl)-1H-imidazo[4,5-c]pyridine |
| 12 | 4-amino-2-((2-iodo-5-methoxyphenyl)thio)-1-(pent-4-yn-1-yl)-1H-imidazo[4,5-c]pyridine |
| 13 | 4-amino-2-((2-bromo-5-methoxyphenyl)thio)-1-(pent-4-yn-1-yl)-1H-imidazo[4,5-c]pyridine |
| 14 | 4-amino-2-((2-chloro-5-methoxyphenyl)thio)-1-(pent-4-yn-1-yl)-1H-imidazo[4,5-c]pyridine |
| 15 | 4-amino-2-((2-iodo-4,5-dimethoxyphenyl)thio)-1-(pent-4-yn-1-yl)-1H-imidazo[4,5-c]pyridine |
| 16 | 4-amino-2-((2-iodo-4,5-dihydroxyphenyl)thio)-1-(pent-4-yn-1-yl)-1H-imidazo[4,5-c]pyridine |
| 17 | 4-amino-2-((5-methoxy-2-nitrophenyl)thio)-1-(pent-4-yn-1-yl)-1H-imidazo[4,5-c]pyridine |
| 18 | 4-amino-2-((2-cyano-5-methoxyphenyl)thio)-1-(pent-4-yn-1-yl)-1H-imidazo[4,5-c]pyridine |
| 19 | 4-amino-2-((2-acetyl-5-methoxyphenyl)thio)-1-(pent-4-yn-1-yl)-1H-imidazo[4,5-c]pyridine |

TABLE A-continued
| Compound # | Structure |
|---|---|
| 20 | 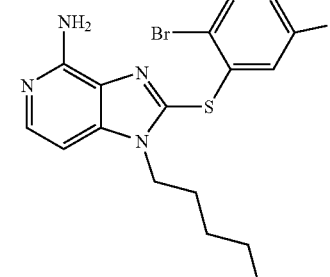 |
| 21 | 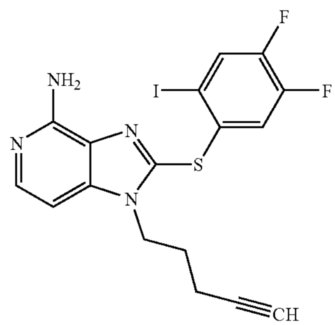 |
| 22 | 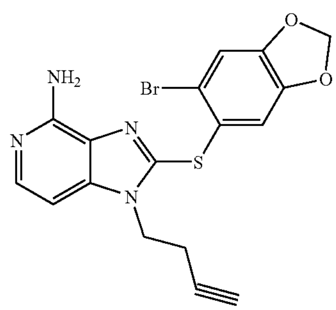 |
| 23 | 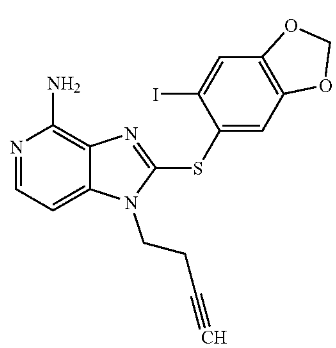 |
| 24 | |
| 25 | |
| 26 | |
| 27 | |
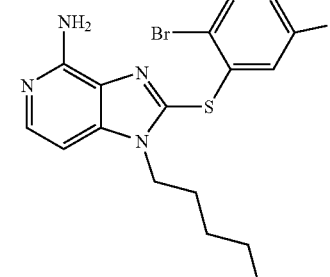

TABLE A-continued

| Compound # | Structure |
|---|---|
| 28 | (4-amino-imidazo[4,5-c]pyridine with 2-S-(6-iodo-benzo[1,3]dioxol-5-yl) and N1-(CH2)2CN propyl chain) |
| 29 | (4-amino-imidazo[4,5-c]pyridine with 2-S-(6-bromo-benzo[1,3]dioxol-5-yl) and N1-(CH2)3CN butyl chain) |
| 30 | (4-amino-imidazo[4,5-c]pyridine with 2-S-(6-iodo-benzo[1,3]dioxol-5-yl) and N1-(CH2)4CN pentyl chain) |
| 31 | (4-amino-imidazo[4,5-c]pyridine with 2-S-(6-bromo-benzo[1,3]dioxol-5-yl) and N1-CH2CH2NH2) |

TABLE A-continued

| Compound # | Structure |
|---|---|
| 32 | (4-amino-imidazo[4,5-c]pyridine with 2-S-(6-iodo-benzo[1,3]dioxol-5-yl) and N1-CH2CH2NH2) |
| 33 | (4-amino-imidazo[4,5-c]pyridine with 2-S-(6-bromo-benzo[1,3]dioxol-5-yl) and N1-CH2CH2NH-neopentyl) |
| 34 | (4-amino-imidazo[4,5-c]pyridine with 2-S-(6-iodo-benzo[1,3]dioxol-5-yl) and N1-CH2CH2NH-CH2C(CH3)3) |
| 35 | (4-amino-imidazo[4,5-c]pyridine with 2-S-(6-chloro-benzo[1,3]dioxol-5-yl) and N1-CH2CH2NH-CH2C(CH3)3) |

TABLE A-continued

| Compound # | Structure |
|---|---|
| 36 | 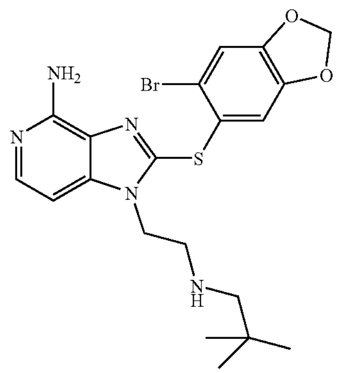 |
| 37 | 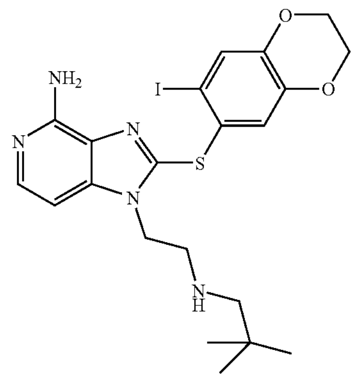 |
| 38 | 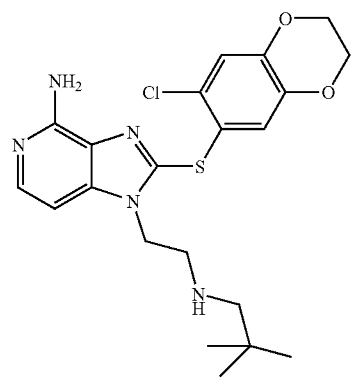 |
| 39 | 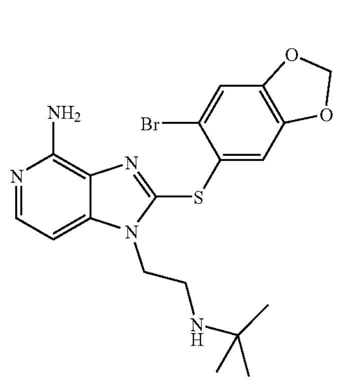 |
| 40 | |
| 41 | |
| 42 | |
| 43 | |

TABLE A-continued

| Compound # | Structure |
|---|---|
| 44 | 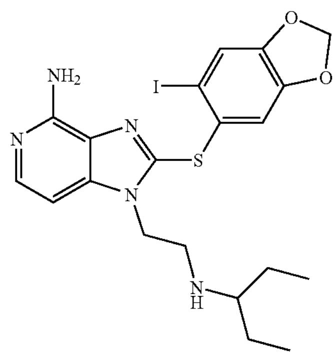 |
| 45 | 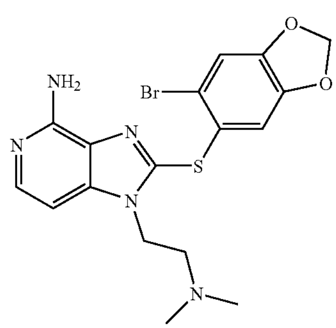 |
| 46 | 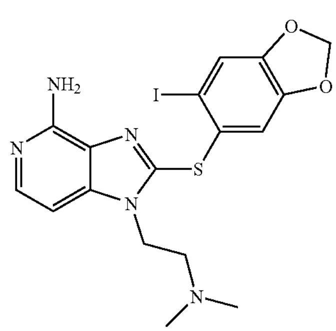 |
| 47 | 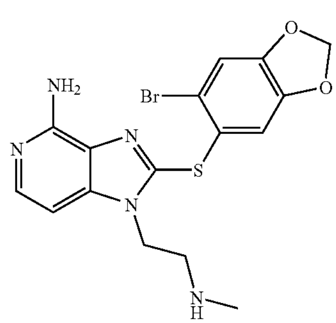 |
| 48 | |
| 49 | |
| 50 | |
| 51 | |

TABLE A-continued

| Compound # | Structure |
|---|---|
| 52 | 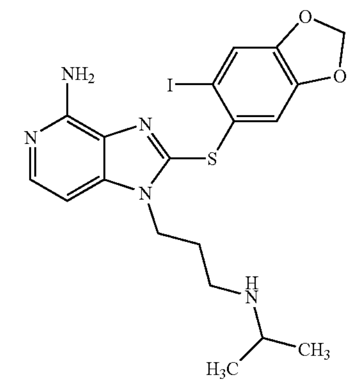 |
| 53 | 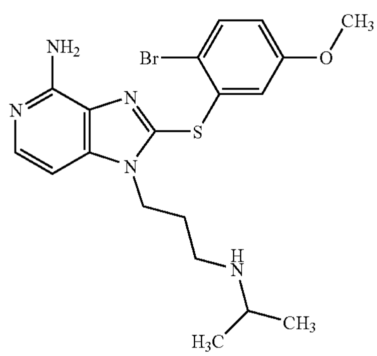 |
| 54 | 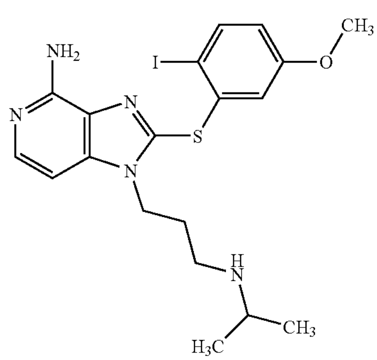 |
| 55 | 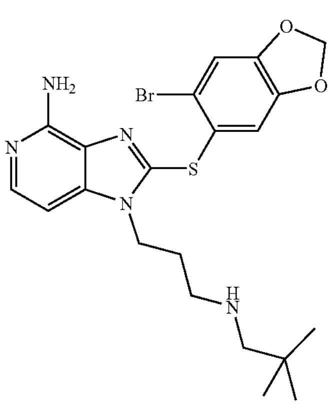 |
| 56 | 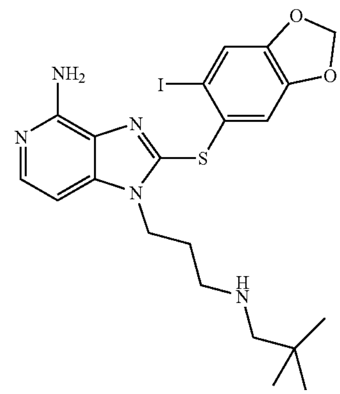 |
| 57 | 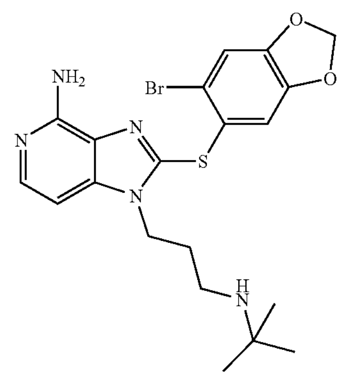 |
| 58 | 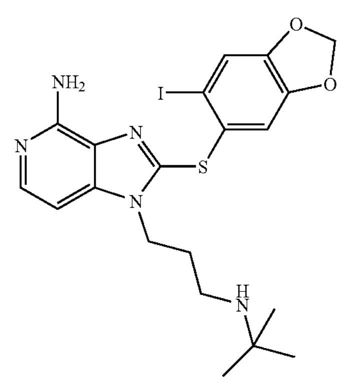 |
| 59 | 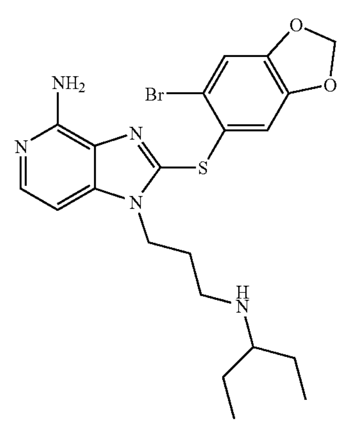 |

TABLE A-continued
| Compound # | Structure |
|---|---|
| 60 | 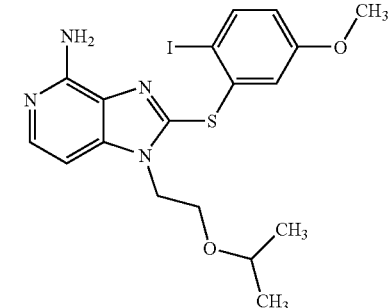 |
| 61 | 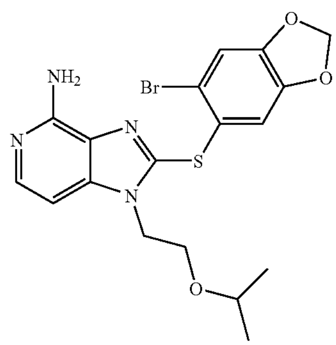 |
| 62 | 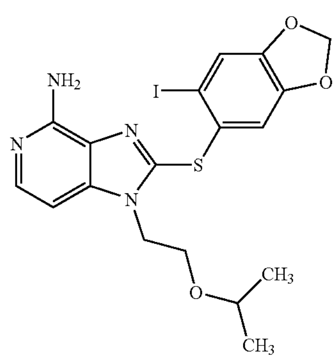 |
| 63 | 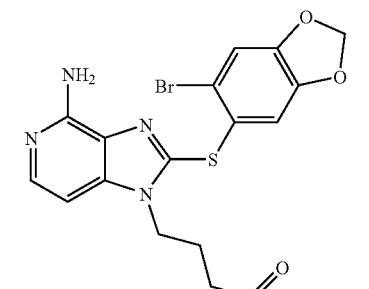 |
TABLE A-continued
| Compound # | Structure |
|---|---|
| 64 | 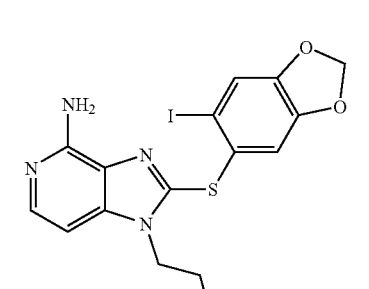 |
| 65 | 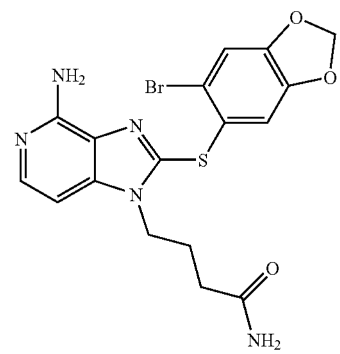 |
| 66 | 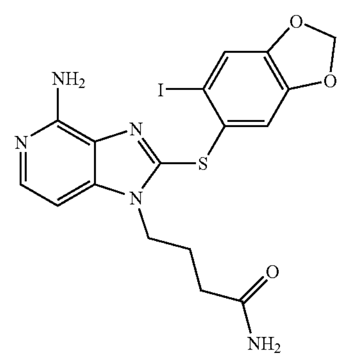 |
| 67 | 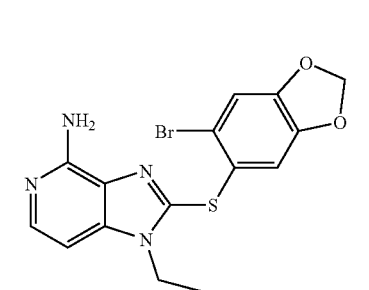 |

TABLE A-continued
| Compound # | Structure |
|---|---|
| 68 | 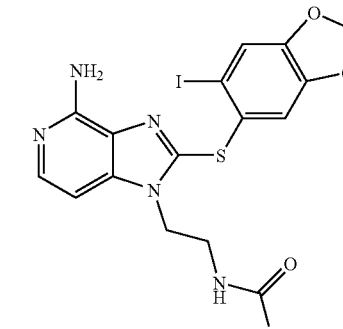 |
| 69 | 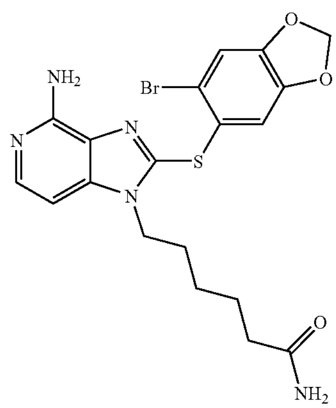 |
| 70 | 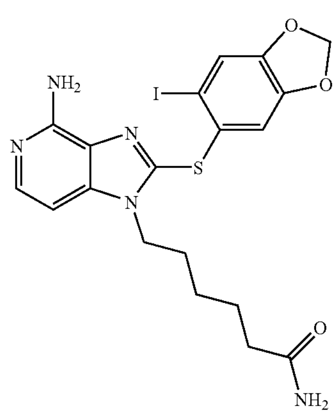 |
| 71 | 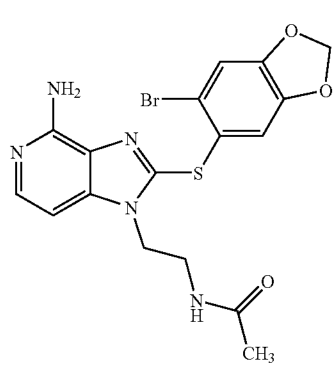 |
| 72 | 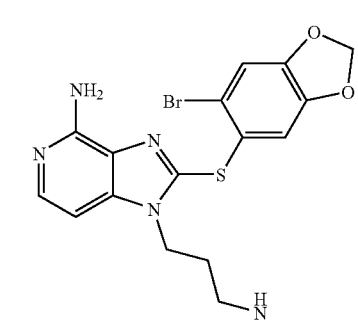 |
| 73 | 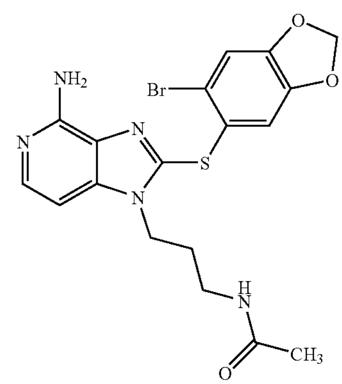 |
| 74 | 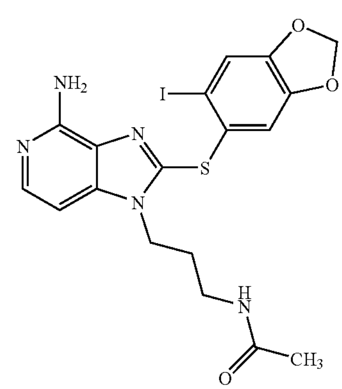 |
| 75 | 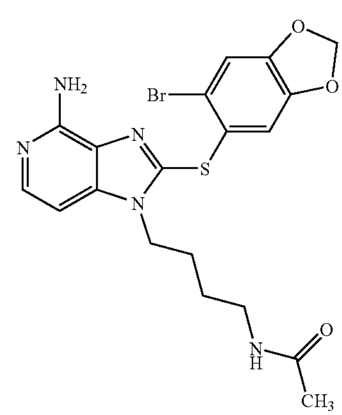 |

TABLE A-continued

| Compound # | Structure |
|---|---|
| 76 | (structure) |
| 77 | (structure) |
| 78 | (structure) |
| 79 | (structure) |
| 80 | (structure) |
| 81 | (structure) |
| 82 | (structure) |
| 83 | (structure) |

TABLE A-continued

| Compound # | Structure |
|---|---|
| 84 | 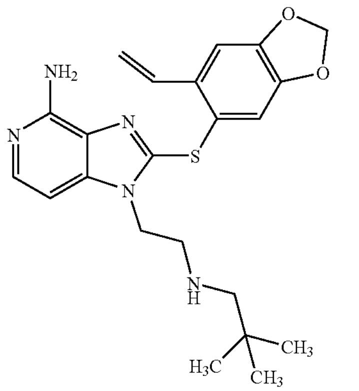 |
| 85 | 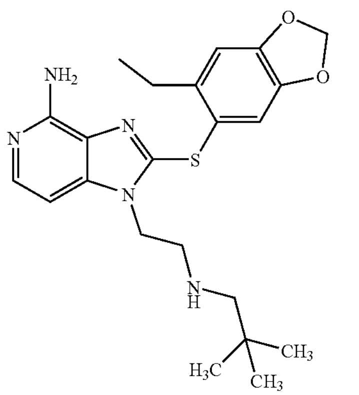 |
| 86 | 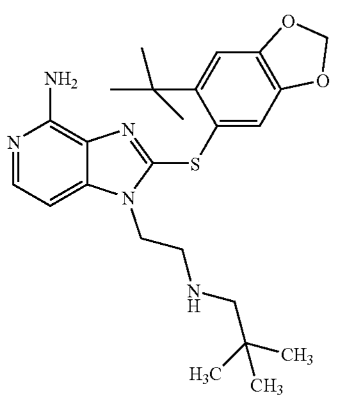 |
| 87 | 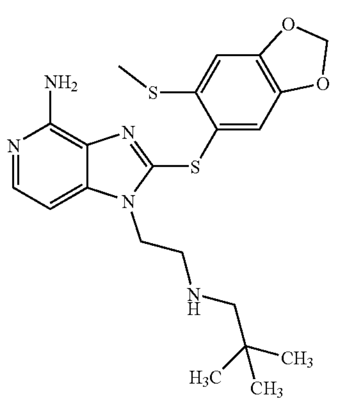 |
| 88 | |
| 89 | |
| 90 | |
| 91 | |

TABLE A-continued

| Compound # | Structure |
|---|---|
| 92 | 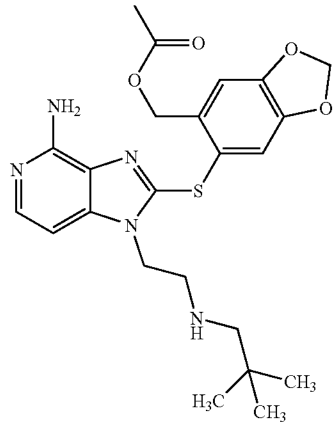 |
| 93 | 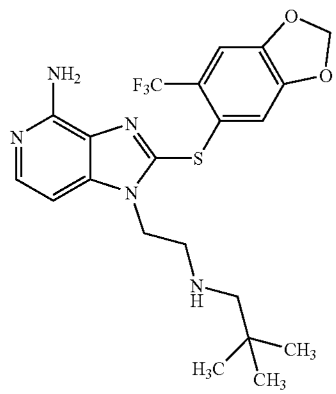 |
| 94 | 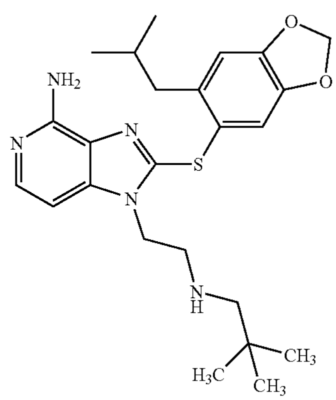 |
| 95 | 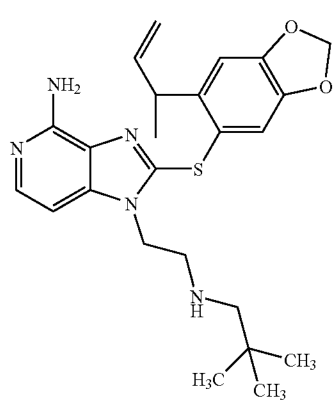 |
| 96 | |
| 97 | |
| 98 | |

TABLE A-continued

| Compound # | Structure |
|---|---|
| 99 | (structure) |
| 100 | (structure) |
| 101 | (structure) |
| 102 | (structure) |
| 103 | (structure) |
| 104 | (structure) |
| 105 | (structure) |

TABLE A-continued

| Compound # | Structure |
|---|---|
| 106 | 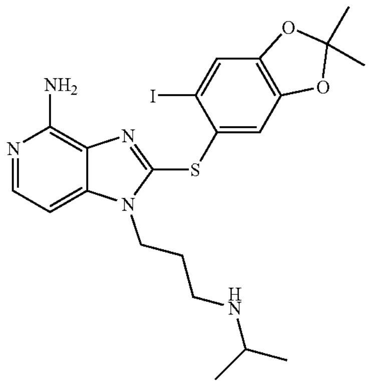 |
| 107 | 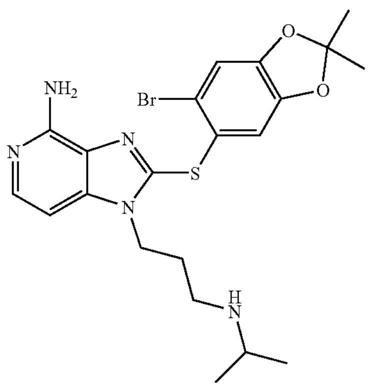 |
| 108 | 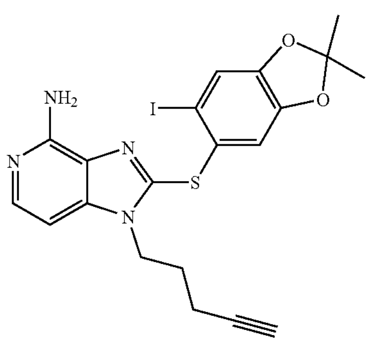 |
| 109 | 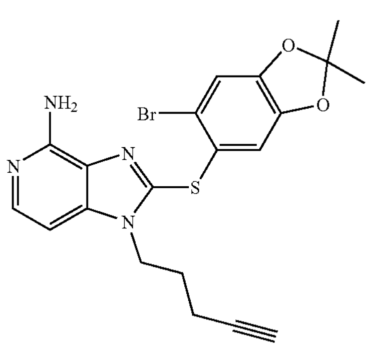 |
| 110 | |
| 111 | |
| 112 | |
| 113 | |

TABLE A-continued

| Compound # | Structure |
|---|---|
| 114 | 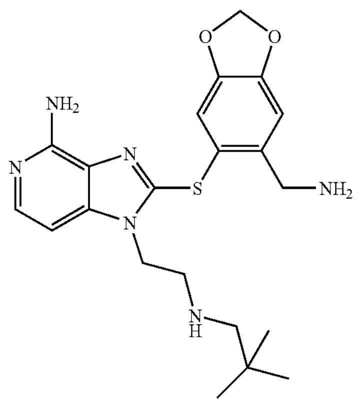 |
| 115 | 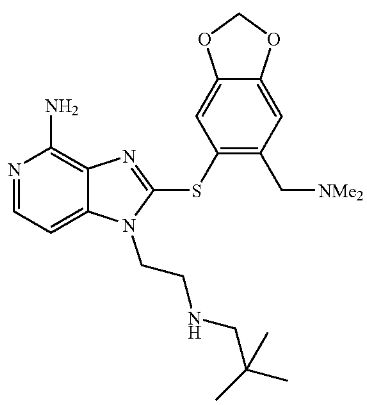 |
| 116 | 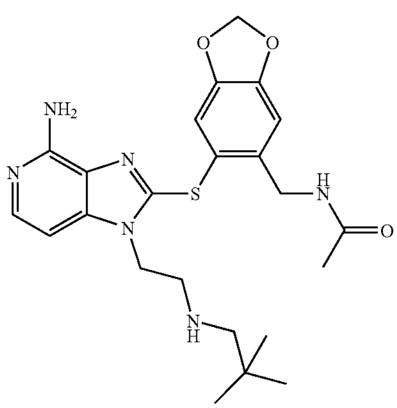 |
| 117 | 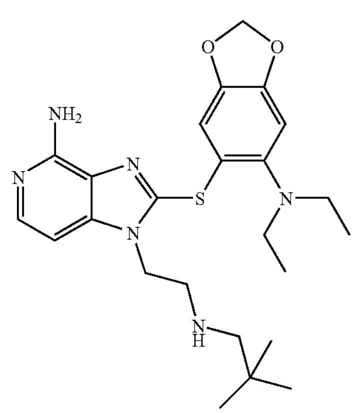 |
| 118 | 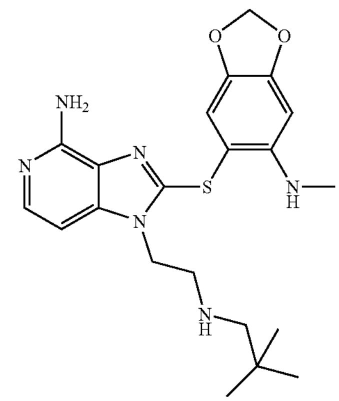 |
| 119 | 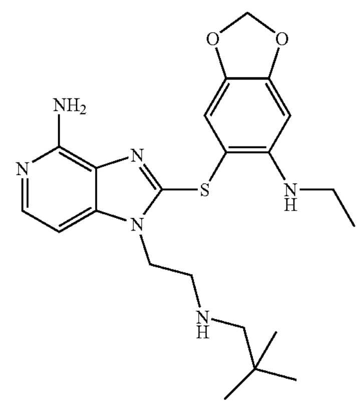 |
| 120 | 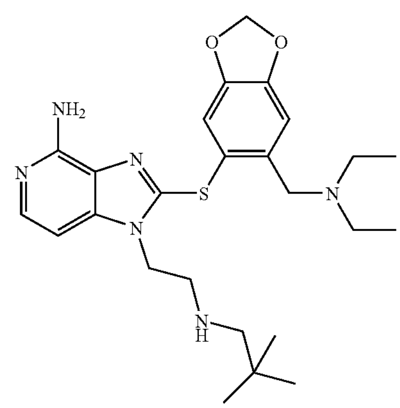 |
| 121 | 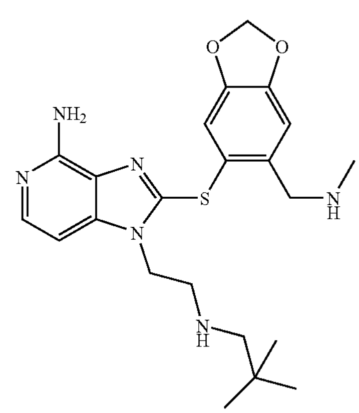 |

TABLE A-continued

| Compound # | Structure |
|---|---|
| 123 | 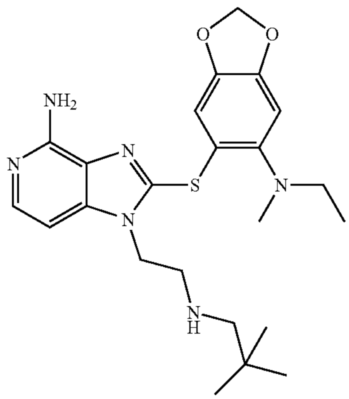 |
| 124 | 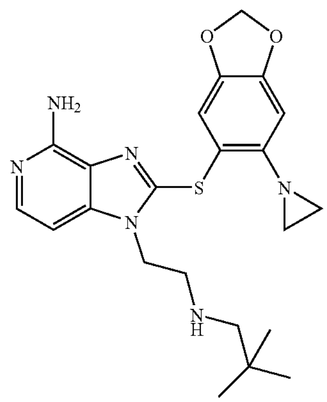 |
| 125 | 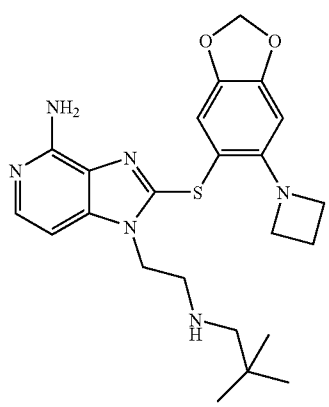 |
| 126 | 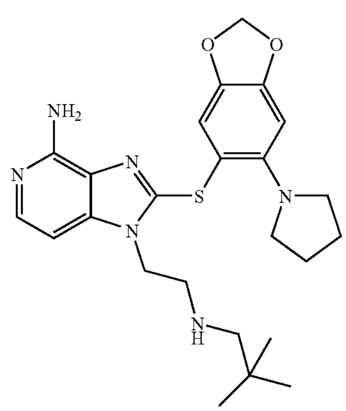 |
| 127 | |

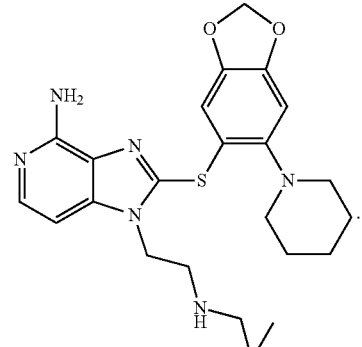
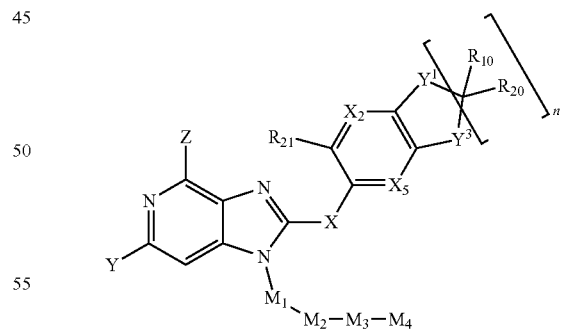

7. A pharmaceutical composition comprising as an active ingredient a compound of claim 2 and a pharmaceutical acceptable carrier.

8. A method of treating cell proliferative disorder that requires or is facilitated by expression of an HSP90 protein in a subject in need thereof, the method comprising administering to the subject a therapeutically effective amount of the pharmaceutical composition of claim 7, wherein said cell proliferative disorder is cancer.

9. The method of claim 8, wherein said cancer selected from the group consisting of papilloma, blastoglioma, Kaposi's sarcoma, melanoma, non-small cell lung cancer, ovarian cancer, prostate cancer, colon cancer, squamous cell carcinoma, astrocytoma, head cancer, neck cancer, bladder cancer, breast cancer, lung cancer, colorectal cancer, thyroid cancer, pancreatic cancer, renal cell carcinoma, gastric cancer, hepatocellular carcinoma, neuroblastoma, leukemia, lymphoma, vulvar cancer, Hodgkin's disease and Burkitt's disease.

10. A method for the treatment of cancer in a subject in need thereof, comprising administering to the subject a compound of claim 7.

11. A compound according to claim 5 represented by formula (V):

or its geometric isomers, enantiomers, diastereomers, racemates, pharmaceutically acceptable salts, and solvates thereof, wherein $X_2$ and $X_5$ are CH; $R_{21}$ is amino, substituted amino, substituted or unsubstituted alkylamino, substituted or unsubstituted dialkylamino; $Y_1$ and $Y_3$ are independently O, S, N($R_8$), CH($R_{21}$); n is 1; $M_1$ is absent, $C_1$-$C_6$ alkyl, $C_2$-$C_6$ alkenyl, $C_2$-$C_6$ alkynyl; $M_2$ is N($R_8$); $M_3$ is absent; $M_4$ is $C_1$-$C_6$ alkyl, $C_2$-$C_6$ alkenyl, $C_2$-$C_6$ alkynyl, cycloalkyl; $R_{10}$ and $R_{20}$ are independently hydrogen, alkyl; X is O; Y is H; and Z is amino, substituted or unsubstituted alkylamino, or substituted or unsubstituted dialkylamino; $R_8$ is hydrogen, acyl, aliphatic or substituted aliphatic.

12. A compound of claim 11 wherein $Y_1$ is O, $Y_3$ is O, $R_{10}$ is H, and $R_{20}$ is H.

13. A compound of formula:

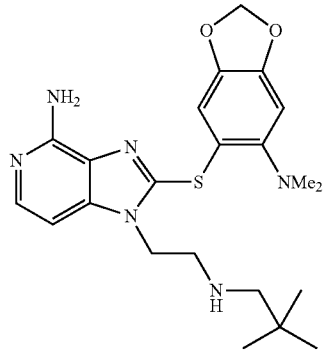

Compound-111

Compound 111
or its pharmaceutically acceptable salts or solvate thereof.

14. A compound of formula:

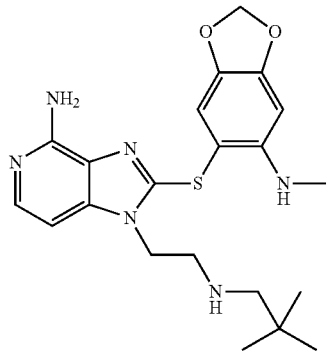

Compound-118

Compound 118
or its pharmaceutically acceptable salts or solvate thereof.

* * * * *

UNITED STATES PATENT AND TRADEMARK OFFICE
CERTIFICATE OF CORRECTION

PATENT NO. : 8,324,240 B2
APPLICATION NO. : 12/045509
DATED : December 4, 2012
INVENTOR(S) : Xiong Cai, Changgeng Qian and Haixiao Zhai It is certified that error appears in the above-identified patent and that said Letters Patent is hereby corrected as shown below:

Claim 6: Column 144, under compound 98, please delete

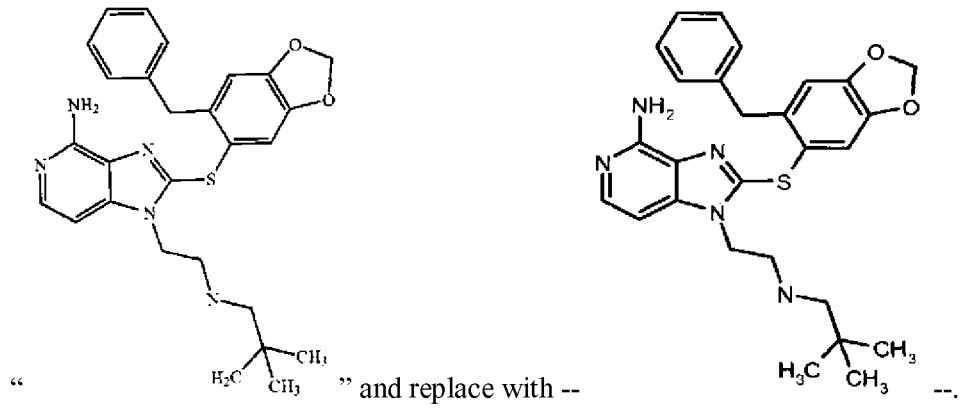

Column 145, under compound 99, please delete

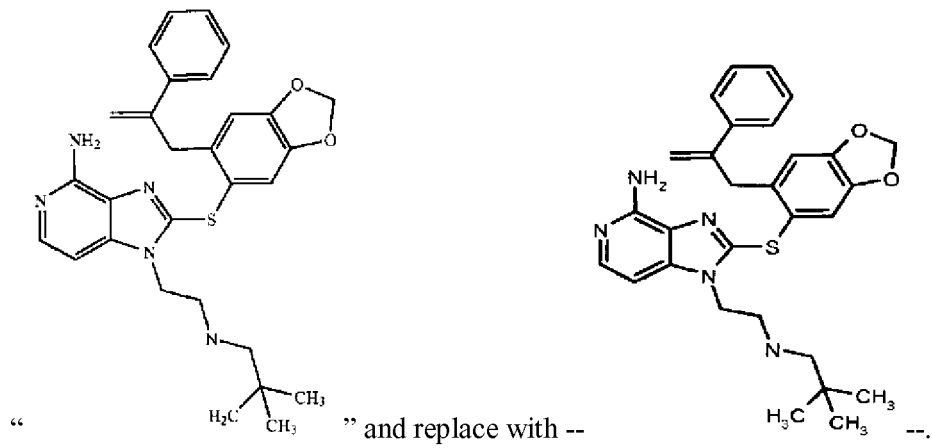

Signed and Sealed this
Second Day of April, 2013

Teresa Stanek Rea
*Acting Director of the United States Patent and Trademark Office*

CERTIFICATE OF CORRECTION (continued)
U.S. Pat. No. 8,324,240 B2

Column 145, under compound 100, please delete

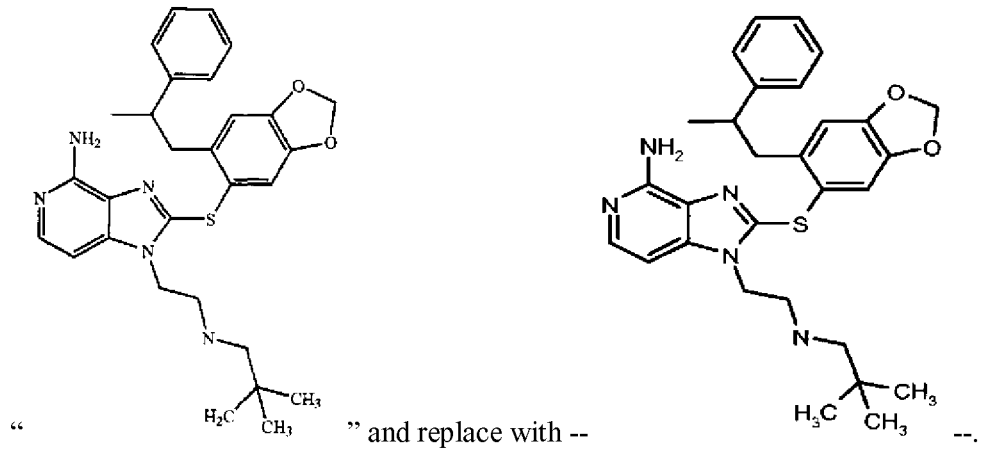

" and replace with --   --.

Column 145, under compound 101, please delete

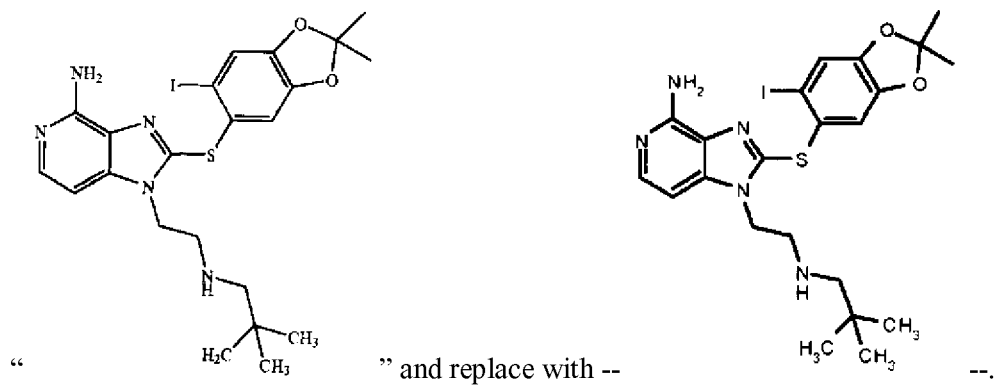

" and replace with --   --.

Column 148, under compound 112, please delete

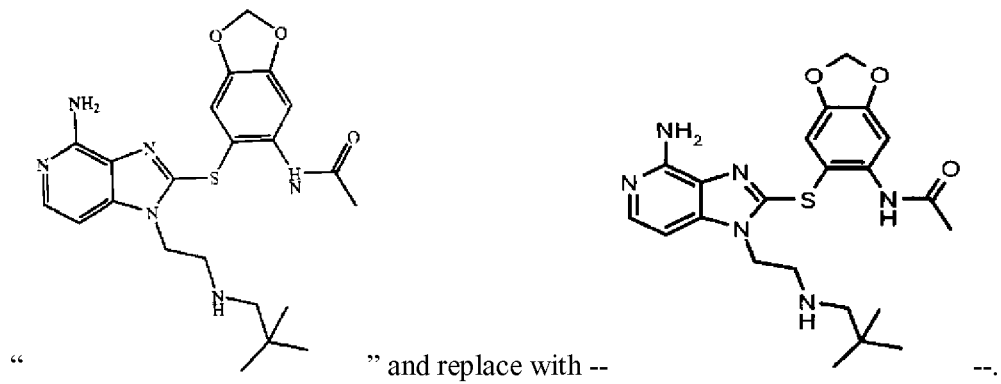

" and replace with --   --.

UNITED STATES PATENT AND TRADEMARK OFFICE
CERTIFICATE OF CORRECTION

| | | |
|---|---|---|
| PATENT NO. | : 8,324,240 B2 | Page 1 of 1 |
| APPLICATION NO. | : 12/045509 | |
| DATED | : December 4, 2012 | |
| INVENTOR(S) | : Xiong Cai et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 791 days.

Signed and Sealed this
Second Day of July, 2013

Teresa Stanek Rea
*Acting Director of the United States Patent and Trademark Office*